(12) United States Patent
Jessell et al.

(10) Patent No.: US 6,235,885 B1
(45) Date of Patent: *May 22, 2001

(54) RAT HEDGEHOG PROTEIN-1 (VHH-1)

(75) Inventors: Thomas M. Jessell; Jane Dodd; Henk Roelink, all of New York, NY (US); Thomas Edlund, Holmsund (SE)

(73) Assignee: The Trustees of Columbia University In the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/757,230

(22) Filed: Nov. 27, 1996

Related U.S. Application Data

(63) Continuation of application No. 08/202,040, filed on Feb. 25, 1994, now abandoned.

(51) Int. Cl.$^7$ .................................................. C07K 14/475
(52) U.S. Cl. ........................................ 530/399; 530/350
(58) Field of Search ..................................... 530/350, 399

(56) References Cited

U.S. PATENT DOCUMENTS

| 5,196,316 | 3/1993 | Iwasaki et al. . |
| 5,789,543 | 8/1998 | Ingham et al. . |
| 5,844,079 | 12/1998 | Ingham et al. . |
| 6,057,091 | * 2/2000 | Beachy et al. . |

FOREIGN PATENT DOCUMENTS

| WO9518556 | 7/1995 | (WO) . |
| WO96/17924 | 6/1996 | (WO) . |

OTHER PUBLICATIONS

Fietz, M. J. et al. (1994) "The Hedgehog gene family in Drosophila and Vertebrate Development" *Development*, 1994 Supplement 43–51. (Exhibit 6).
Sambrook, J., et al. Molecular Cloning, A Laboratory Manual, Second Edition, Cold Spring Harbor Press, 8.46–8.47, 9.2–9.3, 16.3–16.4, 17.2 (1989) (Exhibit 7).
Basler, K. and Struhl, G. (1994) "Compartment boundaries and the control of Drosophila limb pattern by hedgehog protein." *Nature* 386: 206–214.
Chang, D.T., et al. (1994) "Products, genetic linkage and limb patterning activity of a murine hedgehog gene." *Development* 120: 3339–3353.
Herberlain, U., et al. (1993) "The TGFB homolog dpp and the segment polarity gene hedgehog are required for propagation of a morphogenetic wave in the Drosophila retina." *Cell* 75: 913–926.
Heemskerk, J. and DiNardo, S. (1994) "Drosophila hedgehog acts as a morphogen in cellular patterning." *Cell* 76: 449–460.

Hidalgo, A. and Ingham, P. (1990) "Cell patterning in the Drosophila segment spatial regulation of the segment polarity gene patched." *Development* 110: 291–301.
Hynes, M., et al. (1995) "Control of neuronal diversity by the floor plate: contact–mediated induction of midbrain dopaminergic neurons." *Cell* 80: 95–101.
Ingham, P.W. (1993) "Localized hedgehog activity controls spatial limits of wingless transcription in the Drosophila embryo." *Nature* 366: 560–582.
Jessell, T.M. and Dodd, J. (1992) "Floor plate–derived signals and the control of neural cell pattern in vertebrates." *Harvey Lect.* 85: 87–128.
Krauss, S., et al. (1993) "A functionally conserved homolog of the Drosophila segment polarity gene hedgehog is expressed in tissues with polarizing activity in zebrafish embryos." *Cell* 75: 1431–1444.
Lee, J.J., et al. (1992) "Secretion and localization transcription suggest a role in positional signaling for products of the segmentation gene hedgehog." *Cell* 71: 33–50.
Ma, C., et al. (1993) "The segment polarity gene hedgehog is required for progression of the morphogenetic furrow in the developing Drosophila eye." *Cell* 75: 927–938.
Mohler, J. (1988) "Requirements for hedgehog, a segmental polarity gene, in patterning larval and adult cuticle of Drosophila." *Genetic* 120: 1061–1072.
Mohler, J. and Vani, K. (1992) "Molecular organization and embryonic expression of the hedgehog gene involved in cell–cell communication in segmental patterning of Drosophila." *Development* 115: 957–971.
Nusslein–Volhard, C. and Wieschaus, E. (1992) "Mutations affecting segment number and polarity in Drosophila." *Nature* 287: 795–801.
Placzek, M., et al. (1990) "Orientation of commissural axons in vitro in response to a floor plate derived chemoattractant." *Development* 110: 19–30.
Placzek, M., et al. (1990) "Mesodermal control of neural cell identity: floor plate induction by the notochord." *Science* 250: 985–988.

(List continued on next page.)

Primary Examiner—Marianne P. Allen
(74) Attorney, Agent, or Firm—John P. White; Cooper & Dunham LLP

(57) ABSTRACT

This invention provides an isolated nucleic acid molecule encoding a vertebrate Vhh-1 protein. The preferred embodiments are rat and human Vhh-1 protein. This invention provides purified vertebrate Vhh-1 protein and a method to purify same. This invention provides isolated nucleic acid molecules encoding a human and a rat Vhh-1 protein and the purified rat and human Vhh-1 protein encoded by same. This invention provides a vector encoding a vertebrate Vhh-1 protein and mammalian cells comprising such vectors. This invention provides antibodies directed to a vertebrate Vhh-1 protein. This invention further provides nucleic acid probes useful for detecting a nucleic acid molecule encoding a vertebrate Vhh-1 protein. This invention provides pharmaceutical compounds comprising the human Vhh-1 protein. This invention provides nonhuman transgenic animals which express DNA encoding a vertebrate Vhh-1 protein. This invention provides treatments for alleviating abnormalities associated with the vertebrate Vhh-1 protein.

1 Claim, 30 Drawing Sheets

OTHER PUBLICATIONS

Placzek, M., et al. (1991) "Control of dorso–ventral pattern in vertebrate neural development induction and polarizing properties of the floor plate." *Development* 113 (Suppl. 2): 105–122.

Placzek, M., et al. (1992) "Induction of floor plate differentiation by contact–dependent, homeogenetic signals." *Development* 117: 205–218.

Roelink, H. and Nusse, R. (1991) "Expression of two members of the Wnt family during mouse development: restricted temporal and spatial patterns in the developing neural tube." *Genes & Dev.* 5: 381–388.

Roelink, H., et al. (1994) "Floor plate and motor neuron induction by vhh–1, a vertebrate homolog of hedgehog expressed by the notochord." *Cell* 76: 761–775.

Tabata, T. (1992) "The Drosophila hedgehog gene is expressed specifically in posterior compartment cells and is a target of engrailed regulation." *Genes Dev.* 6: 2835–2646.

Tashiro, S. (1993) "Structure and expression of hedgehog, a Drosophila segment–polarity gene required for cell–cell communication." *Gene* 124: 183–189.

Taylor, A.M., et al. (1993) "Contrasting distributions of patched and hedgehog proteins in the Drosophila embryo." *Mech. Dev.* 42: 89–96.

Yamada, T., et al. (1991) "Control of cell pattern in the developing nervous system: polarizing activity of the floor plate and notochord." *Cell* 64: 635–647.

Yamada, T., et al. (1993) "Control of cell pattern in the neural tube: motor neuron induction by diffusible factors from notochord and floor plate." *Cell* 73: 673–686.

Riddle, R.D. et al., *Cell,* 75: 1401–16, Dec. 31, 1993.*

Echelard, Y. et al., *Cell,* 75: 1417–1430, Dec. 31, 1993.*

* cited by examiner

FIGURE 1-1

| | | | | | | | | | | | | | | | | |
|---|---|---|---|---|---|---|---|---|---|---|---|---|---|---|---|---|
| TGG | GTC | TAC | TAT | GAA | TCC | AAA | GCT | CGC | ATC | CAC | TGC | TCT | GTG | AAA | GCA | 878 |
| Trp | Val | Tyr | Tyr | Glu | Ser | Lys | Ala | Arg | Ile | His | Cys | Ser | Val | Lys | Ala | |
| | | 175 | | | | 180 | | | | | | 185 | | | | |
| GAG | AAC | TCC | GTG | GCG | GCC | AAA | TCT | GAC | GGC | TGC | TTC | CCG | GGA | TCA | GCC | 926 |
| Glu | Asn | Ser | Val | Ala | Ala | Lys | Ser | Asp | Gly | Cys | Phe | Pro | Gly | Ser | Ala | |
| | | 190 | | | | 195 | | | | | | 200 | | | | |
| ACA | GTG | CAC | CTG | GAG | CAG | GGT | GGC | ACC | AAG | TTA | GTG | AAG | GAT | CTA | AGT | 974 |
| Thr | Val | His | Leu | Glu | Gln | Gly | Gly | Thr | Lys | Leu | Val | Lys | Asp | Leu | Ser | |
| 205 | | | | 210 | | | | | 215 | | | | | | 220 | |
| CCC | GGG | GAC | CGC | GTG | CTG | GCG | GCT | GAC | GAC | CAG | GGC | CGG | CTG | CTG | TAC | 1022 |
| Pro | Gly | Asp | Arg | Val | Leu | Ala | Ala | Asp | Asp | Gln | Gly | Arg | Leu | Leu | Tyr | |
| | | | | 225 | | | | | 230 | | | | | 235 | | |
| AGC | GAC | TTC | CTC | ACC | TTC | CTG | GAC | CGC | GAC | GAA | GGT | GCC | AAG | AAG | GTC | 1070 |
| Ser | Asp | Phe | Leu | Thr | Phe | Leu | Asp | Arg | Asp | Glu | Gly | Ala | Lys | Lys | Val | |
| | | | | 240 | | | | | 245 | | | | | 250 | | |
| TTC | TAC | GTG | ATC | GAG | ACG | CGG | GAG | CCG | CGG | GAG | CGT | CTG | CTG | CTC | ACT | 1118 |
| Phe | Tyr | Val | Ile | Glu | Thr | Arg | Glu | Pro | Arg | Glu | Arg | Leu | Leu | Leu | Thr | |
| | | 255 | | | | 260 | | | | | | 265 | | | | |
| GCC | GCG | CAC | CTG | CTC | TTC | GTG | GCG | CCG | CAC | AAC | GAC | TCC | GGG | CCC | ACT | 1166 |
| Ala | Ala | His | Leu | Leu | Phe | Val | Ala | Pro | His | Asn | Asp | Ser | Gly | Pro | Thr | |
| | | 270 | | | | 275 | | | | | | 280 | | | | |
| CCG | GGA | CCG | AGC | CCA | CTC | TTC | GCC | AGC | CGC | GTG | CGT | CCG | GGG | CAG | CGC | 1214 |
| Pro | Gly | Pro | Ser | Pro | Leu | Phe | Ala | Ser | Arg | Val | Arg | Pro | Gly | Gln | Arg | |
| 285 | | | | | 290 | | | | | 295 | | | | | 300 | |
| GTG | TAC | GTG | GTG | GCT | GAA | CGC | GGC | GGG | GAC | CGC | CGG | CTG | CTG | CCC | GCC | 1262 |
| Val | Tyr | Val | Val | Ala | Glu | Arg | Gly | Gly | Asp | Arg | Arg | Leu | Leu | Pro | Ala | |
| | | | | 305 | | | | | 310 | | | | | 315 | | |
| GCG | GTG | CAC | AGC | GTA | ACG | CTA | CGA | GAG | GAG | GCG | GCG | GGT | GCG | TAC | GCG | 1310 |
| Ala | Val | His | Ser | Val | Thr | Leu | Arg | Glu | Glu | Ala | Ala | Gly | Ala | Tyr | Ala | |
| | | | 320 | | | | | 325 | | | | | 330 | | | |
| CCG | CTC | ACG | GCG | GAC | GGC | ACC | ATT | CTC | ATC | AAC | CGG | GTG | CTC | GCC | TCG | 1358 |
| Pro | Leu | Thr | Ala | Asp | Gly | Thr | Ile | Leu | Ile | Asn | Arg | Val | Leu | Ala | Ser | |
| | | 335 | | | | 340 | | | | | | 345 | | | | |
| TGC | TAC | GCA | GTC | ATC | GAG | GAG | CAC | AGC | TGG | GCA | CAC | CGG | GCC | TTC | GCG | 1406 |
| Cys | Tyr | Ala | Val | Ile | Glu | Glu | His | Ser | Trp | Ala | His | Arg | Ala | Phe | Ala | |
| | | 350 | | | | 355 | | | | | | 360 | | | | |
| CCC | TTC | CGC | CTG | GCG | CAC | GCG | CTG | CTG | GCC | GCG | CTG | GCA | CCC | GCC | CGC | 1454 |
| Pro | Phe | Arg | Leu | Ala | His | Ala | Leu | Leu | Ala | Ala | Leu | Ala | Pro | Ala | Arg | |
| 365 | | | | | 370 | | | | | 375 | | | | | 380 | |
| ACG | GAC | GGC | GGG | GGC | GGG | GGC | AGC | ATC | CCT | GCC | CCG | CAA | TCT | GTA | GCG | 1502 |
| Thr | Asp | Gly | Gly | Gly | Gly | Gly | Ser | Ile | Pro | Ala | Pro | Gln | Ser | Val | Ala | |
| | | | | 385 | | | | | 390 | | | | | 395 | | |
| GAA | GCG | AGG | GGC | GCA | GGG | CCG | CCT | GCG | GGC | ATC | CAC | TGG | TAC | TCG | CAG | 1550 |
| Glu | Ala | Arg | Gly | Ala | Gly | Pro | Pro | Ala | Gly | Ile | His | Trp | Tyr | Ser | Gln | |
| | | | 400 | | | | | 405 | | | | | 410 | | | |

FIGURE 1-2

```
TTAAAATCAG GCTCTTTTTG TCTTTTAATT GCCGTCTCGA GACCCAACTC CGATGTGTTC  60

CGTTACCAGC GACCGGCAGC CTGCCATCGC AGCCCCTGTC TGGGTGGGGA TCGGAGACAA 120

GTCCCCTGCA GCAACAGCAG GCAAGGTTAT ATAGGAAGAG AAAGAGCCAG GCAGCGCCAG 180

AGGGAACGAA CGAGCCGAGC GAGGAAGGGA GAGCCGAGCG CAAGGAGGAG CGCACACGCA 240

CACACCCGCG CGTACCAGCT CGCGCACAGA CCGGCGCGGG GACGGCTCGC AAGTCCTCAG 300

GTTCCGCGGA CGAG ATG CTG CTG CTG CTG GCC AGA TGT TTT CTG GTG GCC     350
          Met Leu Leu Leu Leu Ala Arg Cys Phe Leu Val Ala
           1               5                   10
```

```
CTT GCT TCC TCG CTG CTG GTG TGC CCC GGA CTG GCC TGT GGG CCC GGC     398
Leu Ala Ser Ser Leu Leu Val Cys Pro Gly Leu Ala Cys Gly Pro Gly
         15               20                  25

AGG GGG TTT GGA AAG AGG CAG CAC CCC AAA AAG CTG ACC CCT TTA GCC     446
Arg Gly Phe Gly Lys Arg Gln His Pro Lys Lys Leu Thr Pro Leu Ala
     30                 35                  40

TAC AAG CAG TTT ATC CCC AAC GTA GCC GAG AAG ACC CTA GGG GCC AGC     494
Tyr Lys Gln Phe Ile Pro Asn Val Ala Glu Lys Thr Leu Gly Ala Ser
 45                  50                  55                  60

GGC CGA TAT GAA GGG AAG ATC ACA AGA AAC TCC GAA CGA TTT AAG GAA     542
Gly Arg Tyr Glu Gly Lys Ile Thr Arg Asn Ser Glu Arg Phe Lys Glu
                 65                  70                  75

CTC ACC CCC AAT TAC AAC CCC GAC ATC ATA TTT AAG GAT GAG GAA AAC     590
Leu Thr Pro Asn Tyr Asn Pro Asp Ile Ile Phe Lys Asp Glu Glu Asn
                 80                  85                  90

ACT GGA GCA GAC CGG CTG ATG ACT CAG AGG TGC AAA GAC AAG TTA AAT     638
Thr Gly Ala Asp Arg Leu Met Thr Gln Arg Cys Lys Asp Lys Leu Asn
             95                 100                 105

GCC TTG GCC ATC TCC GTG ATG AAC CAG TGG CCT GGA GTG AAG CTT CGA     686
Ala Leu Ala Ile Ser Val Met Asn Gln Trp Pro Gly Val Lys Leu Arg
         110                 115                 120

GTG ACT GAG GGC TGG GAT GAG GAC GGC CAT CAT TCA GAG GAG TCT CTA     734
Val Thr Glu Gly Trp Asp Glu Asp Gly His His Ser Glu Glu Ser Leu
125                 130                 135                 140

CAC TAT GAG GGT CGA GCA GTG GAC ATC ACC ACG TCT GAC AGG GAC CGC     782
His Tyr Glu Gly Arg Ala Val Asp Ile Thr Thr Ser Asp Arg Asp Arg
                145                 150                 155

AGC AAG TAT GGC ATG CTG GCT CGC CTG GCT GTG GAG GCT GGA TTC GAC     830
Ser Lys Tyr Gly Met Leu Ala Arg Leu Ala Val Glu Ala Gly Phe Asp
            160                 165                 170
```

FIGURE 1-3

```
CTG CTG TAC CAC ATT GGC ACC TGG CTG TTG GAC AGC GAG ACC CTG CAT   1598
Leu Leu Tyr His Ile Gly Thr Trp Leu Asp Ser Glu Thr Leu His
        415                 420                 425

CCC TTG GGA ATG GCA GTC AAG TCC AGC TGAAGTCCGA CGGGACCGGG        1645
Pro Leu Gly Met Ala Val Lys Ser Ser
        430                 435

CAGGGGGCGT GGGGGGCGGGC GGGGCGGGAA GCGACTGCCA GATAAGCAAC CGGGAAAGCG  1705

CACGGAAGGA                                                         1715
```

FIGURE 2A-1

```
        1
    hh  MDNHSSVPWA SAASVTCLSL DAKCHSSSSS SSSKSAASSI SAIPQEETQT
        51
zf vhh  .......... .MRLLTRVLL VSLLTLSLVV SGLACGPGRG YGRRRHPKKL
R  vhh  .......... MLLLLARCFL VALASSLLVC PGLACGPGRG FGKRQHPKKL
    hh  MRHIAHTQRC LSRLTSLVAL LLIVLPMVFS PAHSCGPGRG LG.RHRARNL
        101
zf vhh  TPLAYKQFIP NVAEKTLGAS GRYEGKITRN SERFKELTPN YNPDIIFKDE
R  vhh  TPLAYKQFIP NVAEKTLGAS GRYEGKITRN SERFKELTPN YNPDIIFKDE
    hh  YPLVLKQTIP NLSEYTNSAS GPLEGVIRRD SPKFKDLVPN YNRDILFRDE
        151
zf vhh  ENTGADRLMT QRCKDKLNSL AISVMNHWPG VKLRVTEGWD EDGHHFEESL
R  vhh  ENTGADRLMT QRCKDKLNAL AISVMNQWPG VKLRVTEGWD EDGHHSEESL
    hh  EGTGADRLMS KRCKEKLNVL AYSVMNEWPG IRLLVTESWD EDYHHGQESL
        201
zf vhh  HYEGRAVDIT TSDRDKSKYG TLSRLAVEAG FDWVYYESKA HIHCSVKAEN
R  vhh  HYEGRAVDIT TSDRDRSKYG MLARLAVEAG FDWVYYESKA RIHCSVKAEN
    hh  HYEGRAVTIA TSDRDQSKYG MLARLAVEAG FDWVSYVSRR HIYCSVKSDS
```

FIGURE 2A-2

```
      251
zf vhh SVAAKSGGCF PGSALVSLQD GGQKAVKDLN PGDKVLAADS AGNLVFSDFI
R  vhh SVAAKSDGCF PGSATVHLEQ GGTKLVKDLS PGDRVLAADD QGRLLYSDFL
   hh  SISSHVHGCF TPESTALLES GVRKPLGELS IGDRVLSMTA NGQAVYSEVI
      301
zf vhh MFTDRDSTTR RVFYVIETQE PVEKITLTAA HLLFVL.DNS TEDLHTMTAA
R  vhh TFLDRDEGAK KVFYVIETRE PRERLLLTAA HLLFVAPHND SGPTPGPSPL
   hh  LFMDRNLEQM QNFVQLHT.D GGAVLTVTPA HLVSWQPES. ....QKLTFV
      351
zf vhh YASSVRAGQK VMVVD.DSGQ LKSVIVQRIY T.....EEQRG SFAPVTAHGT
R  vhh FASRVRPGQR VYVVA.ERGG DRRLLPAAVH SVTLREEAAG AYAPLTADGT
   hh  FADRIEEKNQ VLVRDVETGE LRPQRVVKVG SV.....RSKG VVAPLTREGT
      401
zf vhh IVVDRILASC YAVIEDQGLA HLAFAPARLY YVVSSFLFPQ NSSSRSNATL
R  vhh ILINRVLASC YAVIEEHSWA HRAFAPFRLA HALLAALAPA RTDGGGGGSI
   hh  IVVNSVAASC YAVINSQSLA HWGLAPMRLL STLEAWLPAK EQLHSSPKVV
      451
zf vhh .......... ...QQEGVHW YSRLLYQMGT WLLDSNMLHP LGMSVNSS*
R  vhh PAPQSVAEAR GAGPPAGIHW YSQLLYHIGT WLLDSETLHP LGMAVKSS*
   hh  SSAQ...... ...QQNGIHW YANALYKVKD YVLPQSWRHD *
```

RAT HEDGEHOG PROTEIN-1 (VHH-1)

This is a continuation of application Ser. No. 08/202,040, filed Feb. 25, 1994 now abandoned.

The invention disclosed herein was made with U.S. Government support under grant number NS-30532 from the National Institute of Health, U.S. Department of Health and Human Services. Accordingly, the U.S. Government has certain rights in this invention.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

In vertebrate embryos, the neural tube displays distinct cell types at defined dorsoventral positions. Floor plate cells differentiate at the ventral midline; motor neurons appear in ventrolateral regions; and sensory relay neurons, neural crest, and roof plate cells appear dorsally. The generation of cell pattern in the neural tube depends on signals that derive from surrounding tissues. A clear example of this is the influence of axial mesoderm on the development of ventral cell types.

The differentiation of floor plate cells, motor neurons, and other ventral cell types requires inductive signals from axial mesodermal cells of the notochord. In the absence of the notochord, floor plate cells and motor neurons do not differentiate (Placzek et al., 1990b; Bovolenta and Dodd, 1991; Clarke et al., 1991; van Straaten and Hekking, 1991; Yamada et al., 1991; Ruiz l Altaba, 1992; Goulding et al., 1993; Ruiz l Altaba et al., 1993a; Halpern et al., 1993). Conversely, notochord grafts can induce the ectopic differentiation of floor plate cells and motor neurons in vivo and in vitro (van Straaten et al., 1988; Placzek et al., 1990b, 1991, 1993, Yamada et al., 1991, 1993; Ruiz l Altaba, 1992; Goulding et al., 1993). Floor plate cells themselves also possess both floor plate and motor neuron inducing activity (Yamada et al., 1991, 1993; Hatta et al., 1991; Placzek et al., 1993). In vitro assays have provided evidence that floor plate induction requires a contact-mediated signal, whereas motor neurons can be induced by diffusible signals (Yamada et al., 1993; Placzek et al., 1990b, 1993).

The differentiation of floor plate cells and motor neurons is associated with the expression of different classes of transcription factors. Floor plate cells express three members of the hepatocyte nuclear factor HNF-3/fork head gene family (Weigel and Jackie, 1990, Lai et al., 1991):Pintallavis (XFKH1/XFD1/1), HNF-3β, and HNF-3a (Dirksen and Jamrich, 1992; Knochel et al., 1992; Ruiz l Altaba and Jessell, 1992; Bolce et al., 1993; Monaghan et al., 1993; Ruiz l Altaba et al., 1993a; Sasaki and Hogan, 1993; Strahle e al., 1993). Ectopic expression of Pintallavis and HNF-3β leads to the appearance of floor plate markers in cells in the dorsal region of the neural tube (Ruiz l Altaba et al., 1992, 1993b; A. R. A. et al., unpublished data; Sasaki and Hogan, 1994), suggesting that members of this family may specify floor plate cell fate. The differentiation of motor neurons is associated with expression of islet-1, a member of the LIM homeobox gene family (Ericson et al., 1992; Yamada et al., 1993). In addition to their possible functions in cell fate determination, these transcription factors provide markers that can be used in conjunction with cell surface molecules to monitor floor plate and motor neuron differentiation.

Cell patterning in the dorsal neural tube appears to be regulated by members of two families of secreted proteins that also have prominent roles in insect development. The transforming growth factor β (TGFβ) family member dorsalin-1 is expressed in the dorsal neural tube and can induce the differentiation of neural crest cells in neural plate explants in vitro (Basler et al., 1993). Members of the wnt family are also expressed in the dorsal neural tube (Roelink and Nusse, 1991; Nusse and Varmus, 1992; Parr et al., 1993). In Drosophila, the TGFβ family member decapentaplegic. (dpp) regulates the dorsoventral pattern of the Drosophila embryo (see Ferguson and Anderson, 1992 ) and the differentiation and patterning of cells in imaginal discs (Spencer et al., 1982; Posakony et al., 1991; Campbell et al., 1993, Heberlein et al., 1993). similarly, wingless (wg), a member of the wnt gene family, controls cell fates during segmentation and imaginal disc development (Morata and Lawrence, 1977; Nusslein-Volhard and Wieschaus, 1980; Baker, 1988; Martinez-Arias et al., 1988; Struhl and Basler, 1993).

A third Drosophila gene important in the specification of cell identity is hedgehog (hh) (Nusslein-Volhard and Wieschaus, 1980). hh acts with dpp and wg to control cell fate and pattern during segmentation and imaginal disc development (Hidalgo and Ingham, 1990; Ingham, 1993; Ma et al., 1993; Heberlein et al., 1993; Basler and Struhl, 1994; Heemskerk and DiNardo, 1994). hh encodes a novel protein (Lee et al., 1992; Mohler and Vani, 1992; Tabata et al., 1992; Tashiro et al., 1993) that enters the secretory pathway (Lee et al., 1992), and genetic evidence indicates the hh function is not cell autonomous (Mohler, 1988; Heberlein et al., 1993; Ma et al., 1993; Basler and Struhl, 1994), consistent with the possibility that hh acts as a signaling molecule.

The importance of hh in cell patterning in insects prompted us to search for vertebrate homologs and to examine their potential functions during early neural development. We report here the cloning of a vertebrate homolog of hh, vhh-1, from rat. Recent independent studies have identified a vertebrate homolog of hh, sonic hedgehog (shh), that is closely related to vhh-1 and appears to regulate cell patterning in the neural tube and limb bud (Echelard et al., 993; Krauss et al., 1993, Riddle et al., 1993). Here, we present evidence that vhh-1 is involved in the induction of ventral neural cell types. vhh-1 is expressed in midline structures (in particular, the node, notochord, and floor plate) at a time when these cells have inducing activity. COS cells expressing the rat vhh-1 gene induce floor plate and motor neuron differentiation in neural plate explants in vitro. Moreover, widespread expression of the rat vhh-1 gene in frog embryos leads to ectopic expression of the floor plate markers in the neural tube. These results suggest that vhh-1 expression in the notochord provides an inductive signal that is involved in the differentiation of floor plate cells, motor neurons, and possibly other cell types in the ventral neural tube.

SUMMARY OF THE INVENTION

This invention provides an isolated nucleic acid molecule encoding a vertebrate Vhh-1 protein.

This invention provides an isolated nucleic acid molecule of encoding a rat Vhh-1 protein.

This invention provides an isolated nucleic acid molecule encoding a human Vhh-1 protein.

This invention provides a vector comprising a nucleic acid molecule encoding a vertebrate Vhh-1 protein.

This invention further provides a plasmid comprising said vector.

This invention provides a nucleic acid probe comprising a nucleic acid molecule of at least 15 nucleotides capable of specifically hybridizing with a unique sequence included within the sequence of a nucleic acid molecule comprising the gene encoding the vertebrate Vhh-1 protein and its noncoding 3' and 5' nucleotides as shown in FIGS. 1-1, 1-2 and 1-3.

This invention provides a purified vertebrate Vhh-1 protein. This invention further provides a purified rat Vhh-1 protein and a purified human Vhh-1 protein.

This invention provides a monoclonal antibody directed to a vertebrate Vhh-1 protein.

This invention provides a transgenic nonhuman mammal which comprises an isolated DNA molecule encoding a vertebrate Vhh-1 protein. This invention further provides a transgenic nonhuman mammal which comprises an isolated DNA molecule encoding a human Vhh-1 protein.

This invention provides a method of determining the physiological effects of expressing varying levels of vertebrate Vhh-1 protein which comprises producing a panel of transgenic nonhuman animals each expressing a different amount of vertebrate Vhh-1 protein.

This invention provides a method of preparing the purified vertebrate Vhh-1 protein which comprises (a) inserting a nucleic acid molecule encoding a vertebrate Vhh-1 protein in a suitable vector; (b) inserting the resulting vector in a suitable host cell; (c) recovering the vertebrate Vhh-1 protein produced by the resulting cell; and (d) purifying the vertebrate Vhh-1 protein so recovered.

This invention provides a pharmaceutical composition comprising an effective amount of a human Vhh-1 protein and a pharmaceutically acceptable carrier.

This invention provides a method for treating a human subject afflicted with an abnormality associated with the lack of one or more normally functioning motor neuron(s) which comprises introducing an amount of a pharmaceutical composition which comprises the Vhh-1 protein effective to generate motor neurons from undifferentiated motor neuron precursor cells in humans, thereby treating a human subject afflicted with an abnormality associated with a lack of one or more normally functioning motor neuron(s).

This invention provides a method of treating a human subject afflicted with a neurodegenerative disease which comprises introducing an amount of a pharmaceutical composition effective to generate motor neurons from undifferentiated motor neuron precursor cells in humans, thereby treating a human subject afflicted with a neurodegenerative disease.

A method of treating a human subject afflicted with an acute nervous system injury which comprises introducing an amount of a pharmaceutical composition effective to generate motor neurons from undifferentiated motor neuron precursor cells in humans, thereby treating a human subject afflicted with an acute nervous system injury.

A method of treating a human subject afflicted with an acute nervous system injury which is localized to a specific central axon which comprises surgical implantation of an amount of a pharmaceutical composition comprising the human Vhh-1 protein and a pharmaceutically acceptable carrier effective to generate motor neurons from undifferentiated motor neuron precursor cells located proximal to the injured axon in a human, thereby alleviating an acute nervous system injury localized to a specific central axon.

BRIEF DESCRIPTION OF THE FIGURES

FIGS. 1-1, 1-2 and 1-3

Figure 2B:
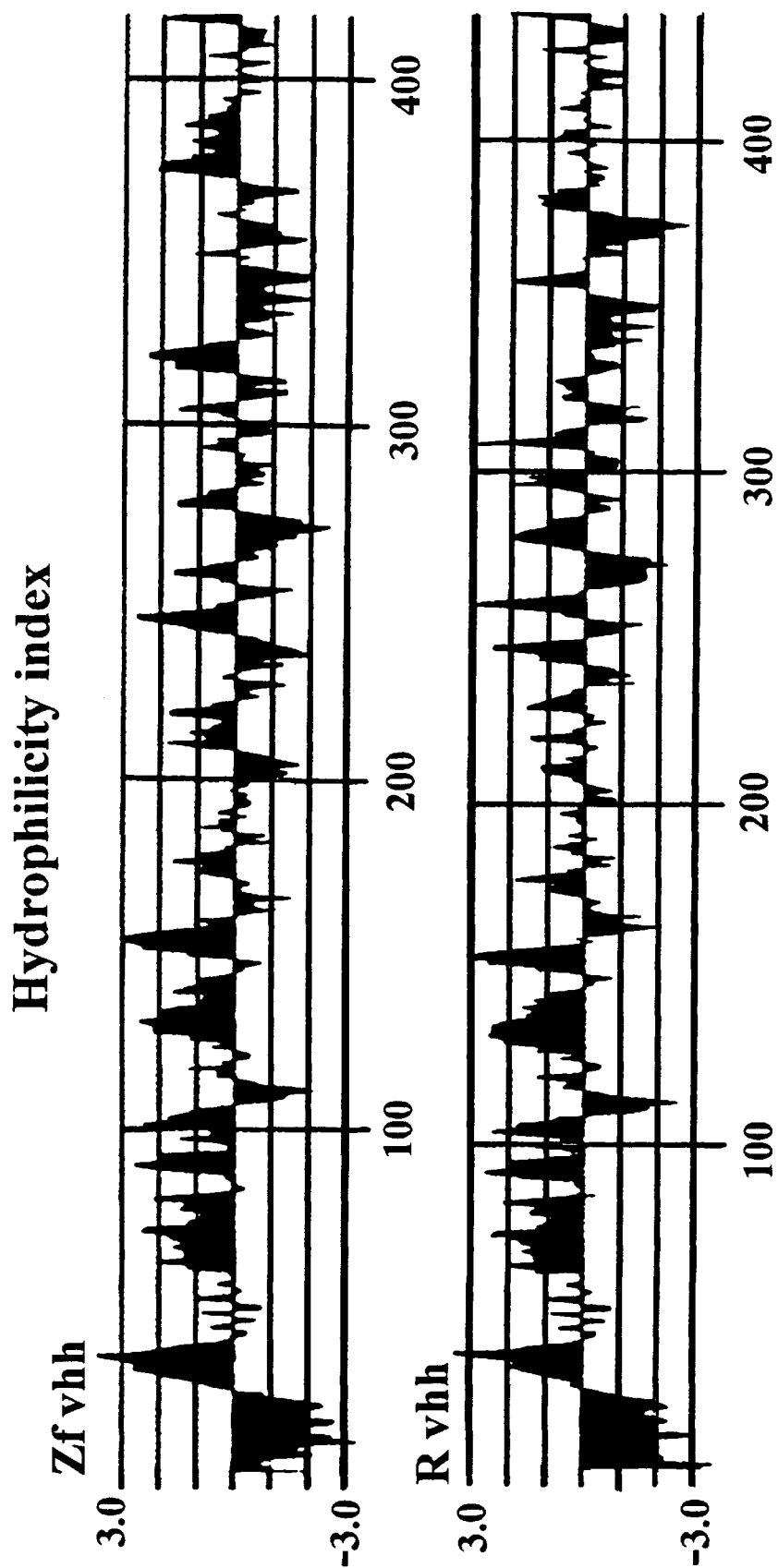

DNA Sequence of Rat Vhh-1 Protein with Corresponding Deduced Amino Acid Sequence (SEQ ID NO:1).

FIGS. 2A-1 and 2A-2

Deduced Amino Acid Sequences of Zebrafish (SEQ ID NO:7) and Rat Homologs of the Drosophila Hh Protein (SEQ ID NO:8) alignment of the zebrafish (Z1 vhh) and rat (R vhh) (SEQ ID NO:9) proteins with the Drosophila hh protein. Residues identical in all sequences are shown in bold. Gaps introduced to optimize the alignment are shown by ellipses. The vhh-1 sequence shows no homology with other proteins in the National Center for Biotechnology Information blast peptide sequence data base with the exception of resides 113–211, which show 39% conservation with the outer surface protein A of *Borella burgdorferi*, a lyme disease spirochete (Eiffert et al., 1992).

FIG. 2B

Analysis of the hydrophilicity (Kyle and Doolittle, 1982) of the zebrafish and rat proteins. The $NH_2$-terminus of the protein is to the left. Negative values indicate hydrophobic residues. The $NH_2$-terminal hydrophobic region is likely to serve as a signal sequence (von Heijne, 1985). Immediately following the putative signal sequence cleavage site is a basic region that conforms to the requirements for a heparin-binding site (Cardin and Weintraub, 1989).

FIG. 3A

Localization of Rat vhh-1 mRNA by In Situ Hybridization vhh-1 mRNA expression in an E9.5 rat embryo. Labeled cells are found in the node (nd) and in the axial mesoderm laid down at the midline of the embryo in the wake of the node. Anterior is up.

Scale bar is 165 µm.

FIG. 3B

Localization of vhh-1 mRNA expression in an E10.5 rat embryo shown in side view vhh-1 mRNA expression is present in the notochord (n in [C-E]) and in floor plate cells in more rostral regions of the spinal cord, hindbrain (h), and midbrain (m). Cells in the ventral diencephalon (d) also express vhh-1 mRNA at high levels. In addition, a group of cells in the dorsal midbrain express vhh-1 mRNA. Endodermal cells in the gut (g) also express the gene. At later stages a small group of cells in the rostral telencephalon also express vhh-1 mRNA (data not shown). Scale bar is 400 µm.

FIG. 3C

Cross section showing the neural plate and surrounding tissues in an E10 rat embryo. vhh-1 mRNA expression is confined to a group of cells that lie under the midline of the neural plate.

Scale bar is 100 µm.

FIG. 3D

Cross section showing the neural plate and surrounding tissues in an E10 rat embryo. vhh-1 mRNA expression is confined to the notochord (n).

Scale bar is 100 µm.

FIG. 3E

Cross section through an E11 rat embryo showing the spinal cord and surrounding tissues. vhh-1 mRNA expression is detected in cells at the ventral midline of the spinal cord, corresponding to the floor plate (f) and to the notochord (n), which by this stage is displaced from the ventral midline of the nervous system. The border of the spinal cord is marked.

Scale bar is 180 µm.

FIG. 4A

Ectopic Expression of F-Spondin and HNF-3β in the Dorsal Neural Tube of Frog Embryos injected with a Plasmid Expressing Rat vhh-1 cross section of neurula stage (approximately stage 16) Xenopus embryo expressing rat vhh-1 mRNA from a plasmid driven by a CMV promoter. The rat vhh-1 gene is detected predominantly in one half of the neural plate. Lateral arrows denote the lateral extent of the neural plate. Abbreviations: np. neural plate: n, notochord, s, somite.

FIG. 4B

Lateral views of tadpole stage (approximately stage 34) embryos showing the pattern of F-spondin mRNA expression in an embryo injected with CMV plasmid encoding antisense Vhh-1. F-spondin is expressed in the floor plate (fp) at the ventral midline of the neural tube and in the hypochord (h) located ventral to the notochord (n).

Scale bar is 200 µm.

FIG. 4C

Lateral views of tadpole stage (approximately stage 34) embryos showing the pattern of F-spondin mRNA expression in an embryo injected with CMV plasmid encoding sense Vhh-1. Ectopic expression of F-spondin mRNA is detected in the dorsal neural tube and in the dorsal ventricular zone adjacent to the floor plate (first and last arrowheads) (Ruiz i Altaba et al. 1993a). Ectopic F-spondin expression occurs in the posterior hindbrain and in the spinal cord.

Scale bar is 200 µm.

FIG. 4D

Cross section of tadpole stage (approximately stages 32–36) embryos injected with CMV plasmid encoding antisense Vhh-1 and showing the expression of F-spondin mRNA. Embryos injected with CMV plasmids encoding antisense Vhh-1 show a normal pattern of F-spondin mRNA expression, restricted to the floor plate (fp).

Scale bar is 10 µm.

FIG. 4E

Cross section of tadpole stage (approximately stages 32–36) embryos injected with CMV plasmid encoding sense Vhh-1 and showing the expression of F-spondin mRNA. Ectopic expression of F-spondin in embryos injected with CMV plasmids encoding sense Vhh-1 is detected in roof plate cells in the hindbrain.

Scale bar is 10 µm.

FIG. 4F

Cross section of tadpole stage (approximately stages 32–36) embryos injected with CMV plasmid encoding sense Vhh-1 and showing the expression of F-spondin mRNA. Ectopic expression of F-spondin in embryos injected with CMV plasmids encoding sense Vhh-1 is detected in the roof plate cells of the spinal cord.

Scale bar is 10 µm.

FIG. 4G

Cross section of tadpole stage (approximately stages 32–36) embryos injected with CMV plasmid encoding antisense Vhh-1 and showing the expression of HNF-3β protein. Embryos injected with a CMV plasmid encoding antisense Vhh-1 show the normal pattern of HNF-3β protein expression, restricted to the floor plate (fp).

Scale bar is 10 µm.

FIG. 4H

Cross section of tadpole stage (approximately stages 32–36) embryos injected with CMV plasmid encoding sense Vhh-1 and showing the expression of HNF-3β protein. Ectopic expression of HNF-3β protein in the roof plate of the hindbrain (H) is detected in embryos expressing Vhh-1 mRNA.

Scale bar is 10 µm.

FIG. 4I

Cross section of tadpole stage (approximately stages 32–36) embryos injected with CMV plasmid encoding sense Vhh-1 and showing the expression of HNF-3β protein. Ectopic expression of HNF-3β protein in the roof plate of the spinal cord is detected in embryos expressing Vhh-1 mRNA. HNF-3β protein expression is also detected in very low levels in the notochord (n). Ectopic expression of these floor plate markers was also detected in the dorsal midbrain (data not shown).

Scale bar is 10 µm.

FIG. 5A

Induction of Floor Plate differentiation in neural plant explants by Vhh-1. Pattern of expression of the FP3 antigen in a cross section of the ventral region of an E11 rat spiral cord. FP3 expression is restricted to floor plate cells (f). The notochord (h) is unlabeled.

Scale bar is 35 µm.

FIG. 5B

Induction of Floor Plate differentiation in neural plant explants by Vhh-1. Pattern of expression of the FP4 antigen in a cross section of the ventral region of an E11 rat spinal cord. FP4 expression in the spinal cord is restricted to floor plate cells (f). The notochord (n) also expresses FP4.

Scale bar is 35 µm.

FIG. 5C

Induction of Floor Plate differentiation in neural plant explants by Vhh-1. Expression of FP3 by cells in rat neural plate explants that have been grown in contact with stage b chick notochord for 96 hours. Neural cells in proximity to the notochord express FP3.

Scale bar is 45 µm.

FIG. 5D

Induction of Floor Plate differentiation in neural plant explants by Vhh-1. Expression of FP4 by cells in rat neural plate explants grown in contact with stage 6 chick notochord for 96 hours. Neural cells in proximity to the notochord express FP4.

Scale bar is 45 µm.

FIG. 5E

Induction of Floor Plate differentiation in neural plant explants by Vhh-1. Phase-contrast micrograph showing expression of FP3 in neural plate cells grown in contact with COS cells transfected with cDNA encoding sense Vhh-1. Intense expression of FP3 is detected at regions of contact between the neural plate explant and COS cell aggregate.

Scale bar is 50 µm.

FIG. 5F

Induction of Floor Plate differentiation in neural plant explants by Vhh-1. Fluorescence micrograph showing expression of FP3 in neural plate cells grown in contact with COS cells transfected with cDNA encoding sense vhh-1. Intense expression of FP3 is detected at regions of contact between the neural plate explant and COS cell aggregate.

Scale bar is 50 µm.

FIG. 5G

Induction of Floor Plate differentiation in neural plant explants by Vhh-1. Phase-contrast micrograph showing expression of FP4 in neural plate cells grown in contact with COS cells transfected with cDNA encoding sense Vhh-1. FP4 expression is detected at regions of contact between the neural plate (np) explant and COS cells (c). The junction between COS cells and neural plate explant is shown by the dotted line.

Scale bar is 60 µm.

FIG. 5H

Induction of Floor Plate differentiation in neural plant explants by Vhh-1. Fluorescence micrograph showing expression of FP4 in neural plate cells grown in contact with COS cells transfected with cDNA encoding sense Vhh-1. FP4 expression is detected at regions of contact between the neural plate (np) explant and COS cells (c). The junction between COS cells and neural plate explant is shown by the dotted line.

Scale bar is 60 µm.

FIG. 5J

Induction of Floor Plate differentiation in neural plant explants by Vhh-1. Neural plate explants grown in contact with COS cells transfected with cDNA encoding antisense Vhh-1 and labeled with anti-FP3 antibodies. The FP3 antigen is not expressed.

Scale bar is 60 µm.

FIG. 5K

Induction of Floor Plate differentiation in neural plant explants by Vhh-1. Neural plate explants grown in contact with COS cells transfected with cDNA encoding antisense Vhh-1 and labeled with anti-FP4 antibodies. The FP4 antigen is not expressed.

Scale bar is 60 µm.

FIG. 6A

Induction of Motor Neuron Differentiation in Neural Explants by Vhh-1. Section through a stage 17 chick spinal cord showing the expression of Islet-1$^+$ motor neurons in ventral spinal cord. Islet-1$^+$ cells are also detected in dorsal root ganglion neurons located next to the spinal cord.

Scale bar is 70 µm.

FIG. 6B

Induction of Motor Neuron Differentiation in Neural Explants by Vhh-1. Phase-contrast micrographs explants grown for 44 hours on a monolayer of COS cells transfected with cDNA encoding sense Vhh-1. The field shows three explants containing Islet-1$^+$ cells. COS cells nuclei (COS) visible under the neural plate explants. The border between the neural plate explants and COS cell monolayer is shown.

Scale bar is 70 µm.

FIG. 6C

Induction of Motor Neuron Differentiation in Neural Explants by Vhh-1. Florescence micrographs explants grown for 44 hours on a monolayer of COS cells transfected with cDNA encoding sense Vhh-1. The field shows three explants containing Islet-1$^+$ cells. COS cells nuclei (COS) visible under the neural plate explants. The border between the neural plate explants and COS cell monolayer is shown.

Scale bar is 70 µm.

FIG. 6D

Induction of Motor Neuron Differentiation in Neural Explants by Vhh-1. Section through a stage 17 chick spinal cord showing the distribution of SC1 in floor plate cells (f), motor neurons (m), and notochord (n) Scale bar is 70 µm.

FIG. 6E

Figure 5A:
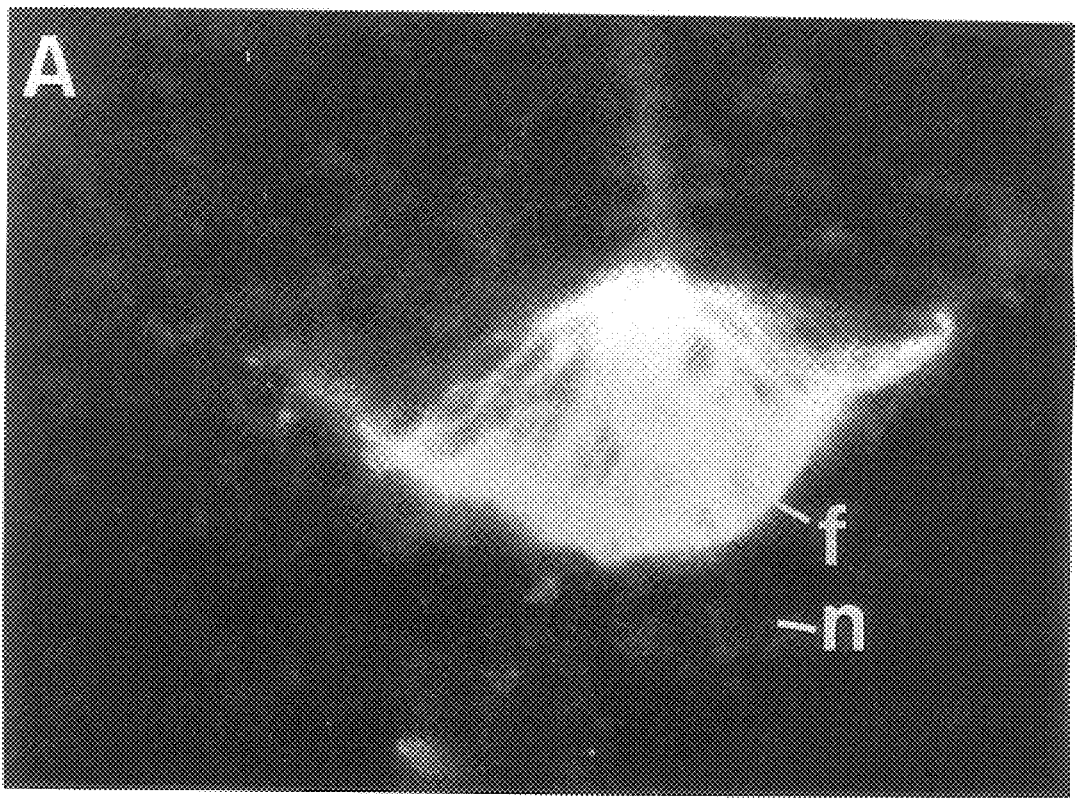
Figure 5B:
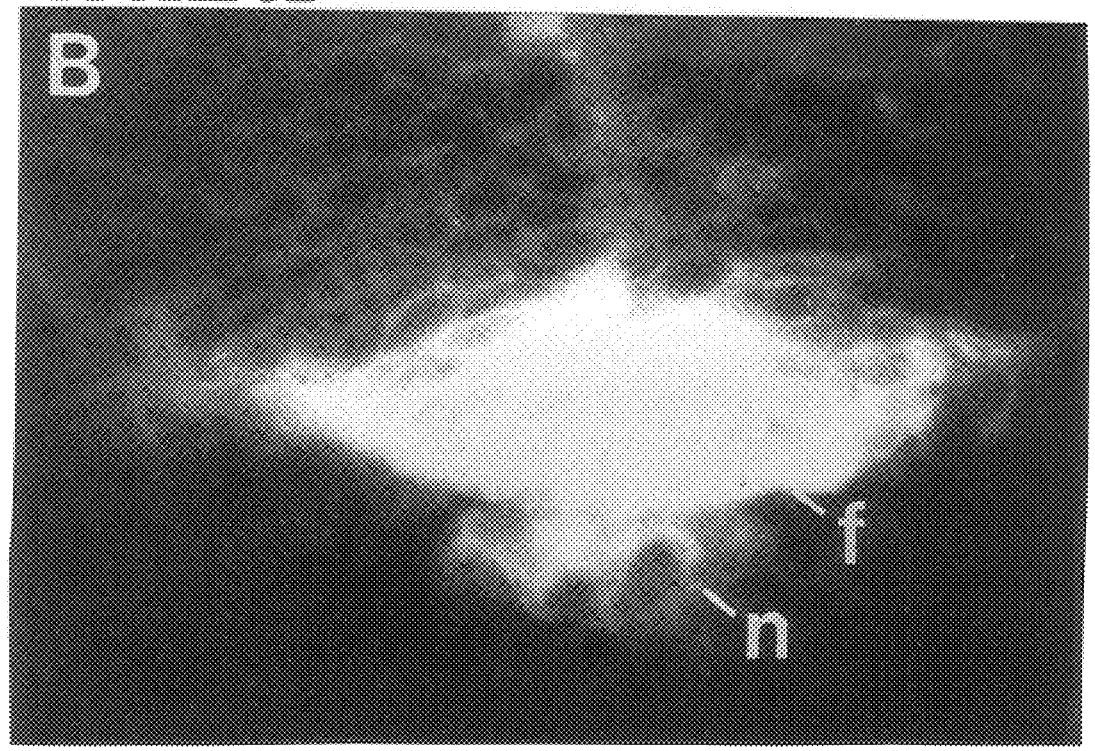
Figure 5C:
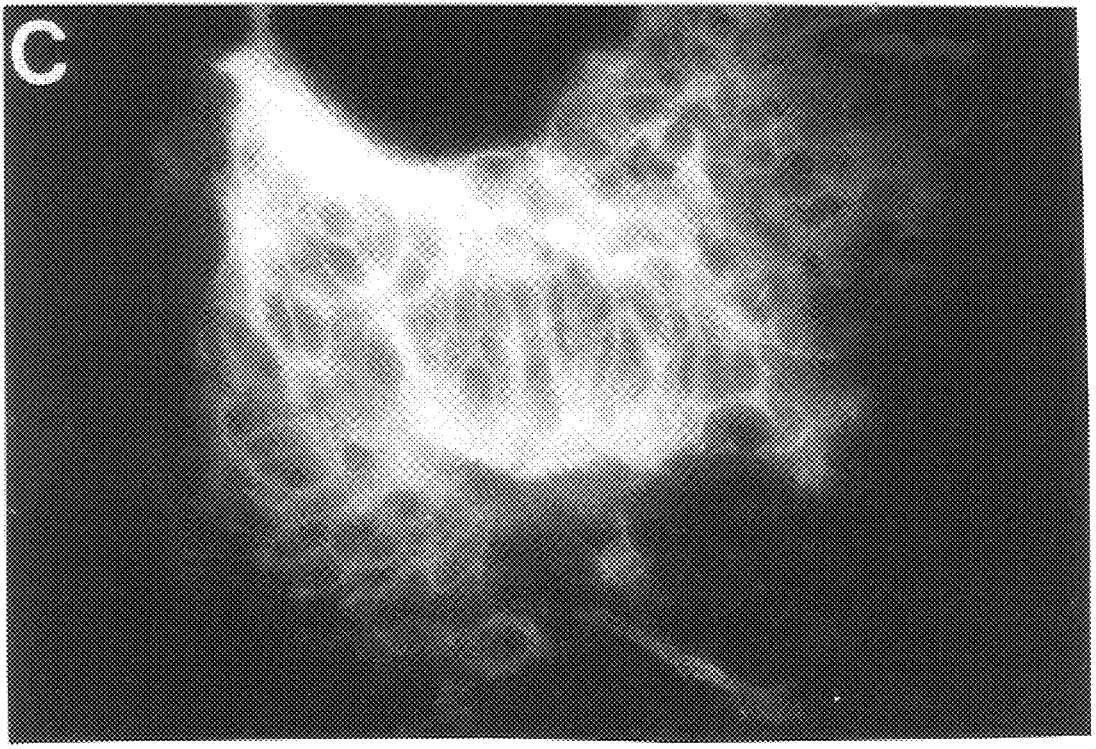
Figure 5D:
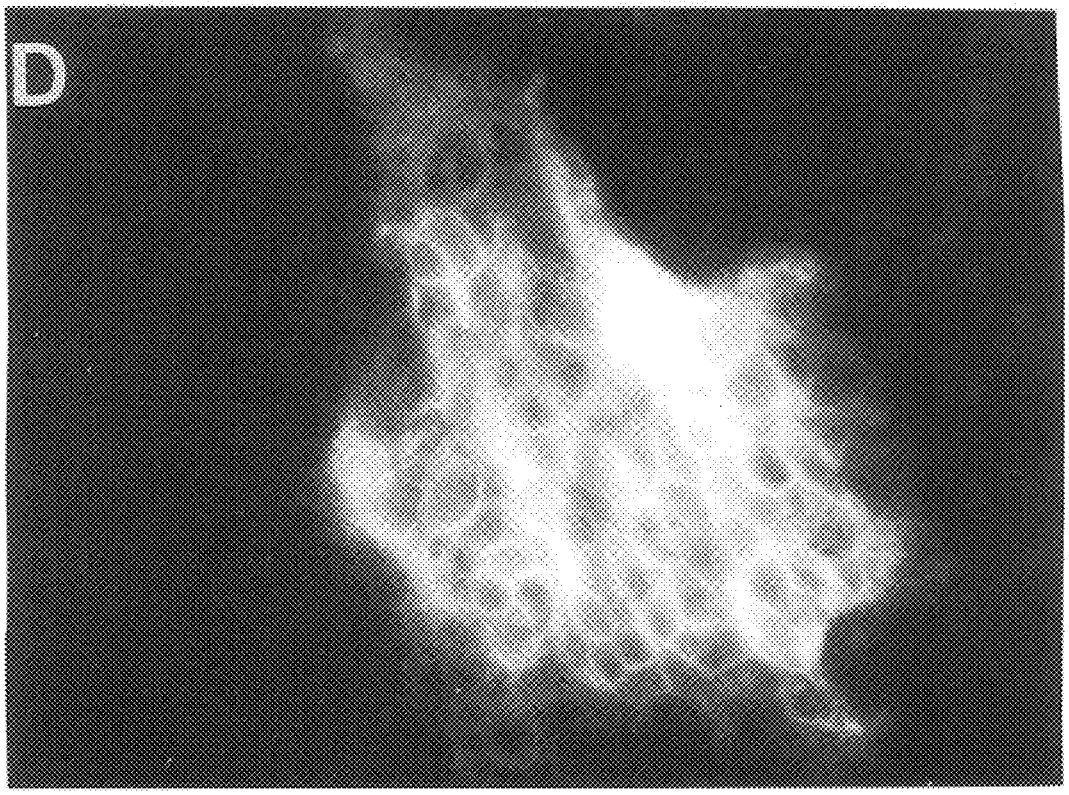
Figure 5E:
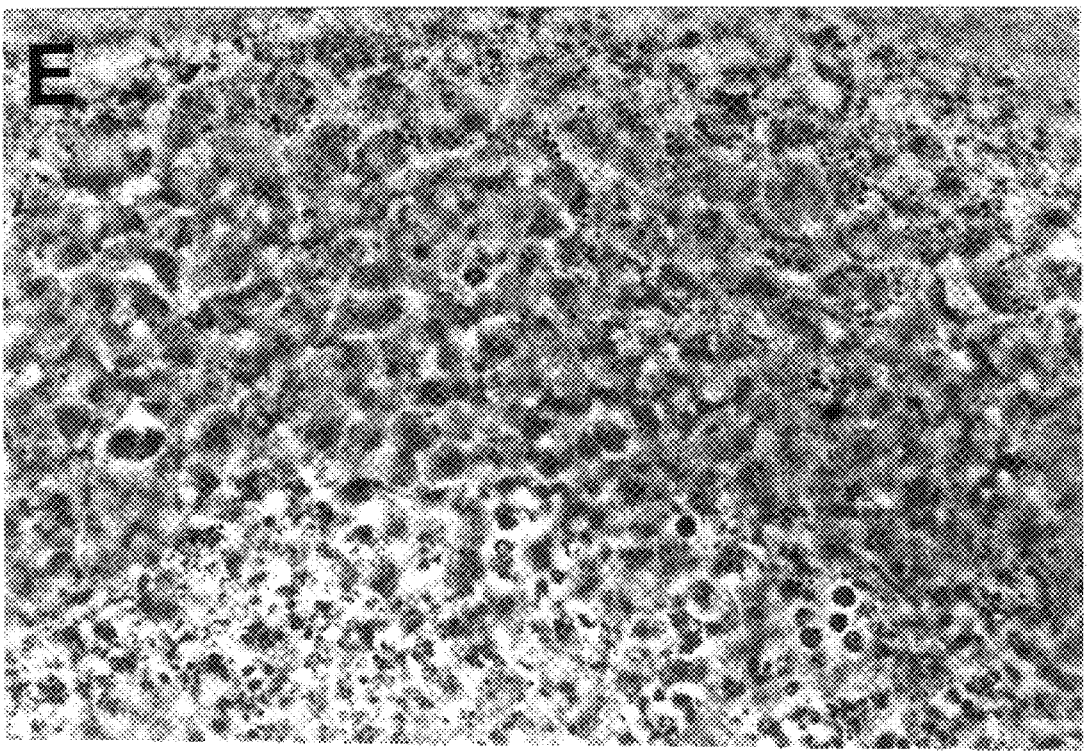
Figure 5F:
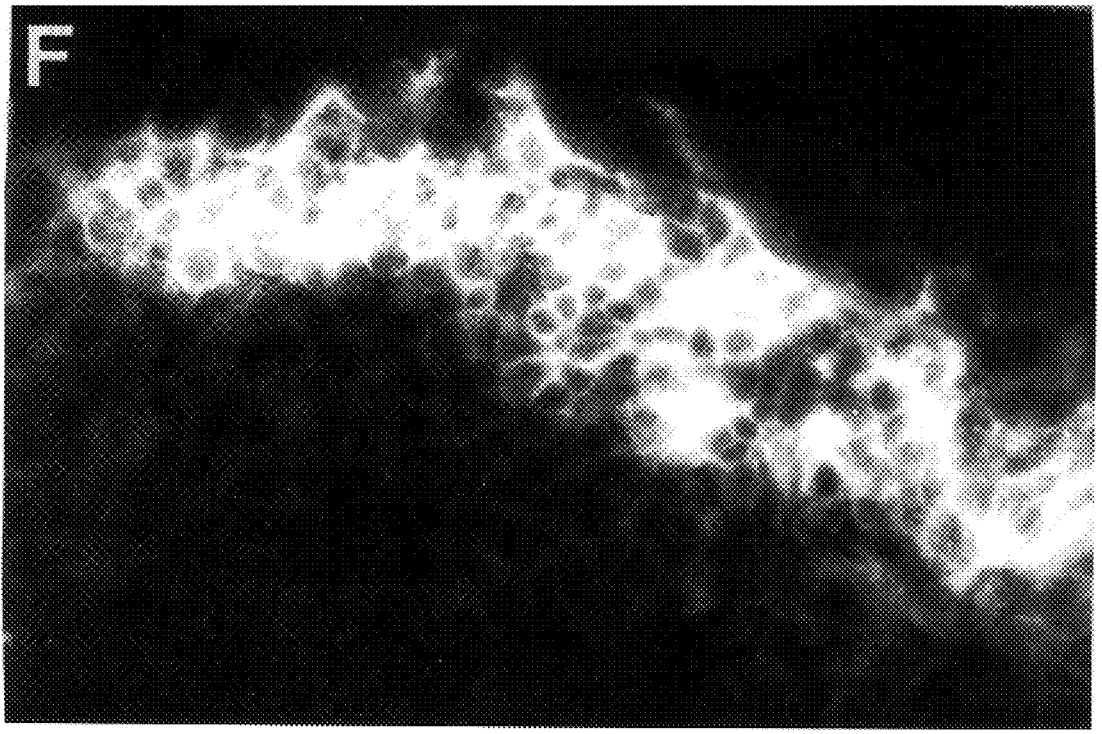
Figure 5G:
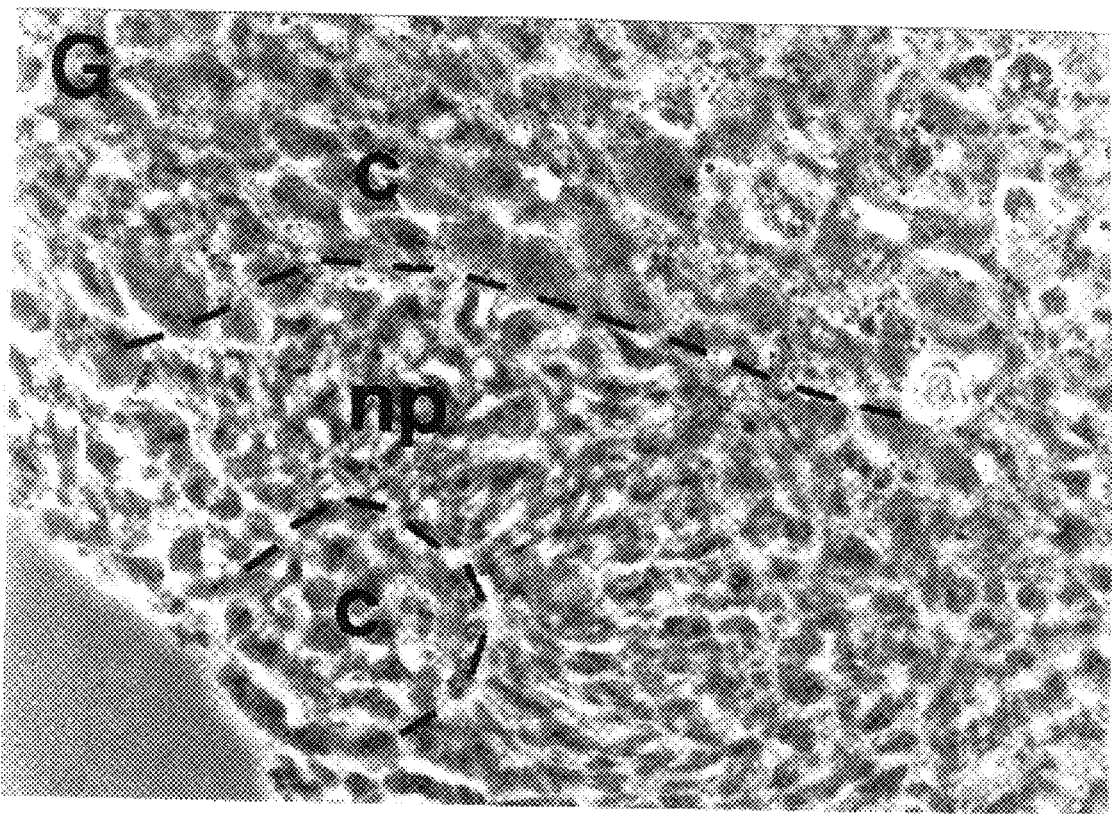
Figure 5H:
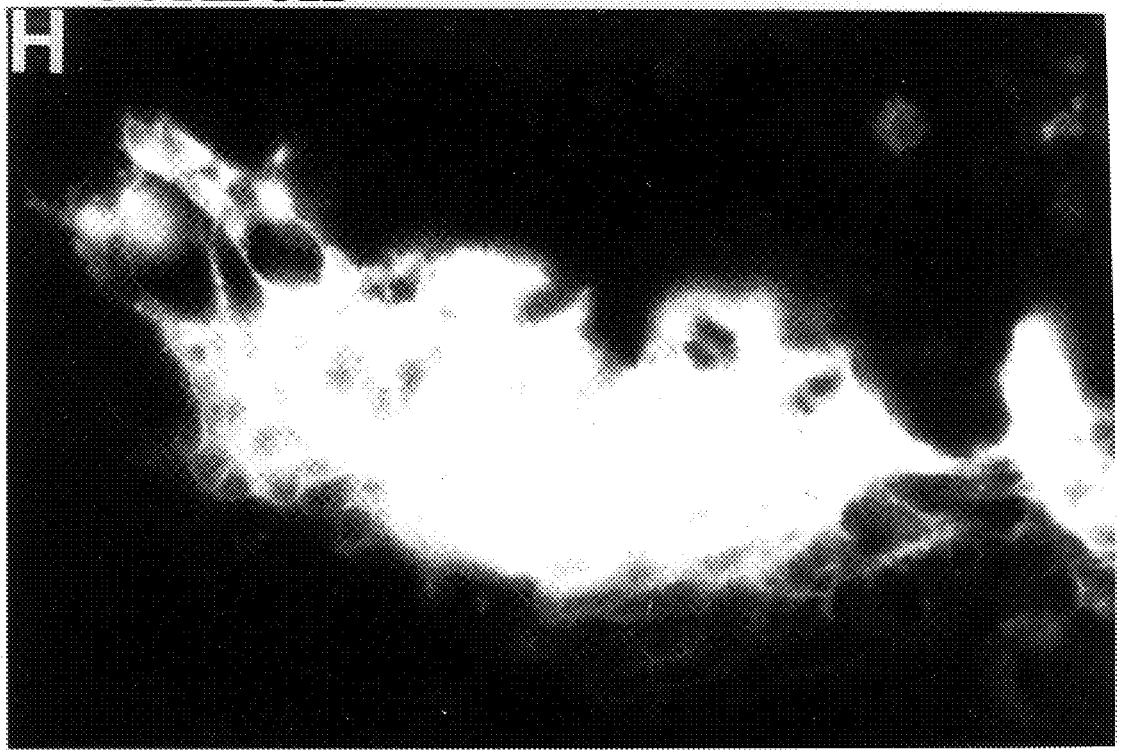

Induction of Motor Neuron Differentiation in Neural Explants by Vhh-1. Confocal image of a single field in a chick neural plate explant grown 44 hours on COS cells transfected with the Vhh-1 gene and labelled with antibodies against SC1. All SC1$^+$ cells express Islet-1 in their nuclei (Compare with FIG. 5F). Clusters of SC1$^+$/Islet-1 cells were not detected in these explants (data not shown).

Scale bar is 13 µm.

FIG. 6F

Induction of Motor Neuron Differentiation in Neural Explants by Vhh-1. Confocal image of a single field in a chick neural plate explant grown 44 hours on COS cells transfected with the Vhh-1 gene and labelled with antibodies against Islet-1.

Scale bar is 13 µm.

FIG. 6G

Neural plate explants grown for 48 hours on a monolayer of COS cells transfected with a gene encoding antisense Vhh-1 and labelled with anti-Islet-1 antibodies. No expression of Islet-1 is detected.

Scale bar is 70 µm.

FIG. 6G

Neural plate explants grown for 48 hours on a monolayer of COS cells transfected with a gene encoding antisense Vhh-1 and labelled with anti-SC1 antibodies. No expression of SC1 is detected. This image is of a confocal section through an explant.

Scale bar is 13 µm.

FIG. 7A

Cells in Posterior Limb Bud Mesenchyme Express mRNA Encoding Vhh-1 and Can Enduce Floor Plate Differentiation in Neural Plate Explants. Section through limb bud of an E11 rat embryo showing expression of mRNA encoding Vhh-1 in mesenchymal cells located in the posterior (p) region of the limb bud. Mesenchymal cells in the anterior (a) region of the cell do not express mRNA encoding Vhh-1. Ectodermal cells do not express Vhh-1 mRNA.

Scale bar is 270 µm.

FIG. 7B

Cells in Posterior Limb Bud Mesenchyme Express mRNA Encoding Vhh-1 and Can Enduce Floor Plate Differentiation in Neural Plate Explants. Phase-contrast micrograph showing expression of FP3 by neural plate cells grown in contact with chick posterior limb mesenchyme. Neural plate cells express FP3.

Scale bar is 60 µm.

FIG. 7C

Cells in Posterior Limb Bud Mesenchyme Express mRNA Encoding Vhh-1 and Can Enduce Floor Plate Differentiation in Neural Plate Explants. Fluorescence micrograph showing expression of FP3 by neural plate cells grown in contact with chick posterior limb mesenchyme. Neural plate cells express FP3.

Scale bar is 60 µm.

FIG. 7D

Induction of Motor Neuron Differentiation in Neural Explants by Vhh-1. Phase-contrast micrograph of neural plate explants grown in contact with anterior limb bud mesenchyme. No expression of FP3 is detected.

Scale bar is 60 μm.

FIG. 7E

Induction of Motor Neuron Differentiation in Neural Explants by Vhh-1. Fluorescence micrograph of neural plate explants grown in contact with anterior limb bud mesenchyme. No expression of FP3 is detected.

Scale bar is 60 μm.

DETAILED DESCRIPTION OF THE INVENTION

This invention provides an isolated nucleic acid molecule encoding a vertebrate Vhh-1 protein. As used herein, the term "isolated nucleic acid molecule" means a non-naturally occurring nucleic acid molecule that is, a molecule which does not occur in nature. As used herein, "Vhh-1 protein" means a molecule which has the same or substantially the same amino acid sequence as described in FIGS. 1-1, 1-2 and 1-3 (Seq.I.D. 2). Examples of such an isolated nucleic acid molecule are isolated cDNA or genomic DNA molecules encoding a vertebrate Vhh-1 protein. This invention provides an isolated nucleic acid molecule encoding a vertebrate Vhh-1 protein wherein the nucleic acid molecule is a DNA molecule. This invention further provides an isolated DNA molecule encoding a vertebrate Vhh-1 protein, wherein the DNA molecule is a cDNA molecule.

A prefered embodiment of a nucleic acid encoding a vertebrate Vhh-1 protein is a nucleic acid molecule encoding the rat Vhh-1 protein. This invention provides an isolated nucleic acid molecule encoding a vertebrate Vhh-1 molecule, wherein the isolated nucleic acid molecule encodes the rat Vhh-1 protein. Such a molecule may have coding sequences the same or substantially the same as the coding sequences shown in FIGS. 1-1, 1-2 and 1-3 (Seq I.D. No. 1).

This invention provides an isolated nucleic acid molecule encoding the rat Vhh-1 protein, wherein the nucleic acid molecule is DNA. This invention further provides an isolated DNA molecule encoding the rat Vhh-1 protein, wherein the DNA molecule is cDNA. An example the nucleotide sequence of a cDNA molecule encoding a rat Vhh-1 protein is provided in FIGS. 1-1, 1-2 and 1-3 (Sequence I.D. No. 1).

Another preferred embodiment of an isolated nucleic acid molecule encoding a vertebrate Vhh-1 protein is a nucleic acid molecule encoding the human Vhh-1 protein. This invention provides an isolated nucleic acid molecule encoding a vertebrate Vhh-1 protein, wherein the isolated nucleic acid molecule encodes a human Vhh-1 protein.

This invention further provides an isolated nucleic acid molecule encoding the human Vhh-1 protein, wherein the nucleic acid molecule is DNA.

One means of isolating a vertebrate Vhh-1 protein is to probe a mammalian genomic library with a natural or artificially designed DNA probe, using methods well known in the art. In one embodiment of this invention, the rat Vhh-1 protein and the nucleic acid molecules encoding them are isolated from a rat cDNA library. DNA and cDNA molecules which encode rat Vhh-1 protein are used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained. The human homolog of the rat Vhh-1 gene is isolated using the rat Vhh-1 probe described hereinabove and cloning techniques known to one of skill in the art, such as homology screening of genomic or cDNA libraries or PCR amplification techniques. The vhh-1 gene is expressed in the lungs of older embryos, therefore the preferred method of cloning the human Vhh-1 gene involves screening the clontech human fetal lung cDNA library to obtain the human clone. The rat Vhh-1 has been used to identify the chick and frog vhh-1 genes (data not shown) and will therefore be sufficiently conserved to identify the human vhh-1 gene.

This invention provides a vector comprising a nucleic acid molecule encoding a vertebrate Vhh-1 protein. Examples of vectors are viruses such as bacteriophages (including but not limited to phage lambda), animal viruses (including but not limited to baculovirus, vaccinia virus, Herpes virus and Murine Leukemia virus), cosmids, plasmids, and other recombination vectors are well known in the art. Nucleic acid molecules are inserted into vector genomes by methods well known to those skilled in the art. To obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also known to one of skill in the art.

This invention provides a plasmid comprising the vector comprising an isolated nucleic acid molecule encoding a vertebrate Vhh-1 protein. Examples of such plasmids are plasmids comprising cDNA having a coding sequence the same or substantially the same as the coding sequence shown in FIGS. 1-1, 1-2 and 1-3 (Seq. I.D. No. 1) and are designated clone pMT21 2hh #7 deposited under ATCC Accession No. 75686 and designated clone cmv vhh #7 deposited under ATCC Accession No. 75685. This invention provides the plasmid comprising the vector comprising an isolated nucleic acid molecule encoding a vertebrate Vhh-1 protein, which is designated pMT21 2hh #7 (ATCC Accession No. 75686).

This invention further provides an expression plasmid comprising a nucleic acid molecule encoding a vertebrate Vhh-1 protein. An example of one such plasmid is the expression plasmid encoding a rat Vhh-1 protein, which is designated cmv vhh #7 (ATCC Accession No. 75685), and this invention provides the expression plasmid comprising the cDNA molecule encoding a rat Vhh-1 protein, which is designated cmv vhh #7 (ATCC Accession No. 75685).

Expression vectors can be adapted for expression in a bacterial cell, a yeast cell, an insect cell, a Xenopus oocyte or a mammalian cell which additionally are operatively linked to regulatory elements necessary for expression of the inserted gene in the bacterial, yeast, insect, frog or mammalian cells. DNA having coding sequences substantially the same as the coding sequence shown in FIGS. 1-1, 1-2 and 1-3 can be inserted into the vectors for expression using the methods discussed hereinabove or other methods known to one of skill in the art. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome operatively linked to the recombinant gene. Furthermore, an insect expression vector such as baculovirus AcMNPV uses the strong viral expression signals for the virus' polyhedrin gene to drive transcription of the recombinant gene. One such example of a plasmid comprising regulatory elements for expression in oocytes operatively linked to the recombinant vhh-1 gene is the plasmid designated cmv vhh #7 and deposited under ATCC Accession No. 75685. Such vectors may be obtained commercially or assembled from the sequences described by methods well known in the art, for example the methods described above for constructing vectors in general. Expression vectors are useful to produce cells that express the Vhh-1 protein. Certain uses for such cells are described in more detail below.

Deposits were made on February 24, 1994 of both the pMT21 2hh #7 and cmv vhh #7 plasmids with the American Type Culture Collection (ATCC), 12301 Parklawn Drive, Rockville, Md. 20852. The two deposits were made pursuant to, and in satisfaction of, the provisions of the Budapest Treaty on the International Recognition of the Deposit of Microorganisms for the Purpose of Patent Procedure with the ATTC. This invention provides a mammalian cell comprising an expression plasmid encoding a vertebrate Vhh-1 protein.

This invention further provides a Cos cell comprising an expression plasmid encoding a vertebrate Vhh-1 protein.

Numerous mammalian cells may be used as hosts, including, but not limited to, the mouse fibroblast cell NIH3T3, CHO cells, HeLa cells, Cos cells, and 293 cells. Expression plasmids such as that described supra may be used to transfect mammalian cells by methods well known in the art such as calcium phosphate precipitation, or DNA encoding the Vhh-1 protein may be otherwise introduced into mammalian cells, e.g., by microinjection, to obtain mammalian cells which comprise DNA, e.g., cDNA or a plasmid, encoding a vertebrate Vhh-1 protein.

This invention provides a nucleic acid molecule probe comprising a nucleic acid molecule of at least 15 nucleotides capable of specifically hybridizing with a unique sequence included within the sequence of a nucleic acid molecule comprising the gene encoding the vertebrate Vhh-1 protein and its noncoding 3' and 5' nucleotides as shown in FIGS. 1-1, 1-2 and 1-3.

As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the vertebrate Vhh-1 protein. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid molecules encoding vertebrate Vhh-1 protein is useful as a diagnostic test for any disease process in which levels of expression of the corresponding Vhh-1 protein is altered. DNA probe molecules are produced by insertion of a DNA molecule which encodes vertebrate Vhh-1 protein or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1-1, 1-2 and 1-3. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a vertebrate Vhh-1 protein are useful as probes for this gene, for its associated mRNA, or for the isolation of related genes by homology screening of genomic or cDNA libraries, or by the use of amplification techniques such as the Polymerase Chain Reaction.

A preferred embodiment of a nucleic acid molecule probe of a vertebrate Vhh-1 protein is a DNA molecule probe. This invention further a DNA molecule probe comprising a DNA molecule of at least 15 nucleotides capable of specifically hybridizing with a unique sequence included within the sequence of a DNA molecule comprising the gene encoding the vertebrate Vhh-1 protein and its noncoding 3' and 5' nucleotides as shown in FIGS. 1-1, 1-2 and 1-3.

This invention provides a purified vertebrate Vhh-1 protein.

This invention further provides a purified unique polypeptide fragment of the vertebrate Vhh-1 protein.

As used herein, the term "unique polypeptide fragment" encompasses any polypeptide with the same amino acid sequence as any unique amino acid sequence as shown in FIGS. 1-1, 1-2 and 1-3 (Sequence ID No. 2). One means for obtaining an isolated polypeptide fragment of a vertebrate Vhh-1 protein is to treat isolated Vhh-1 protein with commercially available peptidases and then separate the polypeptide fragments using methods well known to those skilled in the art. Polypeptide fragments are often useful as antigens used to induce an immune response and subsequently generate antibodies against the polypeptide fragment and possibly the whole polypeptide which in this case is the vertebrate Vhh-1 protein.

This invention provides a purified vertebrate Vhh-1 protein, wherein the purified vertebrate Vhh-1 protein is a rat Vhh-1 protein.

The rat Vhh-1 protein has an amino acid sequence the same or substantially similar to the amino acid sequence shown in FIGS. 1-1, 1-2 and 1-3 (Seq. I.D. Nos. 2). As used herein, the term "purified protein" is intended to encompass a protein molecule free of other cellular components. One means for obtaining isolated rat Vhh-1 protein is to express DNA encoding the rat Vhh-1 protein in a suitable host, such as a bacterial, yeast, insect, or mammalian cell, using methods well known to those skilled in the art, and recovering the rat Vhh-1 protein after it has been expressed in such a host, again using methods well known in the art. The Vhh-1 protein may also be isolated from cells which express the rat Vhh-1 protein, in particular from cells which have been transfected with the expression vectors described below in more detail.

This invention further provides a purified vertebrate Vhh-1 protein, wherein the purified vertebrate Vhh-1 protein is a human Vhh-1 protein.

One means for obtaining purified human Vhh-1 protein is to express DNA encoding the human Vhh-1 protein in a suitable host, such as a bacterial, yeast, insect, or mammalian cell, using methods well known to those skilled in the art, and recovering the Vhh-1 protein after it has been expressed in such a host, again using methods well known in the art. The human Vhh-1 protein may also be isolated from cells which express it, in particular from cells which have been transfected with the expression vectors described below in more detail.

This invention provides a monoclonal antibody directed to a vertebrate Vhh-1 protein.

This invention further provides a monoclonal antibody, directed to an epitope of a vertebrate Vhh-1 protein and having an amino acid sequence substantially the same as an amino acid sequence for an epitope of a vertebrate Vhh-1 protein.

This invention further provides a monoclonal antibody, wherein the monoclonal antibody is directed to the rat Vhh-1 protein.

This invention further provides a monoclonal antibody, wherein the monoclonal antibody is directed to the human Vhh-1 protein.

Monoclonal antibody directed to a vertebrate Vhh-1 protein may comprise, for example, a monoclonal antibody directed to an epitope of a vertebrate Vhh-1 protein present on the surface of a cell, the epitope having an amino acid sequence substantially the same as an amino acid sequence for a cell surface epitope of the vertebrate Vhh-1 protein included in the amino acid sequence shown in FIGS. 1-1, 1-2 and 1-3. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1-1, 1-2 and 1-3 will bind to a surface epitope of a vertebrate Vhh-1 protein, as described. Antibodies directed to vertebrate Vhh-1 protein may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or 293 cells may be used as immunogens to raise such an antibody. Alternatively, synthetic peptides may be prepared using commercially available machines and the amino acid sequences shown in FIGS. 1-1, 1-2 and 1-3. As a still further alternative, DNA, such as a cDNA or a fragment thereof, may be cloned and expressed and the resulting polypeptide recovered and used as an immunogen. These antibodies are useful to detect the presence of vertebrate Vhh-1 encoded by the isolated DNA, or to inhibit the function of the Vhh-1 protein in living animals, in humans, or in biological tissues or fluids isolated from animals or humans.

This invention provides polyclonal antibodies directed to a vertebrate Vhh-1 protein.

Animal model systems which elucidate the physiological and behavioral roles of vertebrate Vhh-1 protein are produced by creating transgenic animals in which the expression of a Vhh-1 protein is either increased or decreased, or the amino acid sequence of the expressed Vhh-1 protein is altered, by a variety of techniques. Examples of these techniques include, but are not limited to: 1) Insertion of normal or mutant versions of DNA encoding a rat Vhh-1 or homologous animal versions of these genes, especially the human homolog of the Vhh-1 gene, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)) or, 2) Homologous recombination (Capecchi M. R. Science 244:1288–1292 (1989); Zimmer, A. and Gruss, P. Nature 338:150–153 (1989)) of mutant or normal, human or animal versions of these genes with the native gene locus in transgenic animals to alter the regulation of expression or the structure of these Vhh-1 proteins. The technique of homologous recombination is well known in the art. It replaces the native gene with the inserted gene and so is useful for producing an animal that cannot express native gene encoding the Vhh-1 protein but does express, for example, an inserted mutant gene encoding a mutant Vhh-1 protein, which has replaced the native Vhh-1 gene in the animal's genome by recombination, resulting in underexpression of the Vhh-1 protein. Microinjection adds genes to the genome, but does not remove them, and so is useful for producing an animal which expresses its own and added Vhh-1 protein, resulting in overexpression of the Vhh-1 protein. This invention provides a transgenic nonhuman mammal which comprises an isolated DNA molecule encoding a vertebrate Vhh-1 protein.

One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a vertebrate Vhh-1 protein is purified from a vector (such as plasmid pMT21 2hh #7 described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of Vhh-1 protein-specific drugs is to mimic, activate or inhibit the Vhh-1 protein, the transgenic animal model systems described above are useful for testing the biological activity of drugs directed to mimic or alter the Vhh-1 protein activity even before such drugs become available. These animal model systems are useful for predicting or evaluating possible therapeutic applications of drugs which mimic, activate or inhibit the vertebrate Vhh-1 protein by alleviating abnormalities observed in the transgenic animals associated with decreased or increased expression of the native Vhh-1 gene or vhh-1 transgene. Thus, a model system is produced in which the biological activity of drugs specific for the Vhh-1 protein are evaluated before such drugs become available. The transgenic animals which over or under produce the Vhh-1 protein indicate by their physiological state whether over or under production of the Vhh-1 protein is therapeutically useful. It is therefore useful to evaluate drug action based on the transgenic model system. Therefore, an animal which underexpresses Vhh-1 protein is useful as a test system to investigate whether the actions of a pharmaceutical compound comprising Vhh-1 is in fact therapeutic. Another use is that if overexpression is found to lead to abnormalities, then a drug which acts as an antagonist to the Vhh-1 protein is indicated as worth developing, and if a promising therapeutic application is uncovered by these animal model systems, activation or inhibition of the Vhh-1 protein is achieved therapeutically either by producing agonist or antagonist drugs directed against the vertebrate Vhh-1 protein or by any method which increases or decreases the activity of the Vhh-1 protein.

This invention provides a transgenic nonhuman mammal which comprises an isolated DNA molecule encoding a rat Vhh-1 protein.

This invention further provides the transgenic nonhuman mammal which comprises an isolated DNA molecule encoding a vertebrate Vhh-1 protein, wherein the DNA encoding a vertebrate Vhh-1 protein additionally comprises tissue specific regulatory elements.

This invention provides a transgenic nonhuman mammal which comprises the isolated DNA molecule encoding a human Vhh-1 protein.

This invention provides a method of determining the physiological effects of expressing varying levels of a vertebrate Vhh-1 protein which comprises producing a panel of transgenic nonhuman animals each expressing a different amount of vertebrate Vhh-1 protein. Such animals may be produced by introducing different amounts of DNA encoding a rat Vhh-1 protein into the oocytes from which the transgenic animals are developed.

This invention provides a method of preparing a purified vertebrate Vhh-1 protein which comprises: (a) inserting a nucleic acid molecule encoding a vertebrate Vhh-1 protein in a suitable vector; (b) inserting the resulting vector in a suitable host cell; (c) recovering the vertebrate Vhh-1 protein produced by the resulting cell; and (d) purifying the vertebrate Vhh-1 protein so recovered.

This invention provides a method of preparing the purified rat Vhh-1 protein which comprises: (a) inserting a nucleic acid encoding the rat Vhh-1 protein in a suitable vector; (c) inserting the resulting vector in a suitable host cell; (d) recovering the Vhh-1 protein produced by the resulting cell; and (d) purifying the rat Vhh-1 protein so recovered.

This invention provides a method of preparing the purified human Vhh-1 protein which comprises: (a) inserting nucleic acid encoding the human Vhh-1 protein in a suitable vector; (b) inserting the resulting vector in a suitable host cell; (c) recovering the human Vhh-1 protein produced by the resulting cell; and (d) purifying the human Vhh-1 protein so recovered.

These methods for preparing vertebrate Vhh-1 protein involve methods well known in the art. For example, an isolated nucleic acid molecule encoding a vertebrate Vhh-1 protein is inserted in a suitable vector, such as an expression vector. A suitable host cell, such as a bacterial cell, or a eukaryotic cell such as a yeast cell, or an insect cell is transfected with the vector. The vertebrate protein is isolated from the culture medium by affinity purification or by chromatography or by other methods well known in the art.

This invention provides a pharmaceutical composition comprising an effective amount of a human Vhh-1 protein and a pharmaceutically acceptable carrier.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit. Delivery of pharmaceutical compositions to sites of Vhh-1 protein action propose a complex problem. Vhh-1 induces nondifferentiated motor neuron precursor cells to differentiate into motor neurons. Since the regeneration of motor neurons for the purpose of alleviating abnormalities associated with acute nervous system injury or chronic neurodegenerative diseases requires differentiation of motor neuron precursor cells which reside in the central nervous system (CNS), pharmaceutical compounds comprising the Vhh-1 protein or drugs or substances that alter Vhh-1 protein action must be delivered into the CNS. Vhh-1 does not pass through the blood-brain barrier and therefore pharmaceutical compositions comprising same must be given intra cerebrally, surgically implanted within the CNS, or complexed to a carrier molecule (such as transferrin) capable of crossing the blood-brain barrier. A neurotrophic factor, NGF, has been chronically infused into the brain by a mechanical pump device which allow consistent delivery of NGF into the CNS (Koliatos et al. 1991 and Olsen et al. 1992). In the case of acute nervous system injury involving specific central axon (s), slow release implants containing Vhh-1 in a known biodegradable polymer matrix could be surgically implanted at the site of the injured axon(s) effective to regenerate motor neurons from motor neuron precursor cells proximal to the injured axon. Another neurotrophic factor, NGF, has successfully been implanted in such a manner to prevent degeneration of cholinergic neurons (Hoffman et al. 1990 and Maysinger et al. 1992). Another method of implanting a source of Vhh-1 next to an injured axon requires the transfection of cells incapable of proliferation and further encapsulated to avoid infiltration of the CNS wherein such cells comprise a plasmid encoding the human Vhh-1 gene and therefore express Vhh-1. Aebischer et al. (1991) successfully implanted encapsulated growth factor producing cells to avoid infiltration of brain tissue. Neurotrophic factors have successfully been conjugated to carrier molecules that shuttle the factor into the CNS. One such example is NGF which has been conjugated to a carrier molecule, monoclonal anti-transferrin receptor antibodies, effective to deliver the neurotrophic factor into the CNS (Friden et al. 1993).

This invention provides a method for treating a human subject afflicted with an abnormality associated with the lack of one or more normally functioning motor neuron(s) which comprises introducing an amount of a pharmaceutical composition comprising an amount of a human Vhh-1 protein and a pharmaceutically acceptable carrier effective to generate motor neurons from undifferentiated motor neuron precursor cells in a human, thereby treating a human subject afflicted with an abnormality associated with a lack of one or more normally functioning motor neuron(s).

This invention provides a method of treating a human subject afflicted with a neurodegenerative disease which comprises introducing an amount of a pharmaceutical composition comprising an amount of a human Vhh-1 protein and a pharmaceutically acceptable carrier effective to generate motor neurons from undifferentiated motor neuron precursor cells in a human, thereby treating a human subject afflicted with a neurodegenerative disease.

This invention provides a method of treating a human subject afflicted with a neurodegenerative disease, wherein the chronic neurodegenerative disease is Amyotrophic lateral sclerosis (ALS), which comprises introducing an amount of a pharmaceutical composition comprising an amount of a human Vhh-1 protein and a pharmaceutically acceptable carrier effective to generate motor neurons from undifferentiated motor neuron precursor cells in a human, thereby treating a human subject afflicted with Amyotrophic lateral sclerosis (ALS).

A method of treating a human subject afflicted with an acute nervous system injury which comprises introducing an amount of a pharmaceutical composition comprising an amount of a human Vhh-1 protein and a pharmaceutically acceptable carrier effective to generate motor neurons from undifferentiated motor neuron precursor cells in a human, thereby treating a human subject afflicted with an acute nervous system injury.

A method of treating a human subject afflicted with an acute nervous system injury, wherein an acute nervous system injury is localized to a specific central axon which comprises surgical implantation of an amount of a pharmaceutical composition comprising the human Vhh-1 protein and a pharmaceutically acceptable carrier effective to generate motor neurons from undifferentiated motor neuron precursor cells located proximal to the injured axon in a human, thereby alleviating an acute nervous system injury localized to a specific central axon.

Elucidation of the molecular structures of the neurotrophic factor designated as the Vhh-1 protein is an important step in the understanding of new neurotrophic factors. This disclosure reports the isolation, amino acid sequence, and functional expression of a cDNA clone from rat brain which encodes a Vhh-1 protein. Analysis of the rat Vhh-1 protein structure and function provides a possible model for the development of drugs useful for the treatment of acute nervous system injury or chronic neurodegenerative diseases such as amyotrophic lateral sclerosis (ALS).

Specifically, this invention relates to the first isolation of a cDNA clone encoding a rat Vhh-1 protein. The vertebrate vhh-1 gene is expressed in restricted regions of the embryo, in particular the notochord and floor plate, two cell groups which have been shown to induce ventral cell types including the floor plate and motor neurons. The vertebrate gene for this Vhh-1 protein has been characterized in vivo and in vitro to elucidate the role of Vhh-1 in inducing the developmental differentiation of motor neurons and floor plate in embryos. The Vhh-1 protein is likely to be useful in the treatment of degenerative disorders of the central nervous system, in particular motor neuron degeneration, and this may be useful in the treatment of a number of clinical disorders that result in motor dysfunction. In addition, the rat Vhh-1 protein has been expressed in COS cells by transfecting the cells with a plasmid comprising the rat Vhh-1 protein.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Experimental Details

Animals

Zebrafish embryos were obtained from the colony at the Department of Microbiology, Umea University, Sweden, Pregnant female rats (Hilltop) were delivered by Caesarean section and embryos staged according to somite number. Fertile white leghorn chicken eggs were obtained from SPAFAS, Incorporated (Norwich, Conn.). chick embryos were staged according to Hamburger and Hamilton (1951). Frog (*Xenopus laovis*) eggs and embryos were reared and staged according to Nieuwkoop and Faber (1957) and Ruiz l Altaba (1993).

Isolation of Vertebrate Genes Related to hh

Plaques ($10^4$) of a 9–16 hr. postfertilization λZAPII zebrafish library were screened at low stringency with Drosophila hh cDNA (provided by J. Mohler) and with DNA fragments generated by polymerase chain reaction using the hh sequence (lee et al., 1992) as a template. Two sets of polymerase chain reaction primers were used 5'-GAGGATTGGGTCGTCATAGG-3' (SEQ ID NO:3) (positions β52–β71 in the Drosophila hh cDNA) and 5'-CTTCAAGGATTCCATCTCAA-3' (SEQ ID NO:4) (positions 1799–1818); 5'AGCTGGGACGAGGACTACCATC-3' (SEQ ID NO:5) (positions 945–966) and 5'TGGGAACTGATCGACGAATCTG-3' (SEQ ID NO:6) (positions 1147–1128). Clones isolated with the second primer set were subcloned and sequenced on both strands by the dideoxy chain termination method (Sanger et al., 1977). DNA and derived amino acid sequences were analyzed on a VAX computer using the Genus software package.

To identify rat hh-related cDNA clones, approximately $2.5\times10^5$ colonies of a rat E13 floor plague cDNA library in pMT21 were screened with the zebrafish Vhh-1 probe in HM mix (5×Denhardt's solution. 10% dextran sulphate, 2×SSC, 2×SSPE, 0.5% SDS, and 50 µg/ml denatured herring sperm DNA) at 60% C XhoI cDNA inserts from hybridizing clones were subcloned in pBluscript II KS(-) and sequenced on both strands by the dideoxy chain termination methods (Sanger et al., 1977). Sequence analysis and compilations were performed on a VAX computer using GCG software.

In Situ Hybridization

Whole-mount in situ hybridization analysis of mRNA expression were performed with digoxigenin-labeled probes essentially as described by Harland (1991) and Krauss et al. (!1991) with minor modifications (Ruiz l Altaba et al., 1993b) and for cryostat sections as described by Schaeren-Wiemers and Gerfin-Moser (1993). For each species, the probe used included coding and noncoding regions. Control hybridizations contained sense strand probes or antisense probes directed against other genes. The frog F-spondin gene (Ruiz l Altaba et al., 1993b) was transcribed with T7 RNA polymerase after digestion with Hindill) to generate an antisense probe.

Expression of vhh-1 in COS cells

Cos cells were grown overnight until 90% confluent and transfected with 1 µg of DNA per 35 mm dish with 12 µg/ml lipofectamino reagent (GIBCO BRL) in Dulbeccos' modified Eagle's medium (DMEM). After 5 hours, cells were washed and incubated in DMEM containing 10% FCS for 18 hours. The medium was then replaced by fresh DMEM containing 10% FCS and cells were incubated for 24–48 hours. COS cells were dissociated 24 hours after transfection with enzyme-free dissociation medium (Specially Media, Incorporated), peeled, and resuspended in OptiMEM containing 10% FCS. Aggregates were made by hanging a 20 Ml drop containing 200–400 cells from the lid of a tissue culture plate. After 24 hours, cell aggregates were placed in contact with rat neural plate explants.

Neural Plate Explant Cultures

Rat neural plate tissue was isolated from the intermediate and dorsal regions of the neural plate of (E9–E10 embryos (at the level of prospective somites 15–19) as described by Placzek et al. (1990a, 193). Chick neural plate tissue was dissected from Hamburger-Hamilton stage 10 chick embryos as described (Yamada et al., 1993). Notochord explants were isolated by dissection from stage 6 chick embryos after dispose treatment. Rat neural plate explants were embedded within three-dimensional collagen gels and culture as described (Tessier-Lavigne et al., 1988; Placzek, et al., 1993). Conjugates were made by wrapping the neural plate explants around COS cell aggregates to maximize the extent of contact.

Chick intermediate neural plate explants, about one-third the size of those used by Yamada et al., (1993), were placed on a monolayer of control or transfected COS cells grown for 44 hours in 35 mm tissue culture dishes. A cushion of collagen gel was placed on top of the explant to maintain the position of the explant and the contact with COS cells and cultures were incubated for 44 hours as described (Yamada et al., 1993).

Limb Bud Explant Cultures

Chick limb bud tissue was dissected from Hamburger-Hamilton stage 20 embryos Mesenchymal tissue that corresponds to the region that expressed shh (Riddle et al., 1993) and defined to have ZPA activity (Honig and Summerball, 1985) and adjacent ectoderm was dissected from posterior limb tissue. Similar sized explants were dissected from anterior limb tissue. Explants were treated as described (Placzek et al., 1993). Rat tissues were wedged between mesenchymal and ectodermal layers of the limb bud explants or were opposed to the mesenchymal layer.

Expression of vhh-1 in Frog Embryos

X laevis embryos at the 1-or-2-cell stage were injected with 100–200 pg of supercoiled plasmid DNA. In all cases injections were performed in the animal hemisphere that is fated to give rise to ectodermal derivatives, including the nervous system (Dale and Slack, 1987). Expression of the vhh-1 cDNA in the sense or antisense orientation in the injected plasmids was driven by the CMV promoter containing the Hox-B4 region A enhancer element (Whitnig et al., 1991). The region A element does not affect the tissue specificity or the level of expression of downstream genes (A.R.A., H.R., AND T.M.J., unpublished data). Expression of vhh-1 transcripts from the injected plasmids was monitored by whole-mount in situ hybridization using an antisense RNA probe.

Immunocytochemistry

Rabbit antibodies against the frog HNF-38 protein were used at 1:5000 to 1:8000 dilution for whole-mount labelling (Dent et al., 1989; Patel et al., 1989) FP3 was detected using monoclonal antibody (MAb) 6G3 (mouse 1gG) and FP4 was detected using MAb K1/2E7 (mouse igG1; Placzek et al., 1993). Islet-1 was detected using rabbit anti-islet-1 antibodies diluted 1:1000 (Thor et al., 1991; Korzh et al., 1993) and MAb 4D5 (mouse IgG, raised by S. Morton against a rat islet-1 fusion protein; Thore et al., 1991). The SC1 protein was detected with a MAb provided by H. Tanaka. For identification of FP3 and FP4 in the same explants, serial sections were labeled with antibodies to FP3 and FP4

Results

Isolation and Characterization of Vertebrate Homologs of the Drosophila hh Gene

To isolate vertebrate homologs of the Drosophila hh gene, zebrafish and rat embryo cDNA libraries were screened with polymerase chain reaction fragments derived from the Drosophila hh cDNA. Five clones isolated from a 9–16 hr postfertilization zebrafish embryo library encoded two distinct hh-related cDNAs, one of which, vhh-1, is described here. The longest vhh-1 cDNA contained a 2.6 kb insert with a single long open reading frame that encodes a protein of 418 amino acids (FIGS. 2A-1 and 2A-2). Zebrafish vhh-1 mRNA expression was confined primarily to midline structures, in particular, the notochord and floor plate. The zebrafish vhh-1 cDNA was used to screen an embryonic day 13 (E13) rat floor plate cDNA library. Sixteen independent cDNA clones were isolated with inserts ranging in size from 0.8 to 2.7 kb. Partial sequencing of each of these cDNA clones revealed that they derived from the same gene. Sequencing of one 2.7 kb clone revealed a single long open reading frame that predicts a protein of 437 amino acids.

The rat vhh-1 cDNA encodes a protein with 71% identity to the zebrafish vhh-1 protein, 94% identity to mouse shh (Echelard et al., 1993), 82% identity to which shh (Riddle et al., 1993), and 47% identity to Drosophila hh (FIGS. 2A-1 and 2A-2). The sequence of the zebrafish shh (Krauss e al., 1993) with the exception of a region at its COOH-terminal end over residues 437–466 (residues aligned to the fly hh sequence; see FIGS. 2A-1 and 2A-2). Zebrafish vhh-1 is identical in the region of divergence to the zhhE protein isolated by Beachy and colleagues (P. Beachy, personal communication). The greatest degree of conservation between the vertebrate and fly proteins occurs over the $NH_2$-terminal 200 amino acids. Both zebrafish and rat vhh-1 proteins contain a hydrophobic $NH_2$-terminus that is likely to serve as a signal sequence (FIG. 2B), suggesting that the processed protein is secreted. The similarity in *sequence and expression pattern (see below) os the zebrafish and rat vhh-1 genes and the mouse and chick shh genes suggests that they are homologs.

Expression of the vhh-1 Gene during Embryogenesis

Figure 3A:
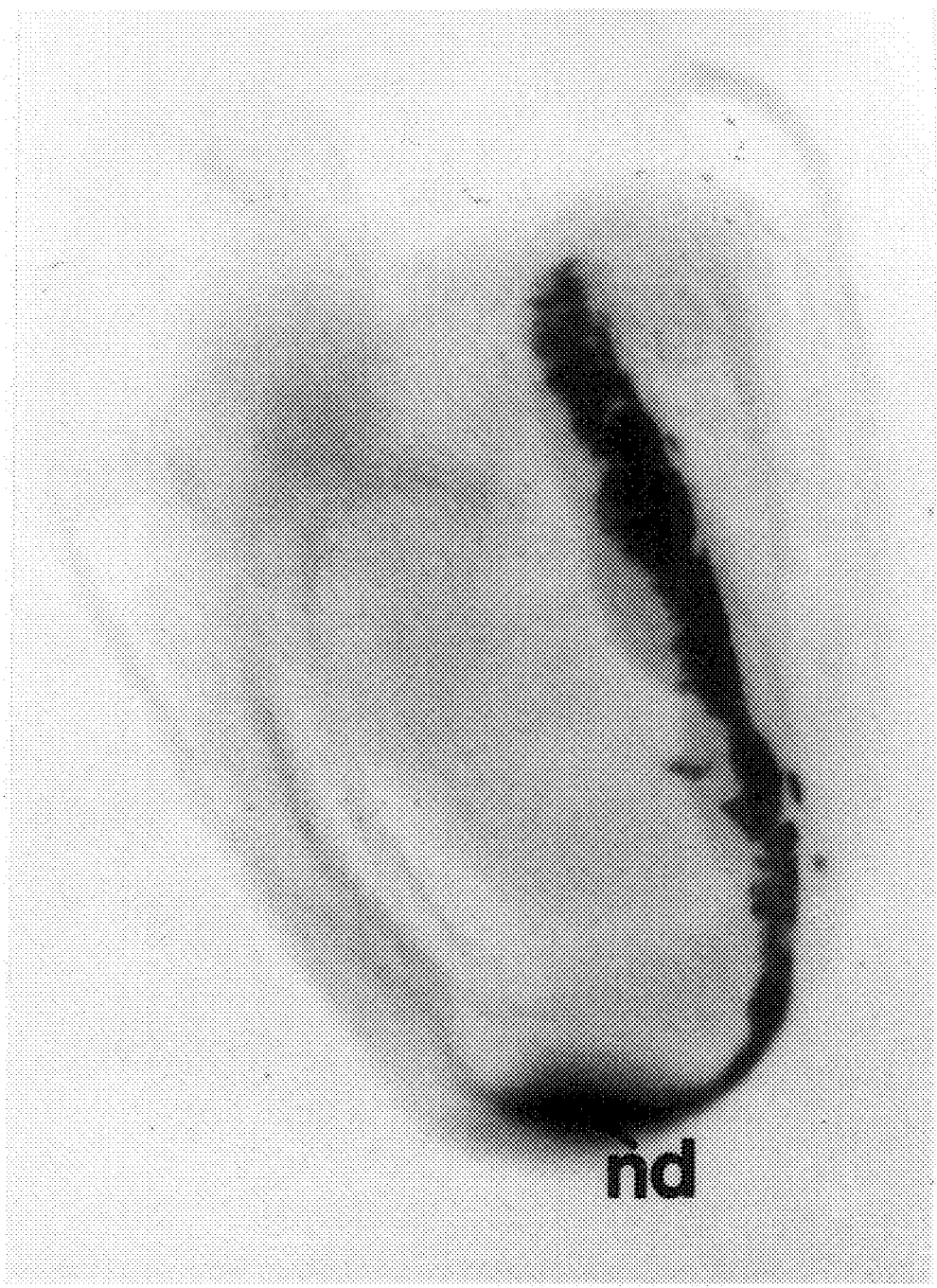
Figure 3B:
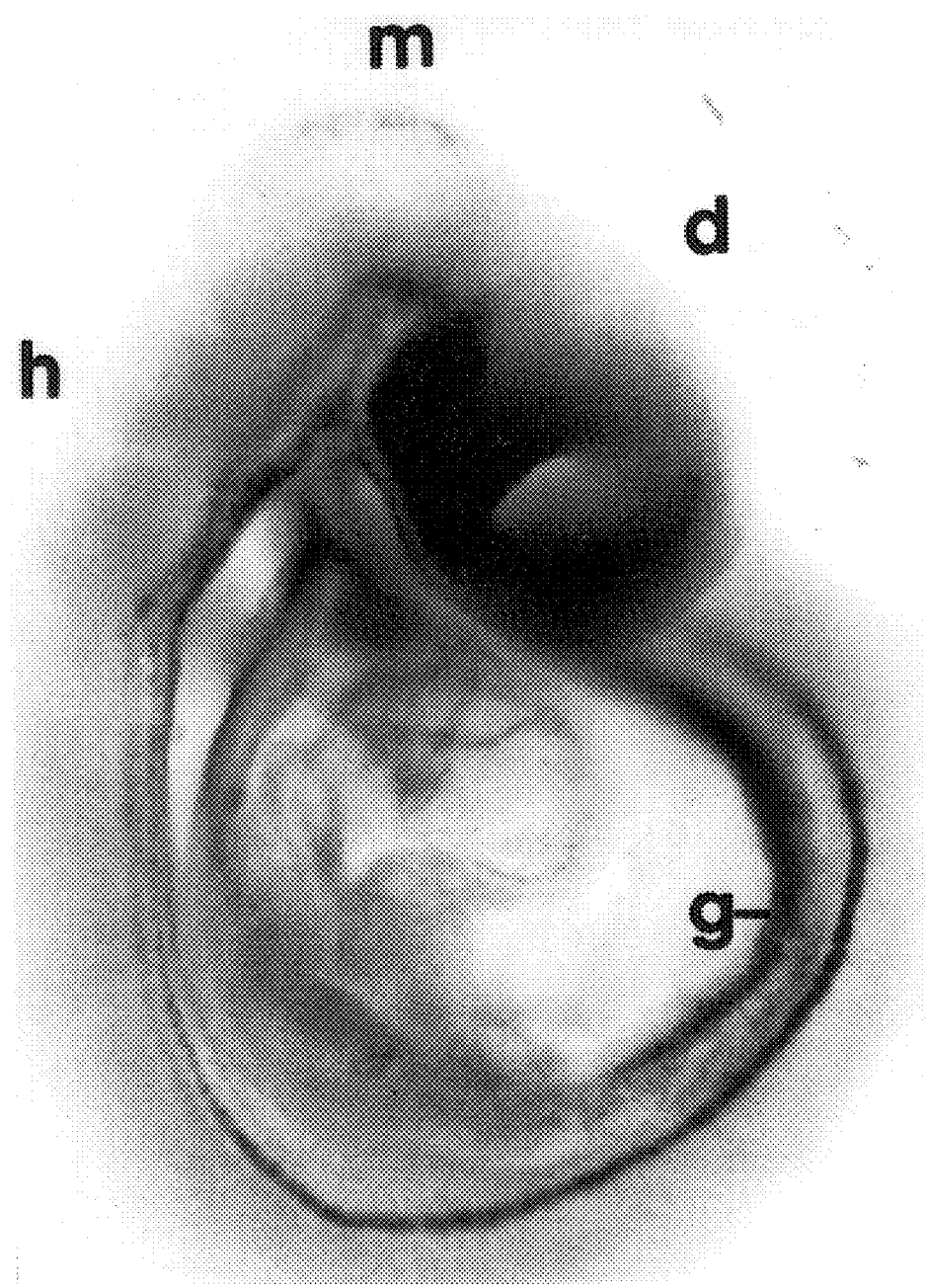
Figure 3C:
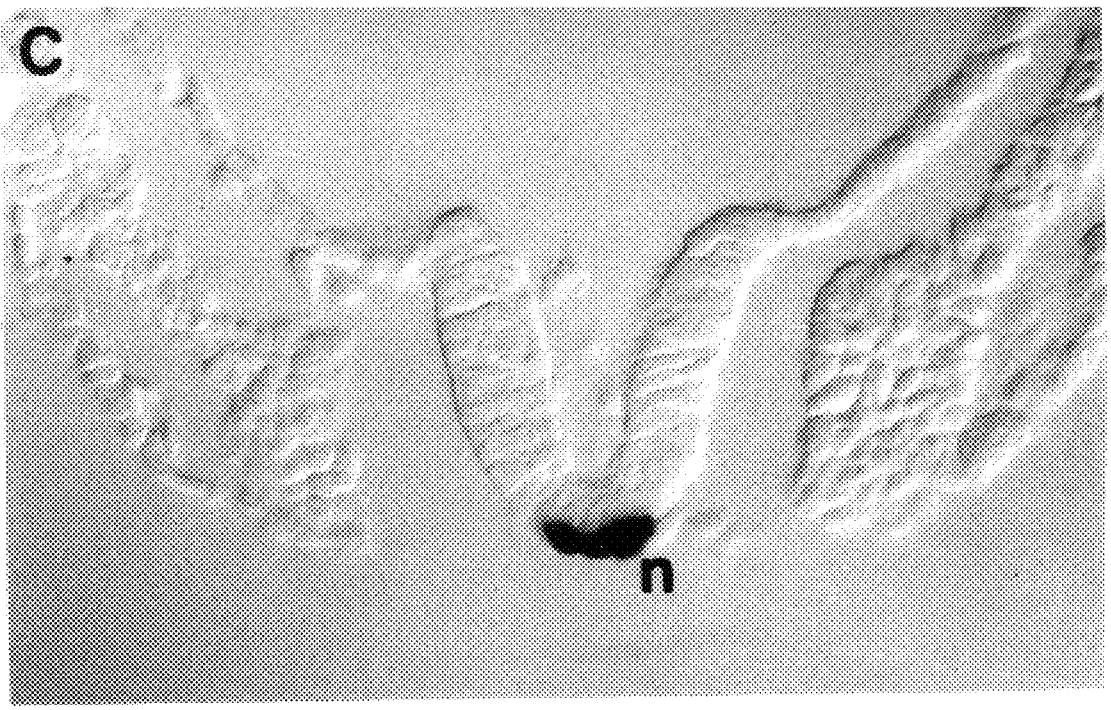
Figure 3D:
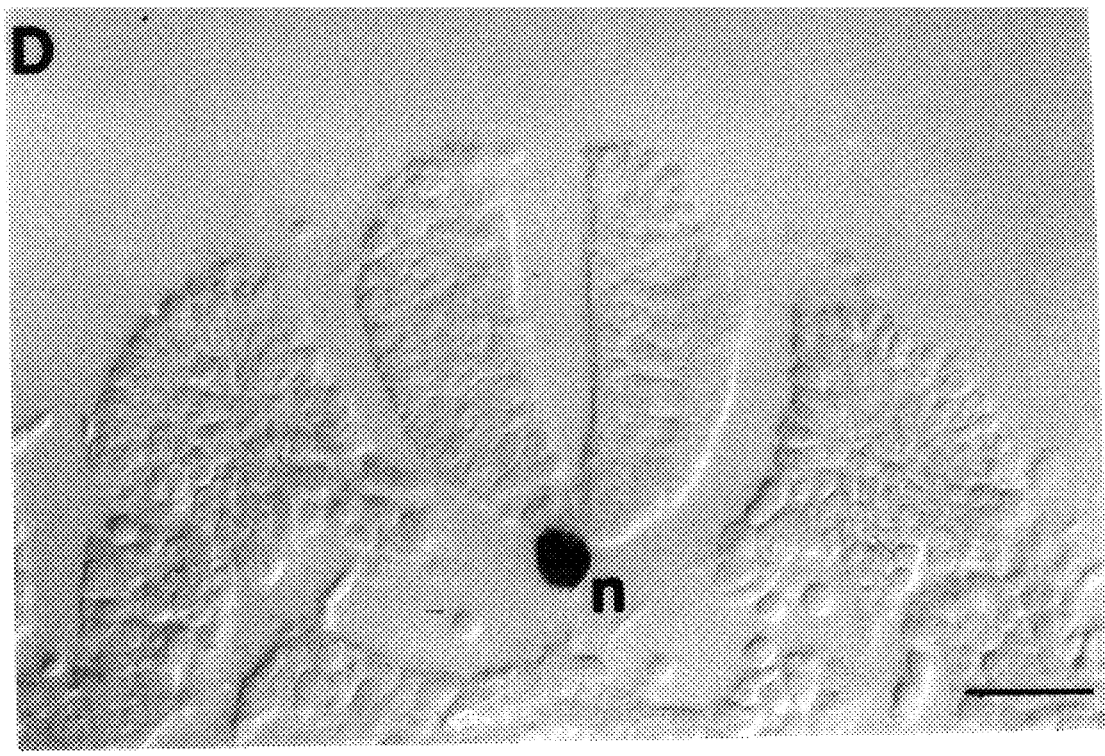
Figure 3E:
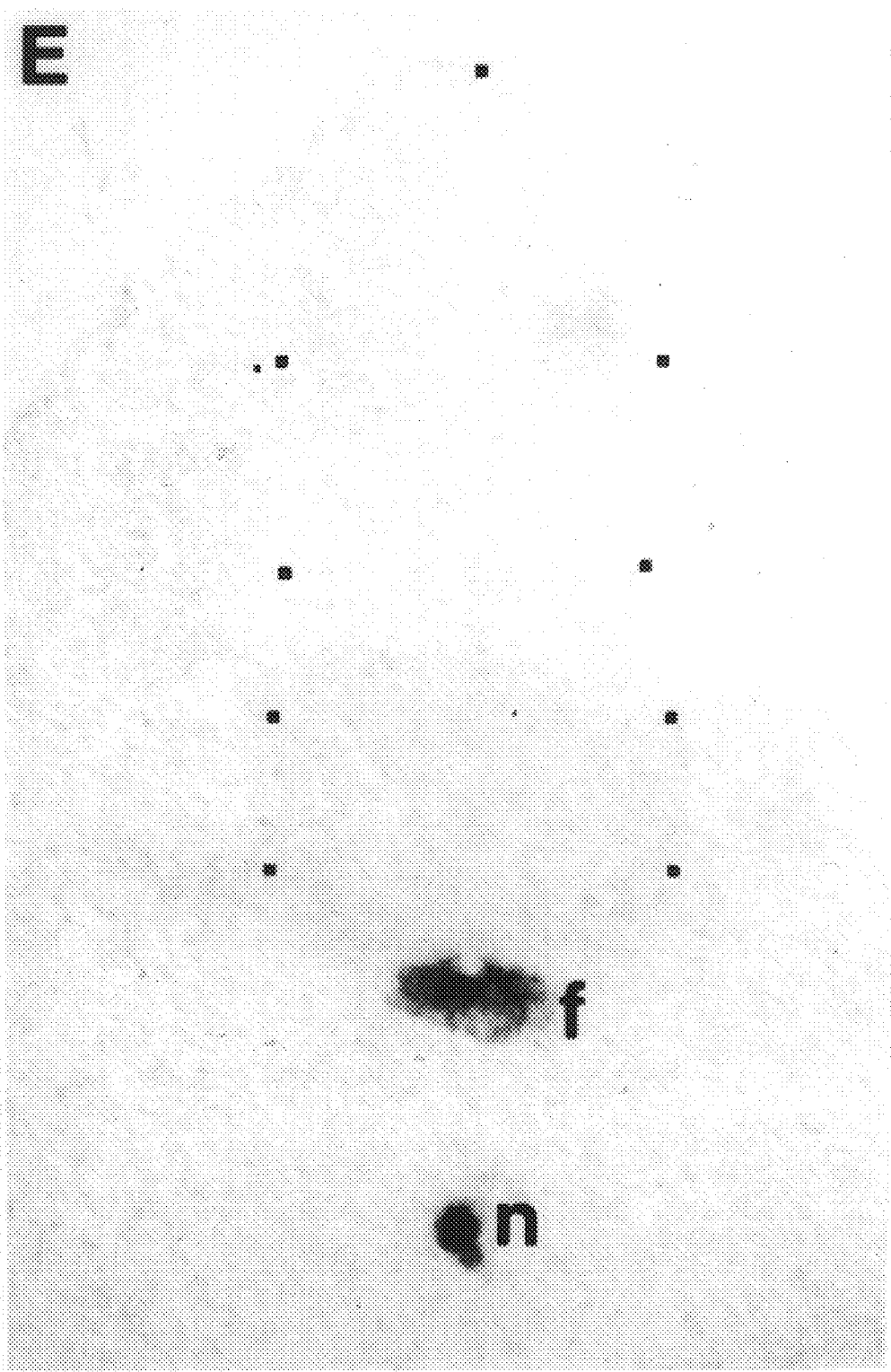

The patterns of expression of the zebrafish and rat vhh-1 genes are similar, and we report here only the expression of the rat gene. We first assayed vhh-1 mRNA expression in gastrulating rat embryos at E9. At this time vhh-1 mRNA was found in the node and in axial mesodermal cells laid down in the wake of the regressing node (FIG. 3A). vhh-1 mRNA expression persists in midline mesodermal cells as they differentiate into the notochord (FIGS. 3B and 3C) and is detectable in this structure until E15, the latest stage examined (FIGS. 3D and 3E). Cells of the neural plate and newly closed neural tube do not express vhh-1 mRNA (FIGS. 3C and 3D). However, floor plate cells at the rostral region of the spinal cord expressed the gene by E10.5 (FIG. 3B), and soon after vhh-1 mRNA was detectable in the floor plate at all rostrocaudal levels, persisting until at least E 15 (FIG. 3E). In the spinal chord and hindbrain, vhh-1 mRNA expression was restricted to the floor plate as assessed by comparison with other rat floor plate markers (data not shown, Placzek et al., 1993; Ruiz l Altaba et al., 1993b). In the forebrain, vhh-1 expression is also located more laterally in the ventral diencephalon and is absent from the ventral midline at the level of the infundibulum (data not shown). Within the diencephalon, vhh-1 mRNA expression extends dorsally up to the boundary between the ventral and dorsal thalamus (data not shown). In the rostral diencephalon, vhh-1 expression is detected ventrally in the region of the developing hypothalamus. The sole dorsal site of neural expression of vhh-1 mRNA is a group of cells at the roof of the midbrain that is first detectable at E10.5 (FIG. 3B).

vhh-1 mRNA was detected in two additional regions of rat embryos from E10.5 to E15. Endodermal cells located in the ventral half of the early gut tube expressed vhh-1 mRNA (FIG. 3B). The intensity of expression of the gene in endodermal derived tissues increases at later stages of development, and by E15–E15 it is expressed at high levels in gut and lung epithelia (data now shown). vhh-1 mRNA was also expressed in posterior mesenchymal cells of the developing limb bud at E11–E14 (see FIG. 7A), which corresponds to the region defined as the zone of polarizing activity (ZPA).

The expression of vhh-1 in the node, notochord, and floor plate, cell groups with floor plate inducing activity, raises the possibility that this gene encodes a floor plate-inducing activity, raises the possibility that this gene encodes a floor plate-inducing molecule. In the following sections we describe the effects of vhh-1 on the differentiation of ventral neural cell types in vivo and in vitro.

Figure 4A:
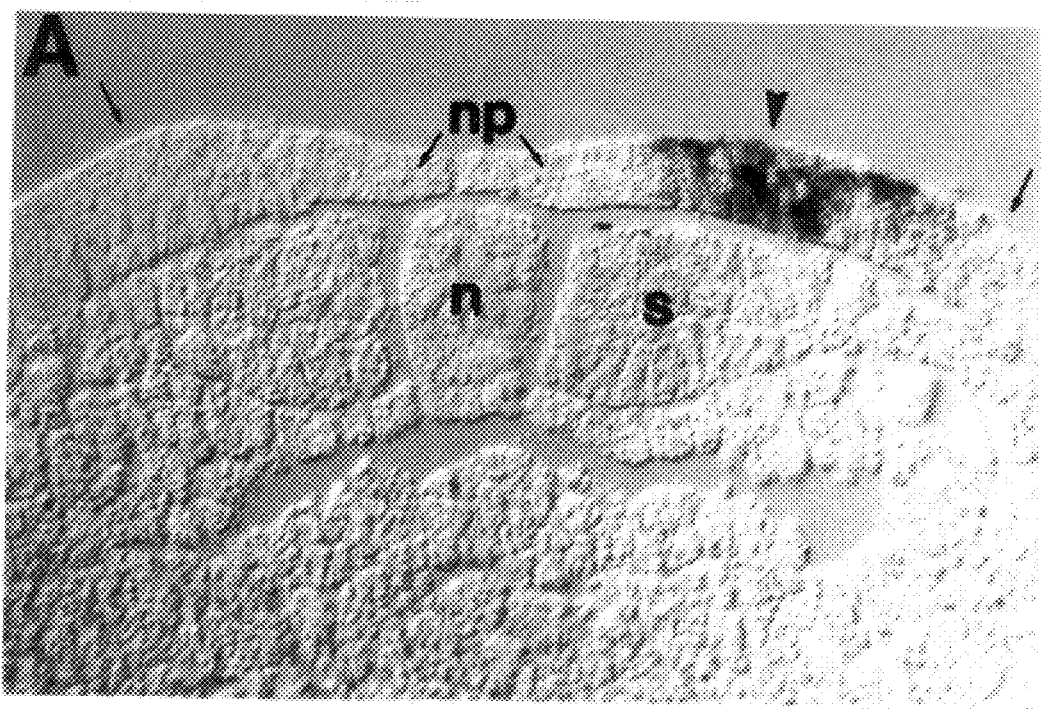

Ectopic Expression of the vhh-1 Gene in Frog Embryos Leads to Floor Plate Differentiation In the Dorsal Neural Tube We monitored the consequences of ectopic expression of the vhh-1 gene in developing frog embryos. Ectopic expression of vhh-1 was achieved by injecting a plasmid vector containing the rat vhh-1 cDNA under the control of a cytomegalovirus (CMV) promoter. AT neural plate stages (stages 13–17), rat vhh-1 mRNA was expressed in large patches of cells located primarily in the region of the anterior epidermis and neural plate (11 of 11 embryos examined) (FIGS. 4A). By the tadpole stage (stages 32–38), however, vhh-1 mRNA was mosaic and detected in smaller groups of cells (data not shown). of injected embryos, 31% (23 of 74 examined) showed ectopic expression of vhh-1 in the neural tube. Within the neural plate and neural tube, there was no consistent restriction in the domain of neural expression of the CMV-driven rat vhh-1 gene (FIG. 4A; data not shown).

Figure 4B:
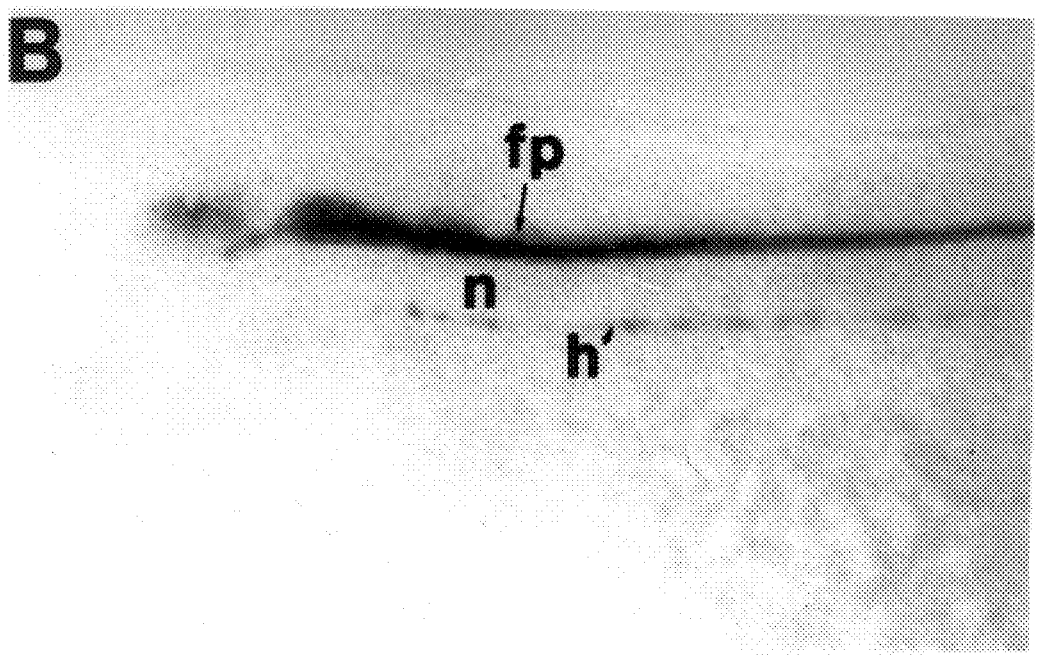
Figure 4C:
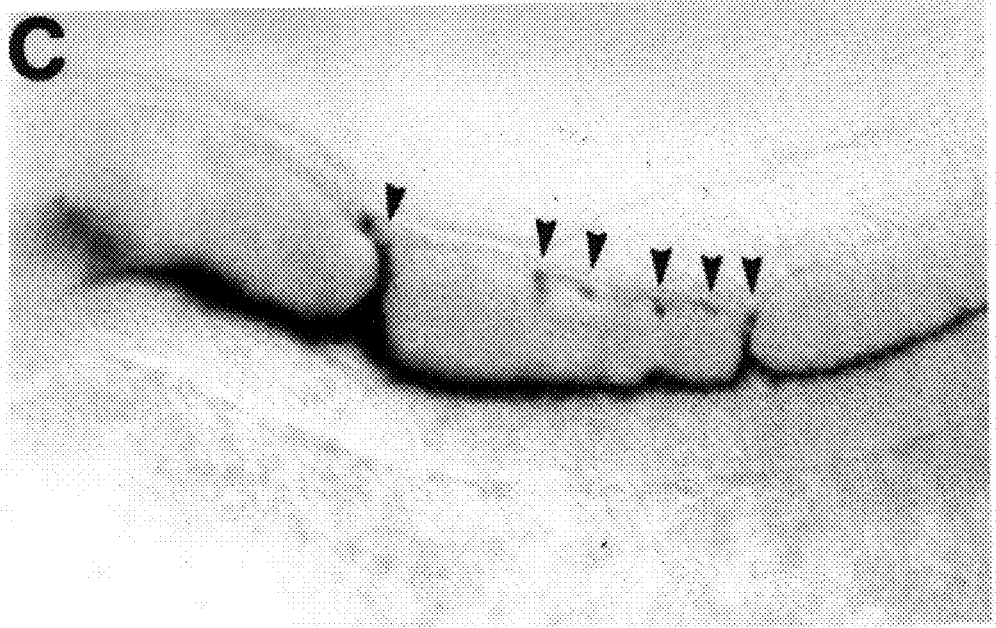
Figure 4D:
Figure 4E:
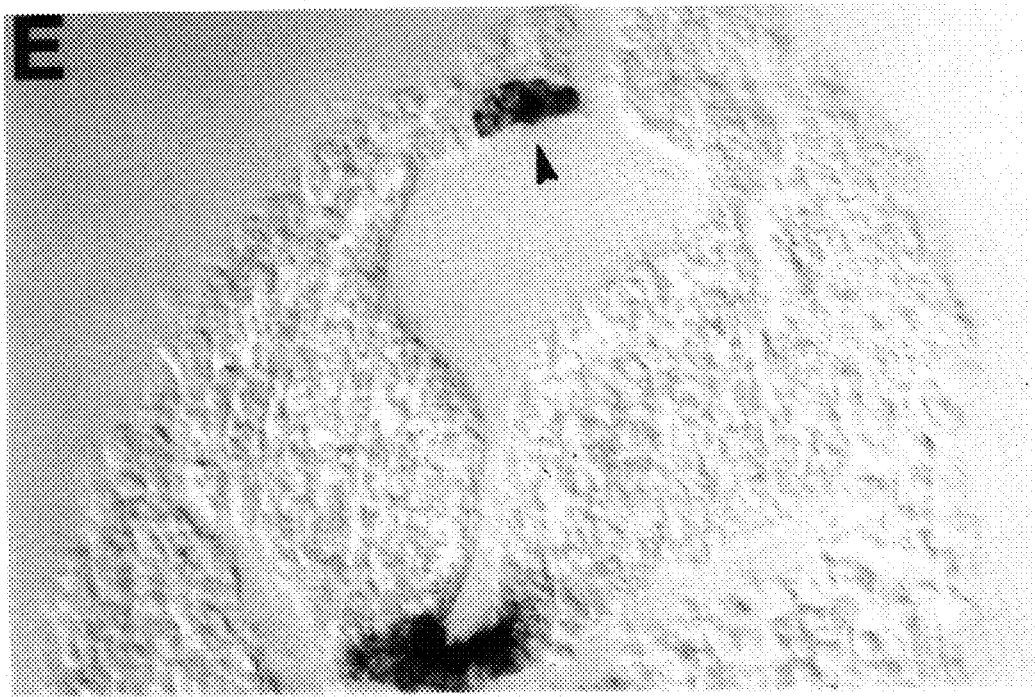
Figure 4F:
Figure 4G:
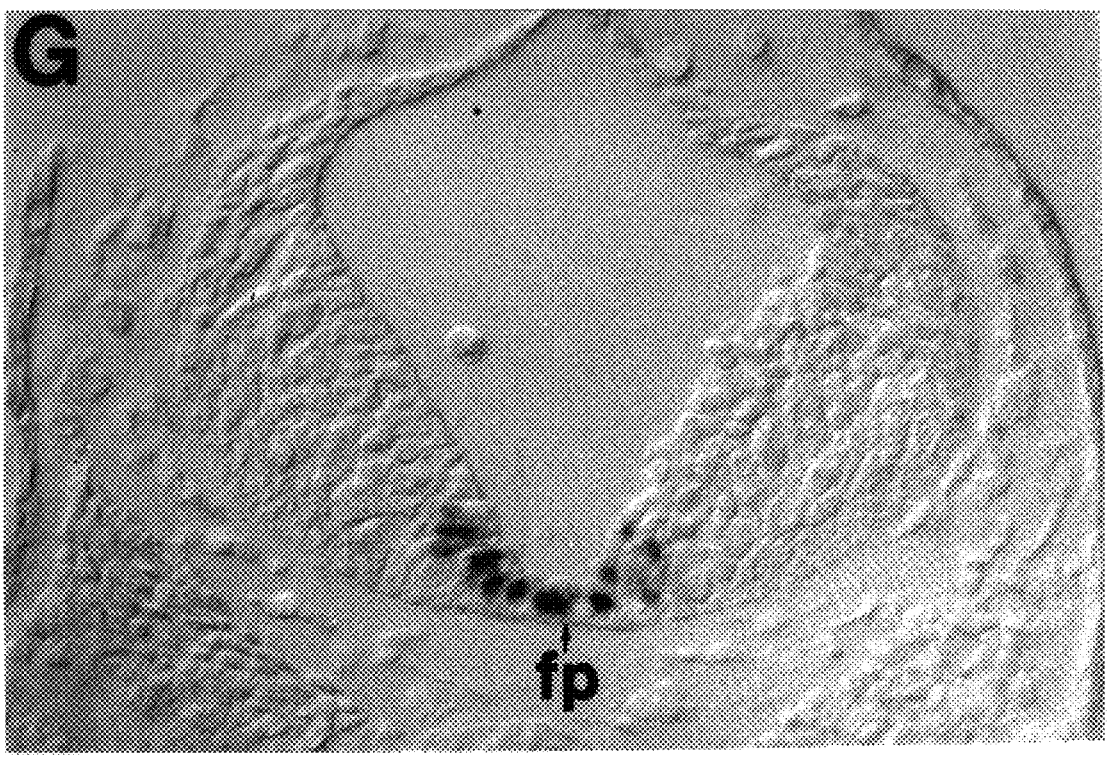
Figure 4H:
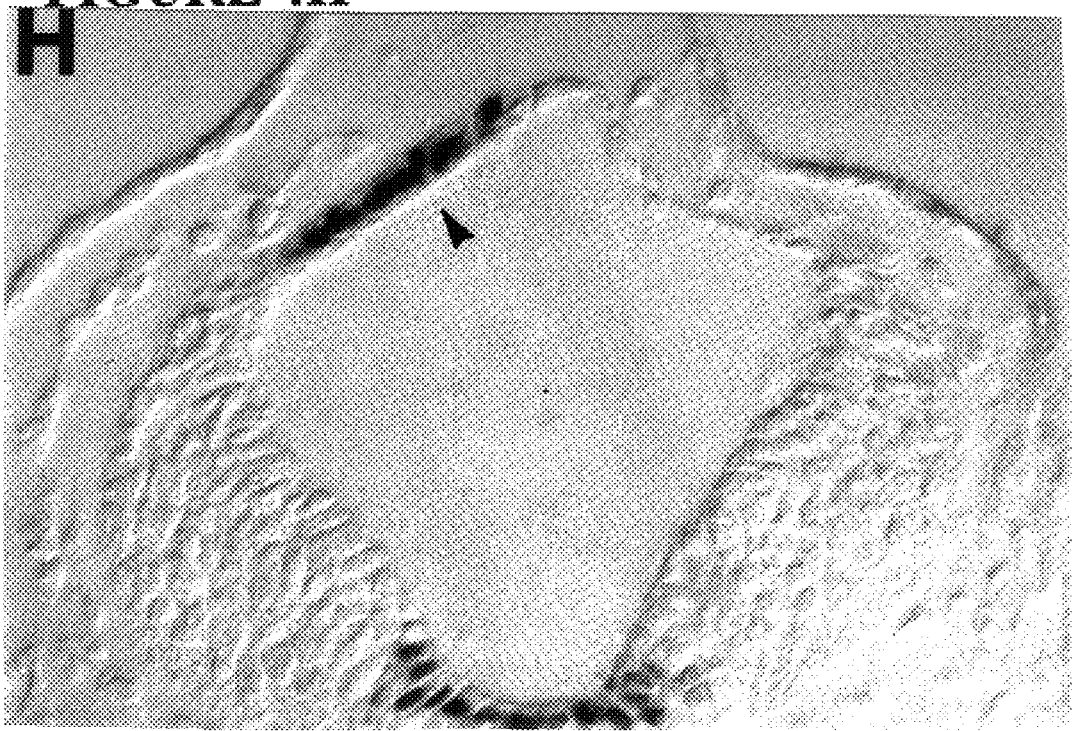
Figure 4I:
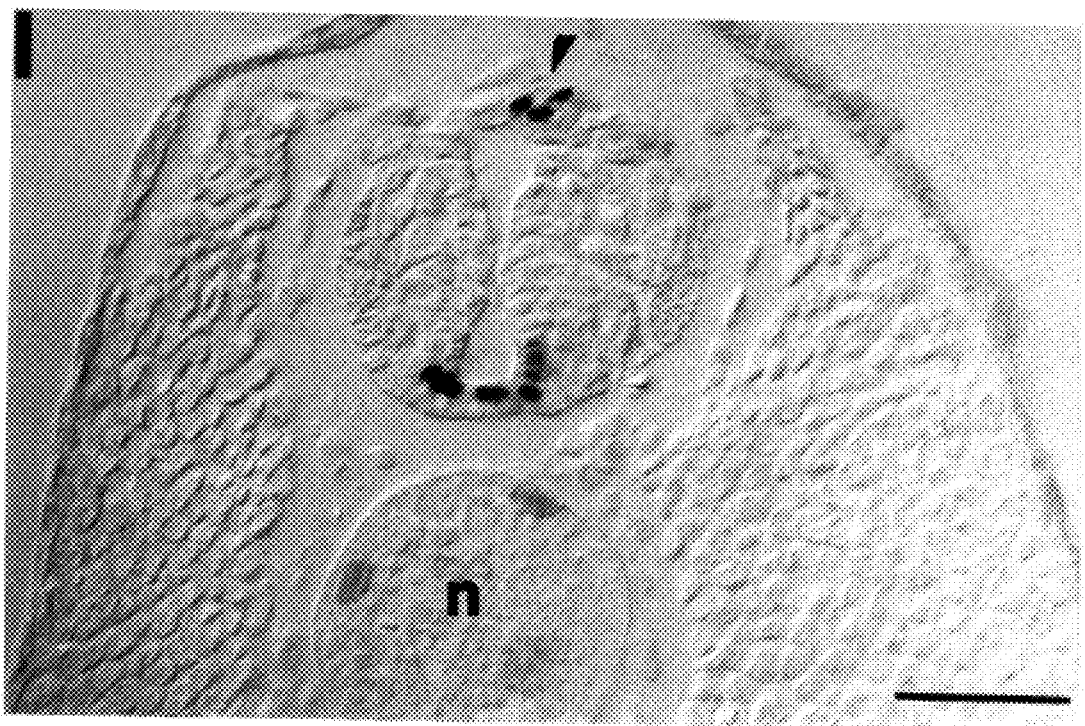

We determined whether the widespread expression of vhh-1 RNA leads to the differentiation of floor plate cells in ectopic locations by monitoring the expression of two floor plate markers, the cell adhesion molecule F-spondin (Klar et al., 1992; Ruiz l Altaba et al., 1993a) (FIGS. 4B and 4D) and the transcription factor HNF-3β (19 of 153) were detected in regions other than the floor plate (FIGS. 4C, 4E, 4F, 4H and 4I). Ectopic expression of both markers was detected at midbrain, hindbrain, and spinal cord levels but not in forebrain regions (FIGS. 4E, 4F, 4H, and 4I). Embryos injected with a plasmid driving expression of vhh-1 cDNA in the antisense orientation showed a markedly lower incidence of ectopic F-spondin expression (2%; 4 of 198), and ectopic HNF-3β cells were not detected (0 of 53). Thus, the widespread expression of rat vhh-1 in developing frog embryos leads to the ectopic induction of floor plate marker. Although the ectopic expression of HNF-3β and F-spondin RNA was observed at all rostrocaudal levels of the neuraxis except the forebrain, the predominant location of ectopic markers expression was in cells at the dorsal midline, in or near the roof plate (FIGS. 4C, 4E, 4F, 4H, and 4I). In several embryos, the morphology of the neural tube in regions of ectopic floor plate markers expression was abnormal with marked constrictions or folds in the neural tube (data not shown).

Floor Plate Differentiation Induced in Vitro by vhh-1

To test more directly the ability of vhh-1 to induce ventral neural cell types, we used established in vitro assays of rat floor plate (Placzek et al., 1993) and chick motor neuron (Yamada et al., 1993) differentiation.

To detect floor plate differentiation, we monitored the induction of the floor plate antigens FP3 and FP4 (FIGS. 5A and 5B) in rat neural plate explants cultured in vitro. Notochord and floor plate induce the expression of FP3 and FP4 when grown in contact with E9–E10 rat neural plate tissue (FIGS. 5C and 5D) (Placzek et al., 1993). Expression vectors containing full-length vhh-1 cDNA in sense or antisense orientations were transiently transfected into COS cells. About 25% of COS cells expressed vhh-1 RAN (data not shown).

Figure 5J:
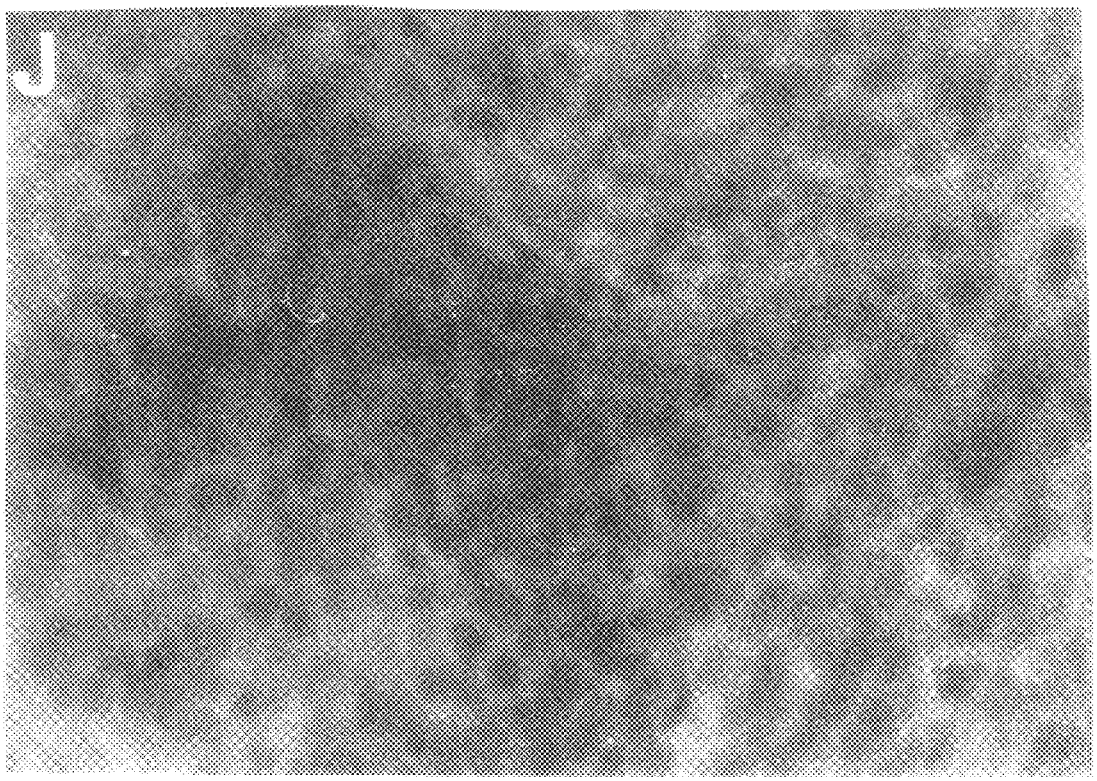
Figure 5K:
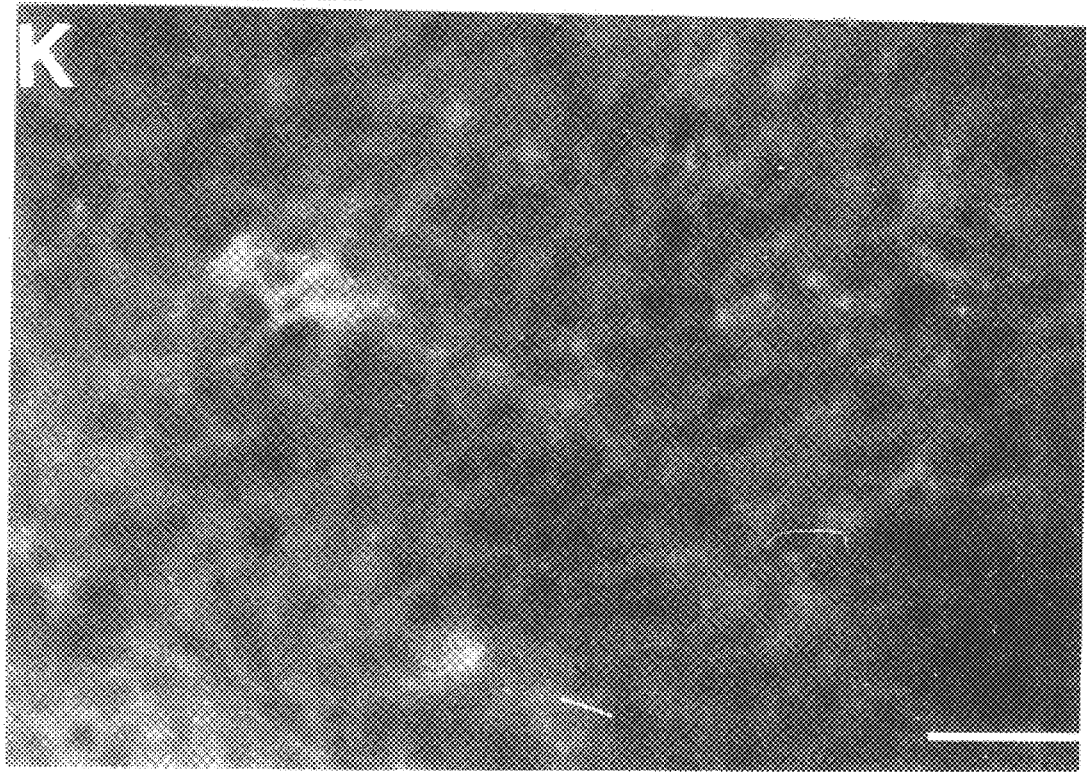

Of neural plate explants grown in contact with COS cells expressing sense vhh-1 cDNA, 70% expressed FP3 and 47% expressed FP4 (FIGS. 5E–5H; Table 1). As with floor plate induction by the notochord, not all explants that expressed FP3 also expressed FP4. This may reflect the later onset of FP4 expression in vivo (Placzek et al., 1993). The domain of FP3 and FP4 expression within neural plate explants was similar in size to that induced by the notochord, and labeled cells were located close to the junction of the COS cells aggregate and neural plate explant. Induction of floor plate differentiation by vhh-1 may thus be local and possibly contact-dependent process. Consistent with this, medium harvested from vhh-1 transfected COS cells did not induce FP3 or FP4 when added to neural plate explant grown alone (data not shown). It remains to be determined, however, whether vhh-1 activity can diffuse into the medium. Neural plate explants grown in contact with cells transfected with antisense vhh-1 cDNA did not express FP3 or FP4 (FIGS. 5J and 5K; Table 1).

The simplest explanation of these results is that vhh-1 protein is secreted from COS cells and interacts with neural plate cells to trigger, directly, floor plate differentiation. Nevertheless, it remains possible that expression of vhh-1 in COS cells induces the synthesis of a distinct factor that mediates floor plate induction. In addition, these results do not resolve whether the vhh-1 protein is sufficient to induce floor plate differentiation since COS cells could provide an accessory factor that acts in concert with the vhh-1 protein.

Motor Neuron Differentiation Induced In Vitro by vhh-1

In vitro studies have provided evidence that signals from the notochord can induce the differentiation of motor neurons as well as floor plate cells (Yamada et al., 1993). The expression of vhh-1 in the notochord therefore raises the questions of whether motor neurons can also be induced by vhh-1.

Figure 6A:
Figure 6B:
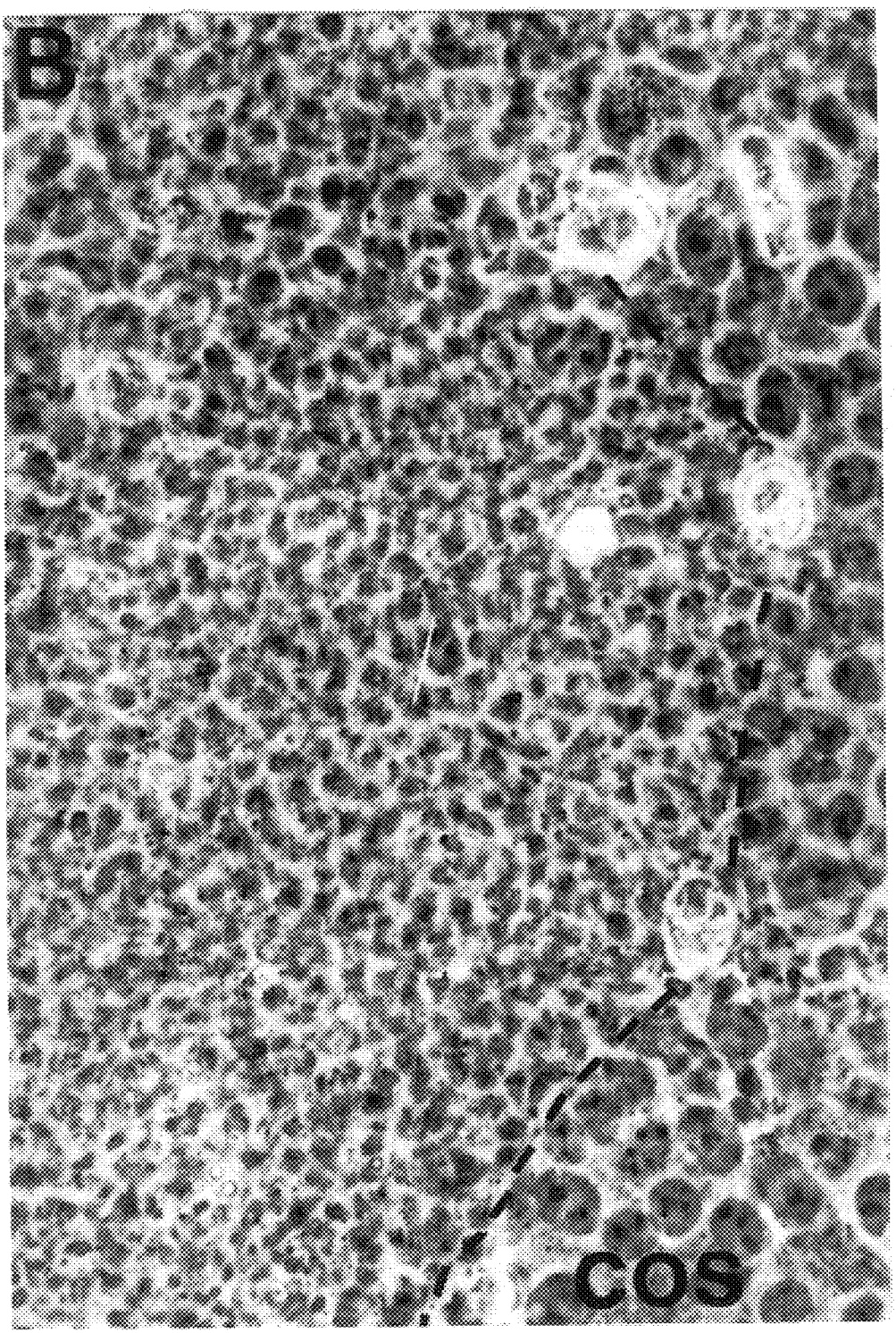
Figure 6C:
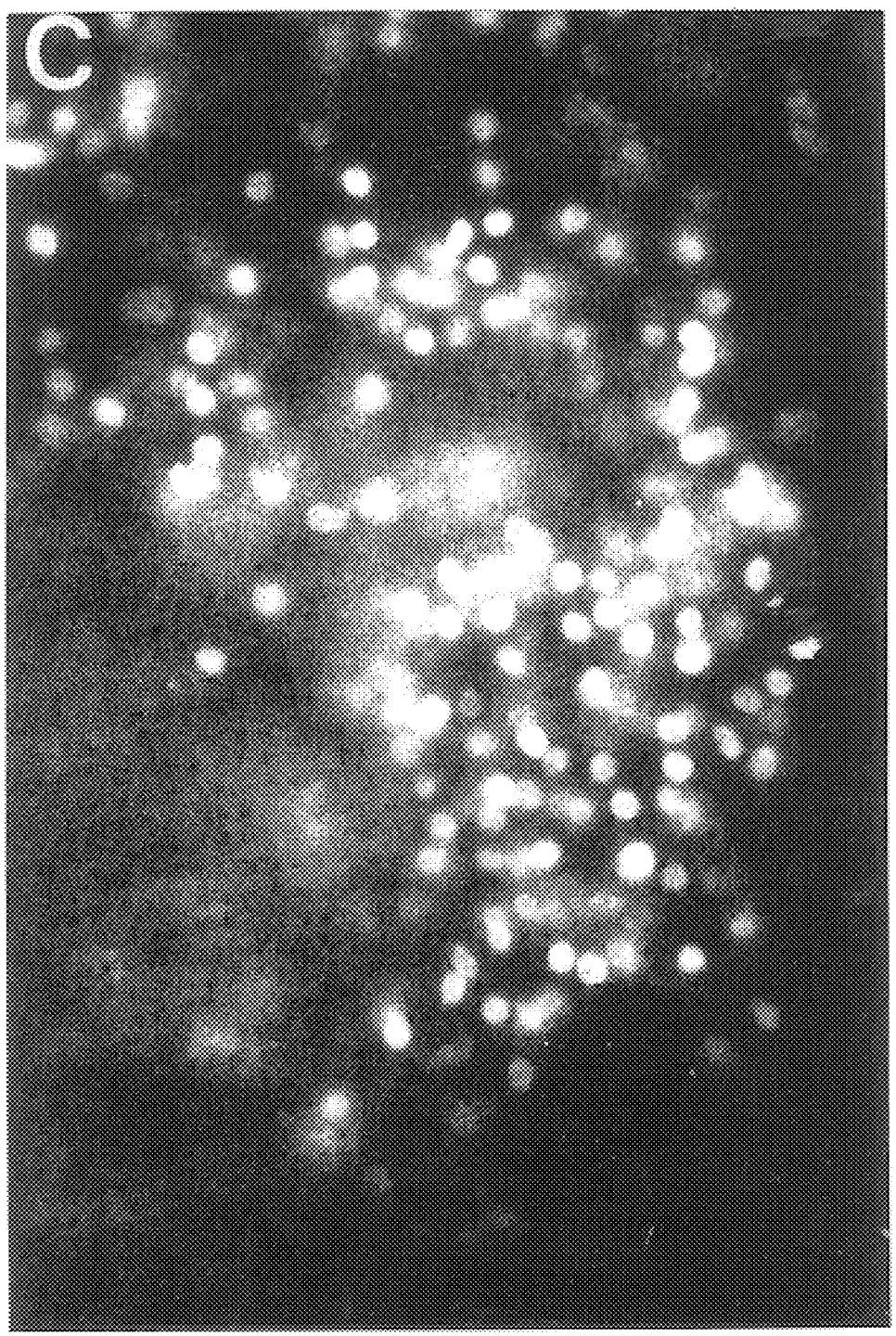
Figure 6D:
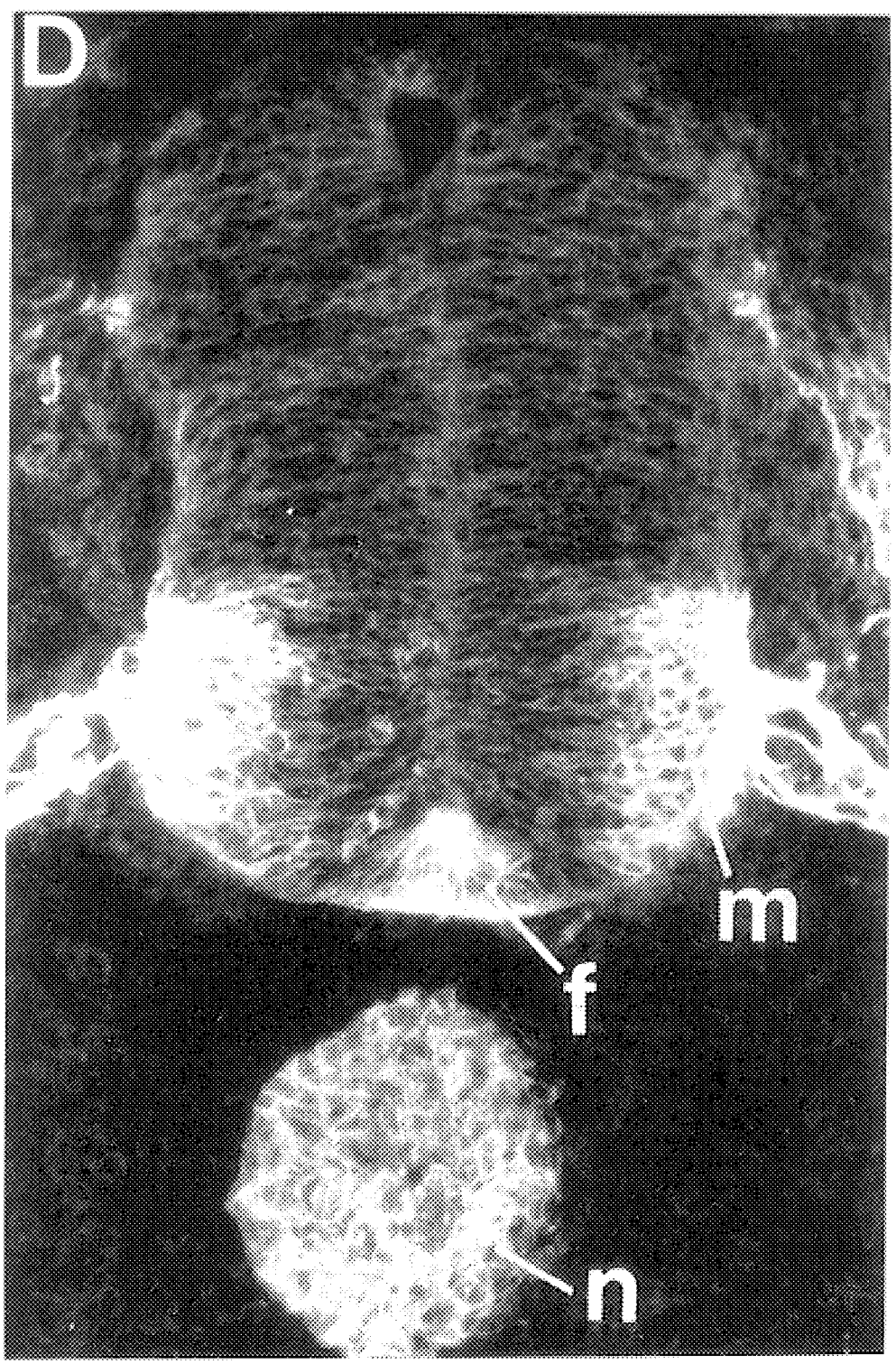
Figure 6E:
Figure 6F:
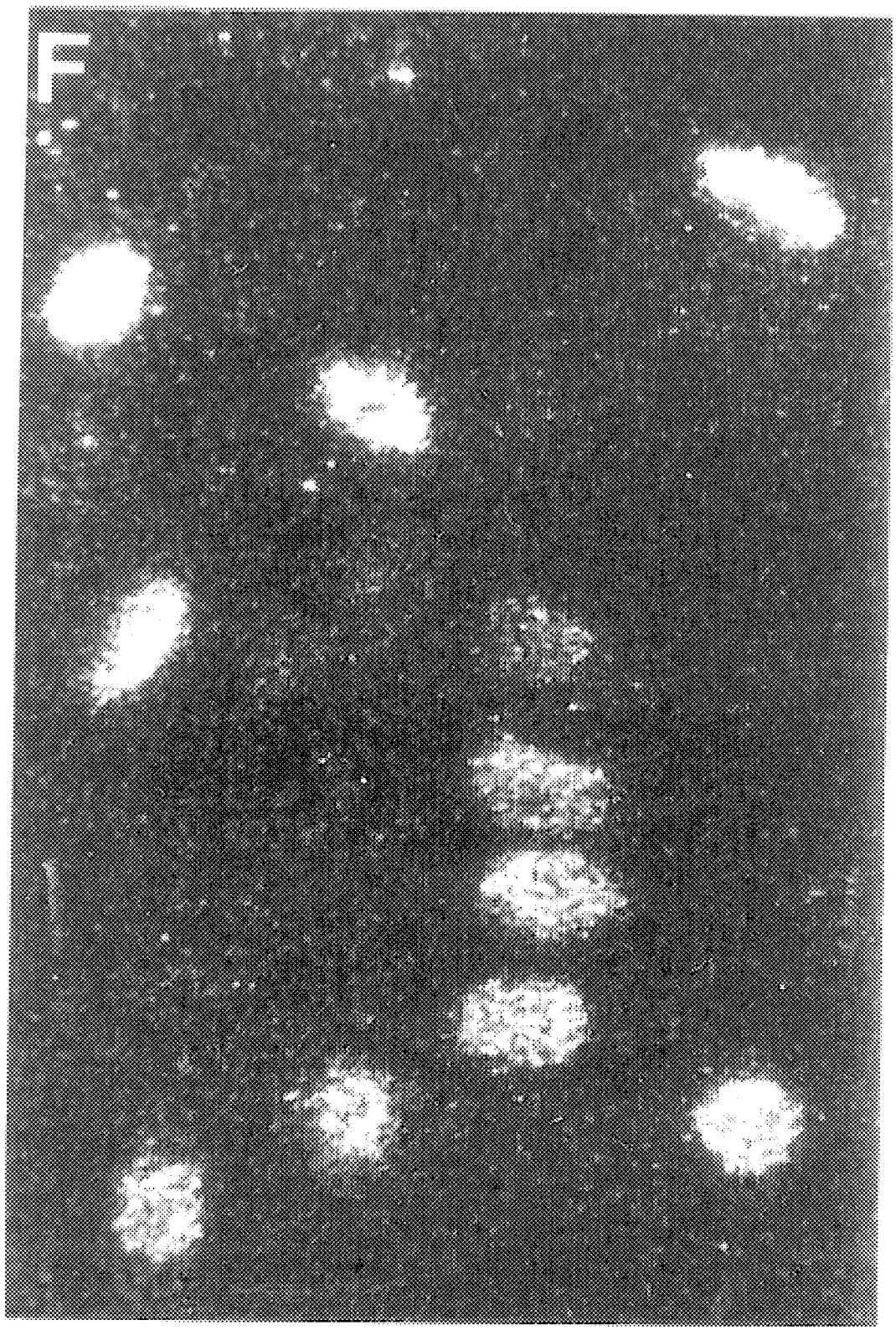
Figure 6G:
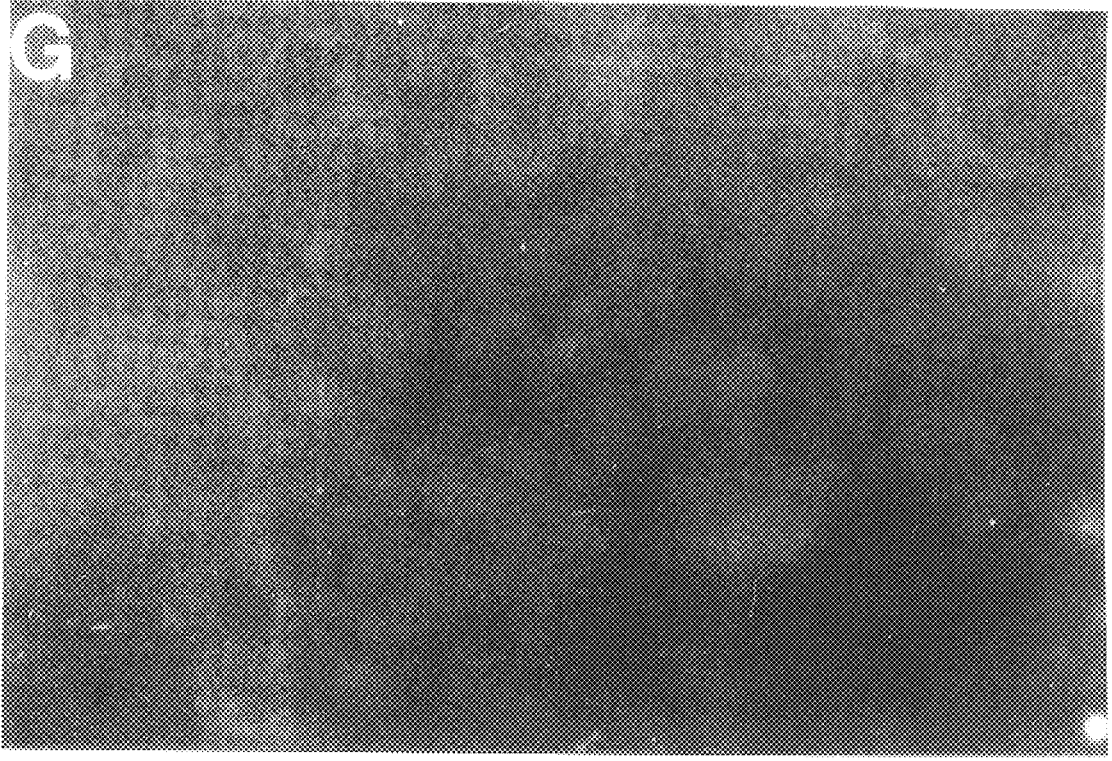
Figure 6H:
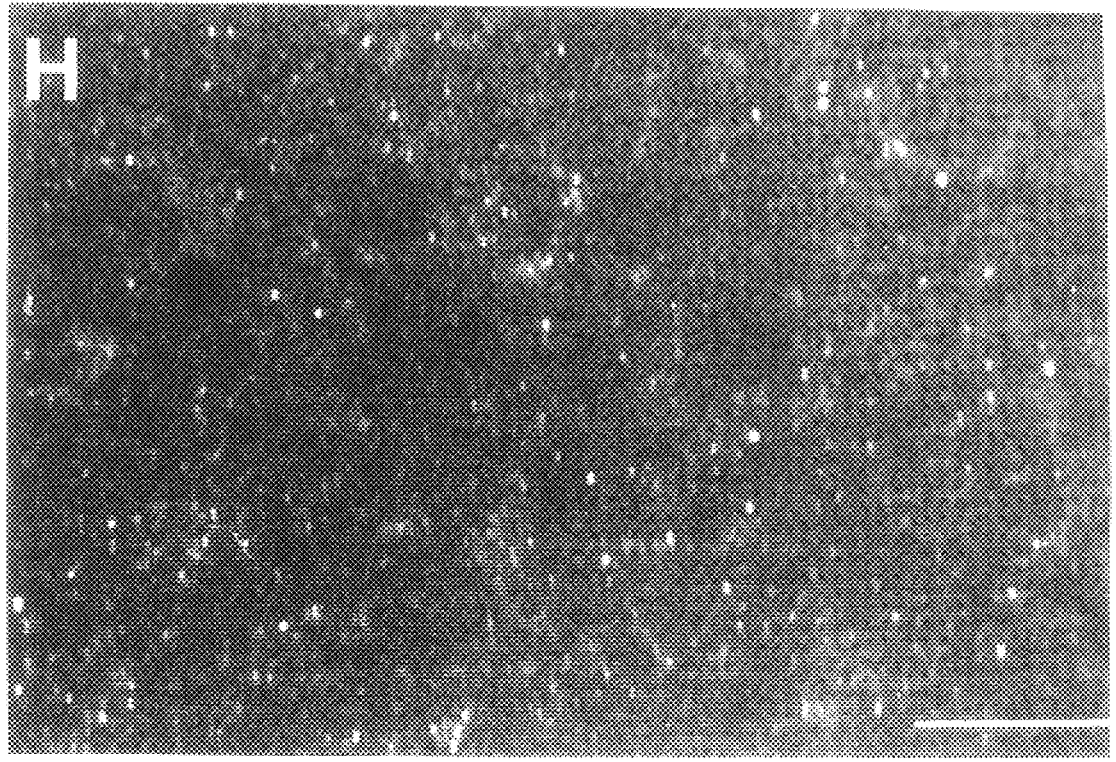

To determine whether vhh-1 can also induce motor neurons, we used chick neural plate explants in which motor neuron differentiation has been characterized (Table 1; Yamada et al., 1993). Motor neurons can be identified by the coexpression of two markers, the LIM homeodomain protein islet-1 (Thor et al., 1991; Ericson et al., 1992) (FIG. 6A) and the immunoglobulin-like protein SC1 (Tanaka and Obata, 1984) (FIG. 6D). Intermediate neural plate explants (Yamada et al., 1993) were grown for 44 hrs on a monolayer of COS cells transfected with sense or antisense vhh-1 expression plasmids. Neural plate explants grown on COS cells expressing the sense cDNA contained an average of 83 Islet-1' cells (FIGS. 6B and 6C; Table 1), whereas explants grown on COS cells transfected with antisense vhh-1 cDNA expressed at most one islet-1' (FIG. 6G, Table 1, motor neuron induction). Immunofluorescence labelling and confocal imaging revealed that most islet-1' cells expressed SC1 on their surface (FIGS. 6E and 6F) (n=27 explants), confirming their identity as motor neurons. Medium conditioned by COS cells transfected with sense vhh-1 cDNA did not induce islet-1' calls in intermediate neural plate explants (date not shown).

Since ambiguous markers of floor plate differentiation in chick neural plate explants are not available, we could not assay whether floor plate differentiation also occurs in chick neural plate explants in response to vhh-1.

Taken together, these in vitro assays provide evidence that COS cells expressing vhh-1 can induce both floor plate cells and motor neurons, although it is unclear whether motor neuron induction is a direct response to vhh-1.

Widespread expression of the vhh-1 gene in frog embryos leads to ectopic floor plate differentiation, and COS cells expressing vhh-1 can induce floor plate and motor neuron differentiation in neural plate explants in vitro. Our results suggest that expression of vhh-1 by the notochord participates in the induction of floor plate and motor neuron differentiation in overlying neural plate cells.

Involvement of vhh-1 in Floor Plate and Motor Neuron Differentiation

In vitro studies have provided evidence for two distinct activities of the notochord, a contact mediated floor plate

TABLE 1

Induction of Floor Plate and Motor Neuron Differentiation in Neural Plate Explants in Vitro

| Inducer | Floor Plate Induction[a] | | | Motor Neuron Induction[b] | |
|---|---|---|---|---|---|
| | Percentage FP3+ Explants | Percentage FP4+ Explants | n (Explants) | Number of Islet-1+ Cells | n (Explants) |
| Notochord[c] | 85 | 63 | 65, 30 | 210 ± 12 | 22 |
| vhh-1 COS cells | 70 | 47 | 47 | 83 ± 8 | 24 |
| Antisense vhh-1 COS cells | 0 | 0 | 16 | 0–1 | 20 |
| Floor plate-conditioned medium | | | | 60 ± 4 | 20 |
| Posterior limb mesenchyme | 73 | 45 | 22 | | |
| Anterior limb mesenchyme | 0 | 0 | 22 | | |

[a]Numbers derive from three to six separate experiments.
[b]Values given are means ± SEM from 1 of 6 similar experiments: caudal stage 10 notochord was used.
Floor plate-conditioned medium was prepared as described by Yamada et al. (1993).
[c]Data for floor plate induction from Placzek et al. (1993).

Floor Plate Differentiation Is Induced In Vitro by Posterior Limb Bud Calls

Figure 7A:
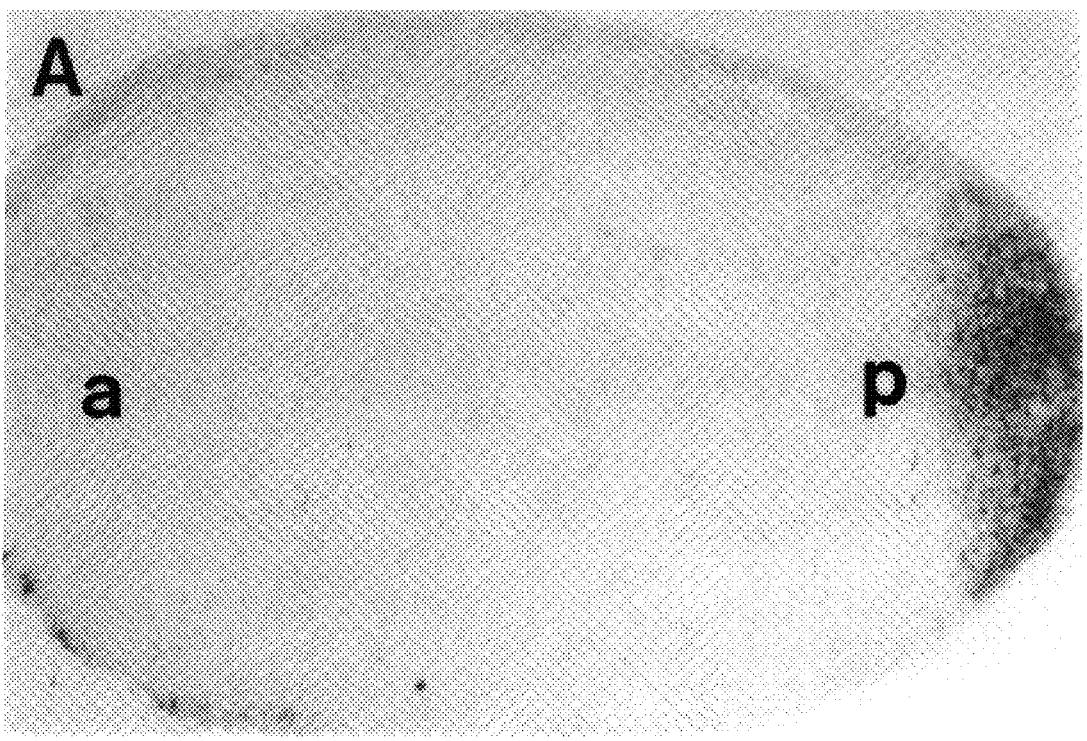
Figure 7B:
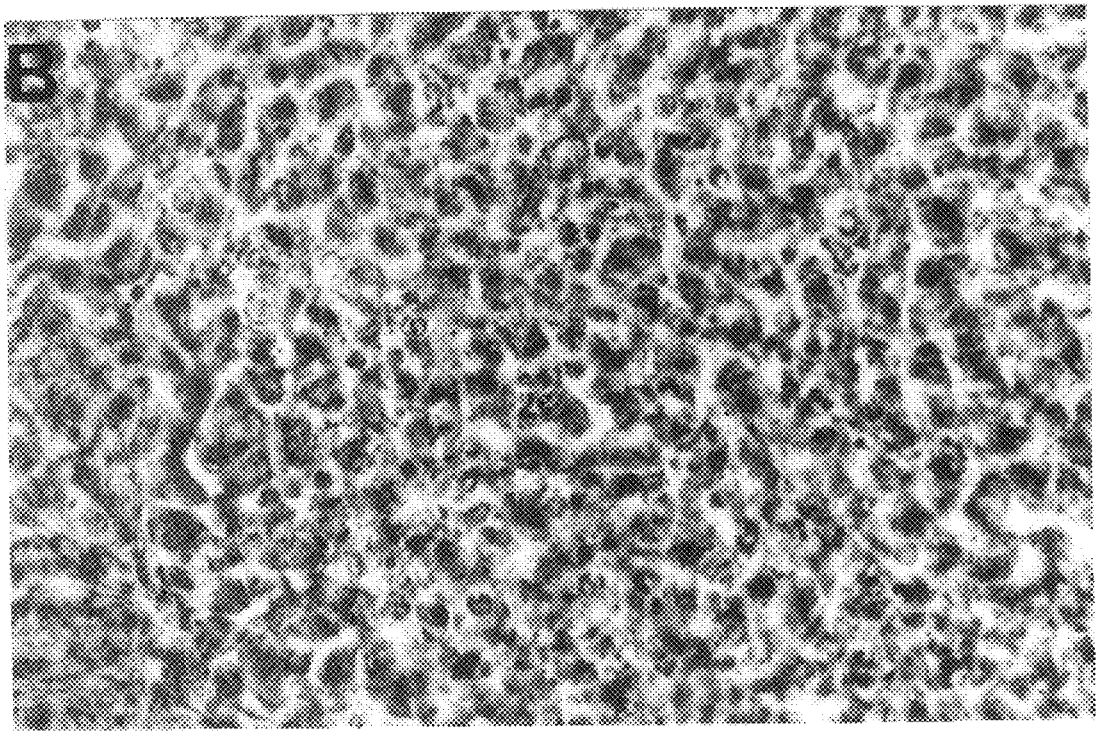
Figure 7C:
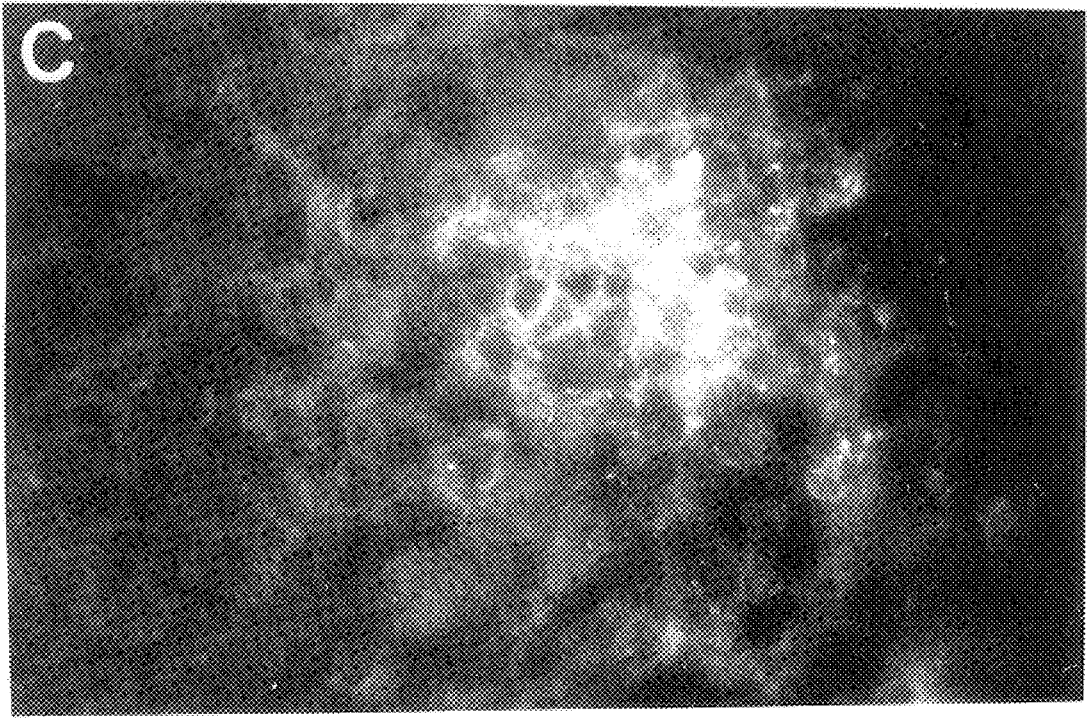
Figure 7D:
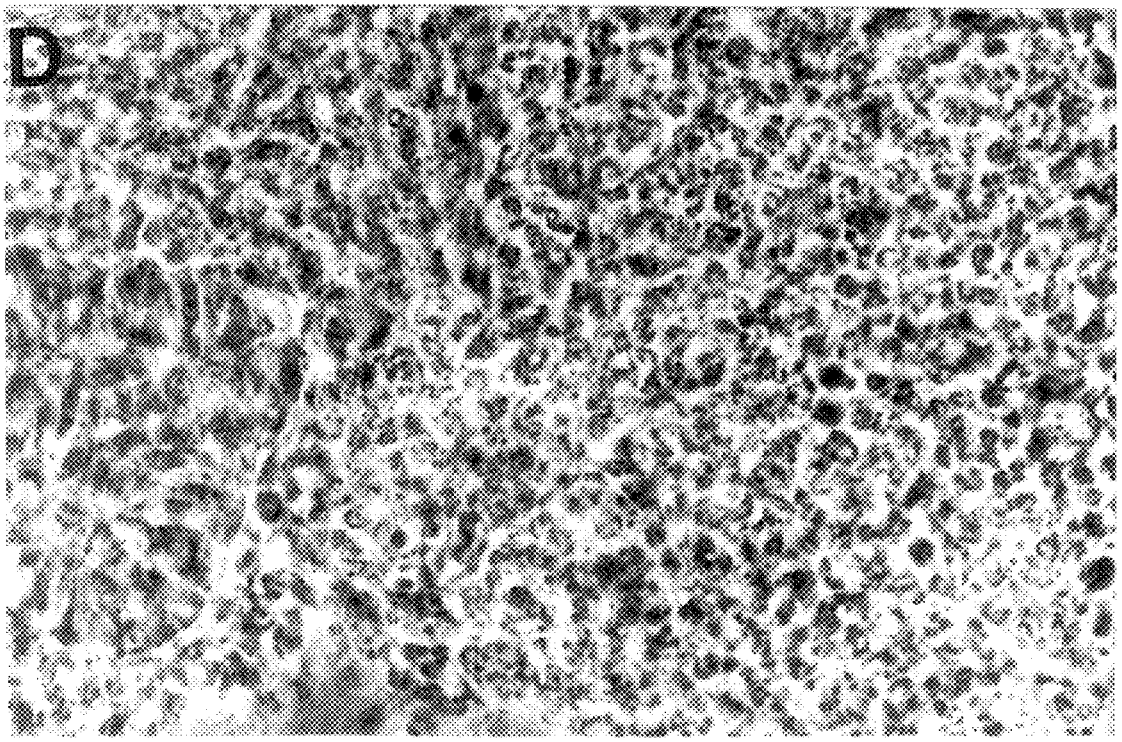
Figure 7E:

The node, notochord, and floor plate can induce floor plate differentiation (Placzek et al., 191, 1993) and can also mimic the ability of the ZPA to evoke digit duplications in the developing chick limb bud (Hornbruch and Wolpert, 1986; Wagner et al., 1990, Stoker and Carison, 1990; Hogan et al., 1992). The expression of vhh-1 in the ZPA region (see FIG. 3; FIG. 7A) raises the questions of whether the ZPA can mimic the ability of midline cells to induce floor plate differentiation. To test this, we assayed the ability of the ZPA to induce floor plate differentiation in rat neural plate explants in vitro. The ZPA region of the posterior limb mesenchyme (Honig and Summerbell, 1985) was isolated together with the adjacent apical ectoderm to provide factors that maintain ZPA activity in vitro (Anderson, et al., 1993; Vogel and Tickle, 1993; Niswander et al., 1993). Of neural plate explants grown in contact with posterior limb mesenchyme and ectoderm, 73% expressed FP3 and 45% displayed FP4 (Table 1, floor plate induction; FIGS. 7B and 7C). In contrast, neural plate explants grown in contact with anterior limb mesenchyme and ectoderm did not express FP3 or FP4 (FIGS. 7D and 7E; Table 1, floor plate induction). Neural plate explants grown in contact with posterior limb ectoderm in the absence of mesenchyme did not induce FP3 or FP4 (data not shown). These results support the idea that vhh-1 expression confers cells with floor plate inducing properties.

Discussion

The differentiation of ventral cell types within the neural tube is controlled by signals that derive from the notochord. We have identified a vertebrate homolog of the Drosophila hh gene, vhh-1, that is expressed in midline mesodermal and neural cells: the node, the notochord, and the floor plate.

inducing activity and a diffusible motor neuron inducing activity (Placzek et al., 1990a, 1990b, 1993; Yamada et al., 1993). Both activities are also acquired by the floor plate after its induction by the notochord. Our results provide evidence that floor plate induction occurs as a direct response to vhh-1. Moreover, as with the notochord derived signal, floor plate induction by vhh-1 appears to be a local event and may be contact mediated.

Although vhh-1 can induce motor neurons as well as floor plate cells, our results do not resolve whether this induction is direct and thus whether vhh-1 could represent the diffusible motor neuron inducing activity present in notochord- and floor plate-conditioned medium. Since vhh-1 can induce floor plate differentiation, the induced floor plate could, in turn, secrete a motor neuron-inducing factor distinct from vhh-1. It is also unclear whether vhh-1 is present in medium conditioned by cells that secrete vhh-1. In Drosophila, hh is known to act nonautonomously (Mohler, 1988), and analysis of hh (or a downstream mediator of hh function) can act over a distance of a few cell diameters (Ingham, 1993; Heberlein et al., 1993; Ma et al., 1993; Heemskerk and Dinardo, 1994; Basier and Struhl, 1994). Consistent with this, hh protein has been detected beyond the domain of hh mRNA expression (Taylor et al., 1993).

The early expression of vhh-1 by the notochord is synchronous with its floor plate and motor neuron inducing activities. However, the persistent expression of vhh-1 by the notochord at later stages of embryonic development contrasts with in vitro studies showing that the notochord rapidly loses its ability to induce floor plate in vitro (Placzek et al., 1990a, 1990b, 1993). This difference could reflect the onset of expression of notochord factors that inhibit the action of vhh-1 or the loss of expression of a required cofactor. In rat, vhh-1 expression by floor plate cells can first be detected after neural tube closure, consistent with the time at which floor plate cells acquire floor plate and motor neuron inducing activity (Placzek et al., 1993; Yamada et al., 1993). By this time it appears that cells in the neural plate have been exposed to signals that initiate more neuron differentiation (Yamada et al., 1993). It is unlikely, therefore, that vhh-1 expression by the floor plate is involved in the initiation of motor neuron differentiation. Nevertheless, it is possible that later-born motor neurons (Hollyday and Hamburger, 1977) depend on floor plate-derived vhh-1 for their differentiation. A second function of vhh-1 in the floor plate may be to participate in the recruitment of additional cells to the floor plate as the neural tube grows (Placzek et al., 1993).

Pathway of Floor Plate Differentiation

The ability of vhh-1 to induce ectopic HNF-3β in the neural tube may be relevant to the steps involved in the normal development of the floor plate. Pintallavis and HNF-3β are expressed in the node, notochord, ad floor plate (Ruiz l Altaba and Jessell, 1992; Monaghan al., 1993; Sasaki and Hogan, 1993; Ruiz l altaba et al., 1993b). The expression of both genes by the floor plate is dependent on inductive signals from the notochord (Ruiz l Altaba et al., 1992; A.R.A., MP., J.D., AND T.M.J., unpublished data), and expression occurs before other floor plate properties.

Widespread expression of Pintallavis and HNF-3β induces the expression of floor plate markers in the dorsal neural tube (Ruiz l Altaba et al., 1993a; A.R.A. et al., unpublished data; Sasaki and Hogan, 1994), suggesting that HNF-3β and Pintallavis are involved in the specification of floor plate fate in cells at the midline of the neural plate. The induction of HNF-3β by vhh-1, therefore, appears to mimic the ability of the notochord to trigger a program of floor plate differentiation that includes the transcription of genes such as vhh-1 itself and F-spondin.

Requirements for Floor Plate Differentiation

Widespread expression of rat vhh-1 in frog embryos induces ectopic floor plate differentiation in vivo. The chick and zebrafish shh genes have also been shown to induce floor plate markers, although only in midbrain regions (Echelard et al., 1993; Krauss et al., 1993). Our in vivo studies show clearly that atopic expression of floor plate markers can also be obtained at hindbrain and spinal cord levels, although not in the forebrain. The absence of ectopic floor plate markers in the forebrain is consistent with in vitro studies showing that notochord cannot induce floor plate differentiation in anterior regions of the neural plate (Placzek et al., 1993).

Although widespread expression of vhh-1 in frog embryos induces ectopic floor plate differentiation in vivo. The chick and zebrafish shh genes have also been shown to induce floor plate markers, although only in midbrain regions (Echelard et al., 1993; Krauss et al., 1993). Our in vivo studies show clearly that atopic expression of floor plate markers can also be obtained at hindbrain and spinal cord levels, although not in the forebrain. The absence of ectopic floor plate markers in the forebrain is consistent with in vitro studies showing that notochord cannot induce floor plate differentiation in anterior regions of the neural plate (Placzek et al., 1993).

Although widespread expression of vhh-1 induces ectopic floor plate differentiation at all levels of the neuraxis caudal to the forebrain, we observed that ectopic floor plate markers were found primarily in the dorsal region of the neural tube. Notochord grafts can, however, induce floor plate differentiation at all dorsoventral positions within the neural tube (van Straaten et al., 1988; Yamada et all, 1991). Thus signals from the notochord may, in vivo, induce floor plate differentiation in regions of the neural tube that do not respond to vhh-1 alone. The observed differences in neural tube responses to vhh-1 and to the notochord could result from quantitative differences in vhh-1 levels provided by the notochord and by the vhh-1 expression plasmid. Alternatively, the notochord may provide additional signaling molecules, one function of which could be to regulate the expression of transcription factors that cooperate with Pintallavis and HNF-3β in the determination of floor plate fate.

vhh-1 Expression and the )Reciprocity of Neural Tube and Limb Polarizing Activities The expression of vhh-1 in the node, notochord, floor plate and posterior limb mesenchyme provides a possible molecular basis for the shared signaling properties of these cell groups (Jessell and Dodd, 1992; Ruiz 1 Altaba and Jessell, 1993). Grafts of Hensen's node, the notochord, or floor plate into the anterior region of the developing chick limb bud evoke digit duplications that mimic those of the ZPA (Hornbruch and Wolpert, 1986; Wagner et al., 1990; Stoker and Carlson, 1990; Hogan et al., 1992). The present results show that the ZPA can induce floor plate differentiation. Moreover, the common signaling properties of the node, notochord, floor plate, and ZPA appear to correlate more closely with the pattern of vhh-1 expression than with retinoid activity (Thaller and Eichele, 1987; Rossant et al., 1991; Wagner et al., 1992). Additional support for the idea that the limb and neural patterning have a common basis is provided by recent studies showing that chick shh can mimic ZPA activity when expressed in anterior regions of the limb bud (Riddle et al., 1993). Expression of the vhh-1 gene in the node, notochord, and floor plate is likely, therefore, to underlie the ability of these midline cell groups to mimic the activity of the ZPA in evoking digit duplications. Reciprocally, the expression of vhh-1 may underlie the ability of the ZPA to induce floor plate differentiation.

Hh-Related TGCβ and Wnt Proteins as Secreted Regulators of Call Pattern

In Drosophila, dpp, wg, and hh regulate cell fate and pattern in embryonic and larval development. In vertebrates, members of the TGFβ and wnt gene families regulate cell differentiation during neural development. The wnt-1 gene is required for midbrain and anterior hindbrain development (McMahon and Bradely, 1990; Thomas and Capecchi, 1990), and dorsalin-1, a member of the TGFβ family, promotes the differentiation of dorsal cell types in neural plate explants in vitro (Blaser et al., 1993). Our results suggest that vhh-1 also contributes to neural patterning in vertebrates, acting to induce distinct cell types in the ventral region of the neural tube. Thus, dorsalin-1 dorsally and vhh-1 ventrally may provide polarizing signals with opposing actions that specify cell fates along the dorsoventral axis of the neural tube.

REFERENCES

Aebischer, P., Winn, S. R., Tresco, P. A., Jaeger, C. B. and Greene, L. A. Transplantation of polymer encapsulated neurotransmitter secreting cells: effect of the encapsulation technique. J. Biomech. Eng. 113:178–183 (1991).

Anderson, R., Landry, M., and Muneoka, K. Maintenance of ZPA signaling in cultured mouse limb bud cells. Development. 117:1421–1433 (1993).

Baker, N. Transcription of the segment-polanty gene wingless in the imaginal discs of Drosophila, and the phenotype of a pupal-lethal wg mutation. Development. 102:489–497 (1988).

Basler, K., and Struhl, G. Hedgehog, a product of posterior compartment cells in Drosophila, organizes anterior compartment pattern. Nature. in press (1994).

Basler, K., Edmund, T., Jessell, T. M., and Yamada, T. Control of cell pattern in the neural tube: regulation of cell differentiation by dorsalin-1, a novel TGFβ family member. Cell. 73:687–702 (1993).

Bolce, M. E., Hammati-Brivanlou, A., and Harland, R. M. XFKH2, a Xenopus HNF-3α homologue, exhibits both activin inducible and autonomous phases of expression in early embryos. Dev. Viol. 160:413–423 (1993).

Bovolenta, P., and Dodd, J. Perturbation of neuronal differentiation and axon guidance in the spinal cord of mouse embryos lacking a floor plate analysis of Danforth's short-tall mutation. Development. 113:625–639 (1991).

Campbell, G., Weaver, T., and Tomlinson, A. Axis specification in the developing Drosophila appendage: the role of wingless, decapentaplegic, and the homeobox gene aristaless. Cell. 74:1113–1123 (1993).

Cardin, A. D., and Weintraub, H. J. R. Molecular modeling of protein-glycosaminoglycan Interactions. Arteriosclerosis. 9:21–32 (1989).

Clarke, J. D. W., Holder, N., Soffe, S. R. and Storm-Mathissen, J. Neuroanatomical and functional analysis of neural tube formation in notochordless Xenopus embryos laterally of the ventral spinal cord is lost. Development. 112:499–516 (1991).

Dale, L., and Slack, J. M. W. Fate map for the 32-cell stage of Xenopus laevis. Development. 99:527–551 (1987).

Dent, J. A. Poison, A. G., and Klymkowsky, M. W. A whole-mount immunocytochemical analysis of the expression of the intermediate filament vimentin in Xenopus. Development. 105:61–74 (1989).

Dirksen, M. L., and Jamrich, M. A novel activin-inducible, blastospore lip specific gene of Xenopus Laevis contains a fork head DNA-binding domain. Genes Dev. 6:599–608 (1992).

Echelard, Y., Epstein, D. J., St.-Jacques, B., Shen, L., Mohler, J., McMahon, J. A., and McMahon, A. P. Sonic hedgehog, a member of a family of putative signaling molecules is implicated in the regulation of CNS polarity. Cell. 75:1417–1430 (1993).

Erffert, H., Ohlenbusch, A., Fahling, W., Lottor, H., and Thomssen, R. Nucleotide sequence of the ospAB operon of a *Borrella burgdoferi* strain expressing OspA but not OspB. Infect. Immun. 60:1654–1868 (1992).

Ericson, J., Thor, S., Edlund, T., Jessell, T. M., and Yamada, T. Early stages of motor neuron differentiation revealed by expression of homeobox gene Islet-1. Science. 258:155–1580 (1992).

Ferguson, E. L., and Anderson, K. V. decapontaplegic acts as a morphagen to organize dorsal-ventral pattern in the Drosophila embryo. Cell. 71:451–461 (1992).

Friden, P. T., Palmer, A. M., Sioms, N. R., Bowen, D. M., Davison, A. N., Esiri, M. M. and Neary, D. Neurochemical studies of early-onset Alzheimer's disease. Possible influence on treatment. Lancet, 4:7–11 (1985).

Goulding, M., Lumsden, A., and Gruss, P. Signals from the notochord and floor plate regulate the region-specific expression of two pax genes in the developing spinal cord. Development. 117:1001–1016 (1993).

Halpern, M. E., Ho. R. K., Walker, C., and Kimmel, C. B. Induction of muscle pioneers and floor plate is distinguished by the zebrafish no tail mutation. Cell. 75:99–111 (1993).

Hamburger, V., and Hamilton, H. A series of normal stages in the development of chick embryo. J. Morphol. 88:49–92 (1951).

Hartland, R. M. (1991) In situ hybridization: an improved whole mount method for Xenopus embryos. Meth. Enzymol 36:675–685 (1991).

Hatta, K., Kimmel, C. B., Ho, R. K., and Walker, C. The cyclops mutation blocks specification of the floor plate of the zebrafish central nervous system. Nature. 350:339–341 (1991).

Heberlain, U., Wolff, T., and Rubin, G. M. The TGFβ homolog dpp and the segment polarity gene hedgehog are required for propagation of a morphogenetic eave in the Drosophila retina. Cell 75:913–926 (1993).

Heemskerk, J., and DiNardo, S. Drosophila hedgehog acts as a morphogen in cellular patterning. Cell. 76:448–460 (1994).

Hidalgo, A., and Inqham, P. Cell patterning in the Drosophila segment spatial regulation of the segment polarity gene patched. Development. 110:291–301 (1990).

Hoffman, D., Wahlberg, L. and P. Aebischer. NGF released from a polymer matrix prevents loss of ChAT expression in basal forebrain neurons following a Fimbria-Fornix lesion. Exp. Neurol., 110:39–44 (1990).

Hogan, B. L. M., Thaller, C., and Eichele, G. Evidence that Hansen's node is a site of retinoic acid synthesis. Nature. 359:237–241 (1992).

Hollyday, M., and Hamburger, V. An autoradiographic study of the formation of the lateral motor column in the chick embryo. Brain Res. 132:197–208 (1977).

Honig, L. S., and Summerbell, D. Maps of strength of positional signaling activity in the developing chick wing bud. J. Embryol. Exp. Morphol. 87:163–174 (1985).

Hornbruch, A., and Wolpert, A. Positional signaling by Hensen's node when grafted to the chick limb bud. J. Embryol. Exp. Morphol. 94:257–265 (1986).

Ingham, P. W. Localized hedgehog activity controls spatial limits of wingless transcription in the Drosophila embryo. Nature 366:560–582 (1993).

Jessell, T. M., and Dodd, J. Floor plate-derived signals and the control of neural cell pattern in vertebrates. Harvey Lect. 85:87–128 (1992).

Klar, A., Baldassare, M., and Jessell, T. M. F-spondin: a gene expressed at high levels in the floor plate encodes a secreted protein that promotes neural cell adhesion and neurite extension. Cell 89:95–110 (1992).

Knochel, S., Lef, J., Element, J., Klocke, B., Hille, S., Koster, M., and Knochel, W. Activin A induced expression of a forkhead related gene in posterior chordamesoderm of Xenopus laevis embryos. Mech. Dev. 38:157–165 (1992).

Koliatsos, V. E., Clatterbuck, R. E., Nauta, H. J. W., Knusel, B., Burton, L. E., Hefti, F., Mobley, W. C. and Price, D. L. Human nerve growth factor prevents degeneration of basal forebrain cholinergic neurons in primates. Ann. Neurol. 30:831–840 (1991b).

Korzh, V., edlund, T., and Thor, S. Zebrafish primary neurons initiate expression of the LIM homeodomain protein isl-1 at the end of gastrulation. Development. 118:417–425 (1993).

Krauss, S., Johansen, T., Korzh V., and Fjose, A. Expression pattern of zebrafish Pax genes suggests a role in early brain regionalization. Nature. 353:267–670 (1991).

Krauss, S., Concordel, J. P., and Ingham, P. W. A functionally conserved homolog of the Drosophila segment polarity gene hedgehog is expressed in tissues with polarizing activity in zebrafish embryos. Cell. 75:1431–1444 (1993).

Kyle, J., and Doolittle, R. F. A simple method for displaying the hydropathic character of a protein. J. Mol. Biol. 167:105–132 (9182).

Lai, E., Prezioso, V. R., Tao, W., Chen, W. S., and Darnell, J. E. Hepatocyte nuclear factor 3a belongs to a gene family in mammals that is homologous to the Drosophila homeotic gene fork head. Genes Dev. 5:416–427 (1992).

Lee, J. J., Von Kessler, D. P., Parks, S., and Beachy, P. A. Secretion and localization transcription suggest a role in positional signaling for products of the Ma, C., Zhou, Y., Beachy, P. A., and Moses, K. The segment polarity gene hedgehog is required for progression of the morphogenetic furrow in the developing Drosophila eye. Cell. 75:927–938 (1993).

Martinex-Arias, A., Baker, N., and Ingham, P. Role of Segment polarity genes in the definition and maintenance of cell states in the Drosophila embryo. Development. 103:157–170 (1988).

Maysinger, D., Jalsenjak, I. and Cuello, A. C. Microencapsulated nerve growth factor: effects on the forebrain neurons following devascularizing cortical lesions. Neurosci. Lett. 140:71–74 (1992).

McMahon, A. P. and Bradley, A. The Wnt-l (int-1) protooncogene is required for development of a large region of the mouse brain. Cell 62: 1073–1085 (1990).

Mohler, J. Requirements for hedgehog, a segmental polarity gene, in patterning larval and adult cuticle of Drosophila. Genetic 120:1061–1072 (1988).

Mohler, J., and Vani, K Molecular organization and embryonic expression of the hedgehog gene involved in cell-cell communication in segmental patterning of Drosophila. Development. 115:957–971 (1992).

Monaghan, A. P., Kasstner, K. H., Grau, E., and Schultz, G. Postimplantation expression patters indicate a role for the mouse forkhead/HNF-3 ($\alpha$, $\beta$, and $\delta$ genes in determination of the definitive endoderm, chordamesoderm and neuroectoderm. Development. 119:567–578 (1993).

Morata, G., and Lawrence P. A. The development of wingless, a homeotic mutation of Drosophila, Dev. Biol. 56:227–240 (1977).

Nieuwkoop, P. D., and Faber, J. Normal Table of Xenopus laevis (Daudin) (Amsterdam: North Holland) (1967).

Niswander, L., Tickle, C., Vogel, A., Booth, I., and Martin G. R. FGF-4 replaces the apical ectodermal ridge and directs outgrowth and patterning of the limb. Cell. 75:579–587 (1993).

Nusse, R. and Varmus, H. Wnt genes. Cell. 69:1073–1087 (1992).

Nussein-Volhard, c., and Wieschaus, E. Mutations affecting segment number and polarity in Drosophila. Nature. 287:795–801 (1992).

Olson, L., Nordberg, A., von Holst, H., Backman, L., Ebendahl, T., Alafuzoff, I., Amberla, K., Hartvig, P., Herlitz, A., Lilja, A. Lundquist, H. Langstron, B., Meyerson, B., Persson, A., Viitanen, M., Winblad, B. and Seiger, A. Nerve growth factor affects lC-nicotine binding, blood flow, EEG and verbal episodic memory in an Alzheimer patient. J. Neurol. Transm. [P-D Sect] 4:79–95 (1992).

Parr, B. A., Shea, M. J., Vassileva, G., and McMahon, A. P. Mouse Wnt genes exhibit discrete domains of expression in its early embryonic CNS and limb buds. Development. 119:247–261 (1993).

Patel, N. H., Martin-Bianco, E., Coleman, K. G., Poole, S. J., Ellis, M. C., Kornberg, T. B., and Goodman, C. S. Expression of engrailed proteins in arthropods, annelids and chordates. Cell. 58:955–968 (1989).

Placzek, M., Tessler-Lavigne, M., Jessell, T. M., and Dodd, J. Orientation of commissural axons in vitro in response to a floor plate derived chemostractant. Development. 110:19–30 (1990a).

Placzek, M., Tessler-Lavigne, M., Yamada, T., Jessell, T. M. and Dodd, J. Mesodermal control of neural cell identity: floor plate induction by the notochord. Science. 250:985–988 (1990b).

Placzek, M., Yamada, T., Tessler-Lavigne, M., Jessell, T. M., and Dodd, J. control of dorso-ventral pattern in vertebrate neural development induction and polarizing properties of the floor plate. Development. 113(Suppl. 2):105–122 (1991).

Placzek, M., Jessell, T. M., and Dodd, J. Induction of floor plate differentiation by contact-dependent, homeogenetic signals. Development. 117:205–218 (1993).

Posakony, L. G., Raftery, L. A., and Gelbart, W. M. Wing formation in Drosophila melanogaster requires decapentalplegic gene function along the anterior-posterior compartment boundary. Mech. Dev. 33:69–82 (1991).

Riddle R. Johnson, R. L., Laufer, E., and Tabin, C. Sonic hedgehog mediates the polarizing activity of the ZPA. Cell. 75:1401–1416 (1993).

Roelink, H., and Nusse, R. Expression of two members of the Wnt family during mouse development: restricted temporal and spatial patterns in the developing neural tube. Genes Dev. 5:381–388 (1991).

Rossant, J., Zirngibl, R., Cado, D., Shago, M., and Giguere, V. Expression of a retinoic acid response element-hsplacZ transgene defines specific domains of transcriptional activity during mouse embryogenesis. Genes Dev. 5:1333–1344 (1991).

Ruiz l Altaba, A. Planar and vertical signals in the induction and patterning of the Xenopus nervous system. Development. 115: 67–80 (1992).

Ruiz 1 Altaba, A. Xenopus. In Essential Developmental Biology: A Practical Approach, C. D. Stern and P. W. H. Holland, eds. (Oxford: IRL Press) pp. 39–44 (1993).

Ruiz 1 Altaba, A., and Jessell, T. M. Pintallavis, a gene expressed in the organizer and midline cells of frog embryos: involvement in the development of the neural axis. Development. 116:81–93 (1992).

Ruiz 1 Altaba, A., and Jessell, T. M. Midline cells and the organization of the vertebrate neuraxis. Curr. Opin. Genet. Dev. 3:633–640 (1993).

Ruiz 1 Altaba, A., and Jessell, T. M. and Klar, A. Ectopic neural expression of a floor plate marker in frog embryos injected with the midline transcription factor Pintallavis. Proc. Natl. Acad. Sci. U.S.A. 90:8268–8272 (1993a).

Ruiz l Altaba, A., Prezioso, V. R., Darnell, J. E., and Jessell, T. M. Sequential expression of HNF-3$\beta$ and HNF-3$\alpha$ by embryonic organizing centers: the dorsal lip/node, notochord and floor plate. Mech. Dev. 44:91–108 (1993b).

Sanger, F., Nicklen, S., and Coulson, A. R. DNA sequencing with chain-terminating inhibitors. Proc. Natl. Acad. Sci. U.S.A. 74:5463 (1977).

Sasaki, H., and Hogan, B. L. M. Differentiation expression of multiple forkhead regrated genes during gastrulation and axial pattern formation in the mouse embryo. Development. 118:47–59 (1977). Sasaki, H., and Hogan, B. L. M. HNG-3 as a regulator of floor plate development. Cell. 76:103–116

Schaeren-Wiemers, N., and Gerlin-Mosar, A. A single protocol to detect transcripts of various types and expression levels in neural tissue and cultured cells: in situ hybridization using digoxigeninlabeled cRNA probes. Histochemistry. 100:431–440 (1993).

Spencer, F. A., Hoffmann, F. M., and Gelbert, W. M. Decapentaplogic: a gene complex affecting morphogenesis in Drosophila metanogaster. Cell. 28:451–461 (1982).

Stoker, K. M., and Carlson, B. M. Hensen's node, but not other biological signallers can induce dupernumerary digits in the developing chick limb bud. Roux's Arch. Dev. Biol. 198:371–381 (1990).

Strahie, U., Blader, P., Henrique, D., and Ingham, P. Axial, a target gene of mesoderm and neural indication, shows altered expression in cyclops mutant zebrafish embryos. Genes. Dev. &:1438–1446 (1993).

Struhl, G., and Basler, K., Organizing activity of wingless protein in Drosophila. Cell. 72:527–540 (1993).

Tebata, T., Eaton, S., and Kornberg, T. B. The Drosophila hedgehog gene is expressed specifically in posterior compartment cells and is a target of engrailed regulation. Genes Dev. 6:2835–2646 (1992).

Tanaka, H., and Obata, K. Developmental changes in unique cell surface antigens of chick embryo spinal motor neurons and ganglion cells. Dev. Biol. 106:26–37 (1984).

Tashiro, S., Michiue, T., Higashijima, S., Zenno, S., Ishlmaru, S., Takahashi, F., Orlhara, M., Kojima, T., and Saigo, K. Structure and expression of hedgehog, a Drosophila segment-polarity gene required for cell-cell communication. Gene. 124:183–189 (1993).

Taylor, A. M., Nakano, Y., Mohler, J., and Ingham, P. W. Contrasting distributions of patched and hedgehog proteins in the Drosophila embryo. Mech. Dev. 42:89–96 (1993).

Tessler-Lavigne, M., Placzek, M., Lumsden, A. G. S., Dodd, J., and Jessell, T. M. Chemotropic guidance of developing axons in the mammalian central nervous system. Nature. 336:775–778. (1988).

Thalier, C., and Elchele, G. Identification and spatial distribution of retinoids in the developing chick limb bud. Nature 327:625–628 (1987).

Thomas, K. R., and Capecchi, M. R. Targeted disruption of the murine int-1 proto-oncogene resulting in severe abnormalities in midbrain and cerebellar development. Nature. 346:847–850 (1990).

Thor. S., Ericson, J., Brannstrom, T., and Edlund, T. The homeodomain LIM protein Isl-1 is expressed in subsets of neurons an dendocrine cells in the adult rat. Neuron. 7:881–889 (1991).

Van Straaten, H. M. W., and Hekking, J. W. M. Development of floor plate, neurons and axonal outgrowth pattern in the early spinal cord of the notochord-deficient chick embryo. Anat. Embryol. 184:55–63 (1991).

Van Straaten, H. M. W., Hekking, J. W. M., Wiertz-Hoesseis, E. L. Thors, F., and Drukker, J. Effect of the notochord on the differentiation of a floor plate area in the neural tube of the chick embryo. Anal. Embryol. 177:317–324 (1989).

Vogel, A., and Tickle, C. FGF-4 maintains polarizing activity of posterior limb bud cells in vivo and in vitro. Development. 119:199–206 (1993).

von Heijine, G. Signal sequences: the limits of variation. J. Mol. Biol. 184:99–105 (1985).

Wagner, M., Thaller, C., Jessell, T. M., and Elchele, G. Polarizing activity and retinoid synthesis in the floor plate of the neural tube. Nature. 345:819–822 (1990).

Wagner, M., Han, B., and Jessell, T. M. Regional differences in retinoid release from embryonic neural tissue detected by an in vitro reporter assay. Development. 116:55–66 (1992).

Welgel, D., and Jackie, H. The fork head domain: a novel DNA binding motif of eukaryotic transcription factor? Cell. 63:455–458 (1990).

Whiting, J., Marshall, H., Cook, M., Krumlauf, R., Rigby, P. W., Stolt, D., and Allemann, R. K. Multiple spatially specific enhancers are required to reconstruct the patter of Hox-2.6 gene expression. Genes Dev. 5:2048–2059 (1991).

Yamada, T., Placzek, M., Tanaka, H., Dodd, J., and Jessell, T. M. Control of cell pattern in the developing nervous system: polarizing activity of the floor plate and notochord. Cell 64:635–647 (1991).

Yamada, T., Plaff, S. L., Edlund, T., and Jossell, T. M. Control of cell pattern in the neural tube: motor neuron induction by diffusible factors from notochord and floor plate. Cell. 73:673–686.

What is claimed is:

1. A purified Vertebrate hedgehog protein-1 (Vhh-1) protein having the amino acid sequence set forth in (SEQ ID NO: 2) wherein the Vhh-1 is a rat protein.

* * * * *

SEQUENCE LISTING

```
<160> NUMBER OF SEQ ID NOS: 9

<210> SEQ ID NO 1
<211> LENGTH: 1715
<212> TYPE: DNA
<213> ORGANISM: RAT
<220> FEATURE:
<221> NAME/KEY: CDS
<222> LOCATION: (315)..(1625)

<400> SEQUENCE: 1
ttaaaatcag gctcttttg tcttttaatt gccgtctcga gacccaactc cgatgtgttc      60
cgttaccagc gaccggcagc ctgccatcgc agcccctgtc tgggtgggga tcggagacaa    120
gtcccctgca gcaacagcag gcaaggttat ataggaagag aaagagccag gcagcgccag    180
agggaacgaa cgagccgagc gaggaaggga gagccgagcg caaggaggag cgcacacgca    240 cacaccgcg cgtaccagct cgcgcacaga ccggcgcggg gacggctcgc aagtcctcag    300
gttccgcgga cgag atg ctg ctg ctg ctg gcc aga tgt ttt ctg gtg gcc    350
              Met Leu Leu Leu Leu Ala Arg Cys Phe Leu Val Ala
              1               5                  10
```

-continued

| | | |
|---|---|---|
| ctt gct tcc tcg ctg ctg gtg tgc ccc gga ctg gcc tgt ggg ccc ggc<br>Leu Ala Ser Ser Leu Leu Val Cys Pro Gly Leu Ala Cys Gly Pro Gly<br>15                                      20                         25 | | 398 |
| agg ggg ttt gga aag agg cag cac ccc aaa aag ctg acc cct tta gcc<br>Arg Gly Phe Gly Lys Arg Gln His Pro Lys Lys Leu Thr Pro Leu Ala<br>    30                                  35                         40 | | 446 |
| tac aag cag ttt atc ccc aac gta gcc gag aag acc cta ggg gcc agc<br>Tyr Lys Gln Phe Ile Pro Asn Val Ala Glu Lys Thr Leu Gly Ala Ser<br>45                                      50                        55                         60 | | 494 |
| ggc cga tat gaa ggg aag atc aca aga aac tcc gaa cga ttt aag gaa<br>Gly Arg Tyr Glu Gly Lys Ile Thr Arg Asn Ser Glu Arg Phe Lys Glu<br>                                65                             70                           75 | | 542 |
| ctc acc ccc aat tac aac ccc gac atc ata ttt aag gat gag gaa aac<br>Leu Thr Pro Asn Tyr Asn Pro Asp Ile Ile Phe Lys Asp Glu Glu Asn<br>                80                               85                         90 | | 590 |
| act gga gca gac cgg ctg atg act cag agg tgc aaa gac aag tta aat<br>Thr Gly Ala Asp Arg Leu Met Thr Gln Arg Cys Lys Asp Lys Leu Asn<br>                             95                             100                         105 | | 638 |
| gcc ttg gcc atc tcc gtg atg aac cag tgg cct gga gtg aag ctt cga<br>Ala Leu Ala Ile Ser Val Met Asn Gln Trp Pro Gly Val Lys Leu Arg<br>110                                    115                        120 | | 686 |
| gtg act gag ggc tgg gat gag gac ggc cat cat tca gag gag tct cta<br>Val Thr Glu Gly Trp Asp Glu Asp Gly His His Ser Glu Glu Ser Leu<br>125                                    130                        135                       140 | | 734 |
| cac tat gag ggt cga gca gtg gac atc acc acg tct gac agg gac cgc<br>His Tyr Glu Gly Arg Ala Val Asp Ile Thr Thr Ser Asp Arg Asp Arg<br>                              145                        150                       155 | | 782 |
| agc aag tat ggc atg ctg gct cgc ctg gct gtg gag gct gga ttc gac<br>Ser Lys Tyr Gly Met Leu Ala Arg Leu Ala Val Glu Ala Gly Phe Asp<br>               160                             165                       170 | | 830 |
| tgg gtc tac tat gaa tcc aaa gct cgc atc cac tgc tct gtg aaa gca<br>Trp Val Tyr Tyr Glu Ser Lys Ala Arg Ile His Cys Ser Val Lys Ala<br>                175                             180                      185 | | 878 |
| gag aac tcc gtg gcg gcc aaa tct gac ggc tgc ttc ccg gga tca gcc<br>Glu Asn Ser Val Ala Ala Lys Ser Asp Gly Cys Phe Pro Gly Ser Ala<br>                190                           195                       200 | | 926 |
| aca gtg cac ctg gag cag ggt ggc acc aag tta gtg aag gat cta agt<br>Thr Val His Leu Glu Gln Gly Gly Thr Lys Leu Val Lys Asp Leu Ser<br>205                                    210                        215                       220 | | 974 |
| ccc ggg gac cgc gtg ctg gcg gct gac gac cag ggc cgg ctg ctg tac<br>Pro Gly Asp Arg Val Leu Ala Ala Asp Asp Gln Gly Arg Leu Leu Tyr<br>                            225                           230                       235 | | 1022 |
| agc gac ttc ctc acc ttc ctg gac cgc gac gaa ggt gcc aag aag gtc<br>Ser Asp Phe Leu Thr Phe Leu Asp Arg Asp Glu Gly Ala Lys Lys Val<br>               240                           245                        250 | | 1070 |
| ttc tac gtg atc gag acg cgg gag ccg cgg gag cgt ctg ctg ctc act<br>Phe Tyr Val Ile Glu Thr Arg Glu Pro Arg Glu Arg Leu Leu Leu Thr<br>                255                             260                      265 | | 1118 |
| gcc gcg cac ctg ctc ttc gtg gcg ccg cac aac gac tcc ggg ccc act<br>Ala Ala His Leu Leu Phe Val Ala Pro His Asn Asp Ser Gly Pro Thr<br>270                                    275                        280 | | 1166 |
| ccg gga ccg agc cca ctc ttc gcc agc cgc gtg cgt ccg ggg cag cgc<br>Pro Gly Pro Ser Pro Leu Phe Ala Ser Arg Val Arg Pro Gly Gln Arg<br>285                                    290                        295                       300 | | 1214 |
| gtg tac gtg gtg gct gaa cgc ggc ggg gac cgc cgg ctg ctg ccc gcc<br>Val Tyr Val Val Ala Glu Arg Gly Gly Asp Arg Arg Leu Leu Pro Ala<br>                            305                           310                       315 | | 1262 |
| gcg gtg cac agc gta acg cta cga gag gag gcg gcg ggt gcg tac gcg<br>Ala Val His Ser Val Thr Leu Arg Glu Glu Ala Ala Gly Ala Tyr Ala<br>                            320                           325                       330 | | 1310 |

```
ccg ctc acg gcg gac ggc acc att ctc atc aac cgg gtg ctc gcc tcg    1358
Pro Leu Thr Ala Asp Gly Thr Ile Leu Ile Asn Arg Val Leu Ala Ser
        335                 340                 345 tgc tac gca gtc atc gag gag cac agc tgg gca cac cgg gcc ttc gcg    1406
Cys Tyr Ala Val Ile Glu Glu His Ser Trp Ala His Arg Ala Phe Ala
        350                 355                 360 ccc ttc cgc ctg gcg cac gcg ctg ctg gcc gcg ctg gca ccc gcc cgc    1454
Pro Phe Arg Leu Ala His Ala Leu Leu Ala Ala Leu Ala Pro Ala Arg
365                 370                 375                 380 acg gac ggc ggg ggc ggg ggc agc atc cct gcc ccg caa tct gta gcg    1502
Thr Asp Gly Gly Gly Gly Gly Ser Ile Pro Ala Pro Gln Ser Val Ala
                385                 390                 395 gaa gcg agg ggc gca ggg ccg cct gcg ggc atc cac tgg tac tcg cag    1550
Glu Ala Arg Gly Ala Gly Pro Pro Ala Gly Ile His Trp Tyr Ser Gln
            400                 405                 410 ctg ctg tac cac att ggc acc tgg ctg ttg gac agc gag acc ctg cat    1598
Leu Leu Tyr His Ile Gly Thr Trp Leu Leu Asp Ser Glu Thr Leu His
            415                 420                 425 ccc ttg gga atg gca gtc aag tcc agc tgaagtccga cgggaccggg          1645
Pro Leu Gly Met Ala Val Lys Ser Ser
        430                 435 caggggcgt gggggcgggc gggcgggaa gcgactgcca gataagcaac cgggaaagcg    1705
cacggaagga                                                         1715

<210> SEQ ID NO 2
<211> LENGTH: 437
<212> TYPE: PRT
<213> ORGANISM: RAT

<400> SEQUENCE: 2

Met Leu Leu Leu Ala Arg Cys Phe Leu Val Ala Leu Ala Ser Ser
1               5                   10                  15

Leu Leu Val Cys Pro Gly Leu Ala Cys Gly Pro Gly Arg Gly Phe Gly
            20                  25                  30

Lys Arg Gln His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
    50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Lys Leu Arg Val Thr Glu Gly
        115                 120                 125

Trp Asp Glu Asp Gly His His Ser Glu Glu Ser Leu His Tyr Glu Gly
    130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala Arg Ile His Cys Ser Val Lys Ala Glu Asn Ser Val
            180                 185                 190

Ala Ala Lys Ser Asp Gly Cys Phe Pro Gly Ser Ala Thr Val His Leu
        195                 200                 205
```

```
Glu Gln Gly Gly Thr Lys Leu Val Lys Asp Leu Ser Pro Gly Asp Arg
    210                 215                 220
Val Leu Ala Ala Asp Asp Gln Gly Arg Leu Leu Tyr Ser Asp Phe Leu
225                 230                 235                 240
Thr Phe Leu Asp Arg Asp Glu Gly Ala Lys Lys Val Phe Tyr Val Ile
                245                 250                 255
Glu Thr Arg Glu Pro Arg Glu Arg Leu Leu Thr Ala Ala His Leu
            260                 265                 270
Leu Phe Val Ala Pro His Asn Asp Ser Gly Pro Thr Pro Gly Pro Ser
        275                 280                 285
Pro Leu Phe Ala Ser Arg Val Arg Pro Gly Gln Arg Val Tyr Val Val
    290                 295                 300
Ala Glu Arg Gly Gly Asp Arg Arg Leu Leu Pro Ala Ala Val His Ser
305                 310                 315                 320
Val Thr Leu Arg Glu Glu Ala Ala Gly Ala Tyr Ala Pro Leu Thr Ala
                325                 330                 335
Asp Gly Thr Ile Leu Ile Asn Arg Val Leu Ala Ser Cys Tyr Ala Val
            340                 345                 350
Ile Glu Glu His Ser Trp Ala His Arg Ala Phe Ala Pro Phe Arg Leu
        355                 360                 365
Ala His Ala Leu Leu Ala Ala Leu Ala Pro Ala Arg Thr Asp Gly Gly
    370                 375                 380
Gly Gly Gly Ser Ile Pro Ala Pro Gln Ser Val Ala Glu Ala Arg Gly
385                 390                 395                 400
Ala Gly Pro Pro Ala Gly Ile His Trp Tyr Ser Gln Leu Leu Tyr His
                405                 410                 415
Ile Gly Thr Trp Leu Leu Asp Ser Glu Thr Leu His Pro Leu Gly Met
            420                 425                 430
Ala Val Lys Ser Ser
            435

<210> SEQ ID NO 3
<211> LENGTH: 20
<212> TYPE: DNA
<213> ORGANISM: Drosophila

<400> SEQUENCE: 3
gaggattggg tcgtcatagg                                                    20

<210> SEQ ID NO 4
<211> LENGTH: 20
<212> TYPE: DNA
<213> ORGANISM: Drosophila

<400> SEQUENCE: 4
cttcaaggat tccatctcaa                                                    20

<210> SEQ ID NO 5
<211> LENGTH: 22
<212> TYPE: DNA
<213> ORGANISM: Drosophila

<400> SEQUENCE: 5
agctgggacg aggactacca tc                                                 22

<210> SEQ ID NO 6
<211> LENGTH: 22
```

-continued

```
<212> TYPE: DNA
<213> ORGANISM: Drosophila

<400> SEQUENCE: 6
tgggaactga tcgacgaatc tg                                              22

<210> SEQ ID NO 7
<211> LENGTH: 418
<212> TYPE: PRT
<213> ORGANISM: zebra fish

<400> SEQUENCE: 7
```

Met Arg Leu Leu Thr Arg Val Leu Val Ser Leu Leu Thr Leu Ser
1               5                   10                  15

Leu Val Val Ser Gly Leu Ala Cys Gly Pro Gly Arg Gly Tyr Gly Arg
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Thr Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ser Leu Ala Ile Ser
            100                 105                 110

Val Met Asn His Trp Pro Gly Val Lys Leu Arg Val Thr Glu Gly Trp
        115                 120                 125

Asp Glu Asp Gly His His Phe Glu Glu Ser Leu His Tyr Glu Gly Arg
    130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
    210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
            260                 265                 270

Phe Val Leu Asp Asn Ser Thr Glu Asp Leu His Thr Met Thr Ala Ala
        275                 280                 285

Tyr Ala Ser Ser Val Arg Ala Gly Gln Lys Val Met Val Val Asp Asp
    290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu

-continued

```
                   340                 345                 350
Ala His Leu Ala Phe Ala Pro Ala Arg Leu Tyr Tyr Tyr Val Ser Ser
            355                 360                 365
Phe Leu Phe Pro Gln Asn Ser Ser Arg Ser Asn Ala Thr Leu Gln
        370                 375                 380
Gln Glu Gly Val His Trp Tyr Ser Arg Leu Leu Tyr Gln Met Gly Thr
385                 390                 395                 400
Trp Leu Leu Asp Ser Asn Met Leu His Pro Leu Gly Met Ser Val Asn
                405                 410                 415
Ser Ser

<210> SEQ ID NO 8
<211> LENGTH: 471
<212> TYPE: PRT
<213> ORGANISM: Drosophila

<400> SEQUENCE: 8

Met Asp Asn His Ser Ser Val Pro Trp Ala Ser Ala Ser Val Thr
1               5                   10                  15
Cys Leu Ser Leu Asp Ala Lys Cys His Ser Ser Ser Ser Ser Ser
                20                  25                  30
Ser Lys Ser Ala Ala Ser Ser Ile Ser Ala Ile Pro Gln Glu Glu Thr
            35                  40                  45
Gln Thr Met Arg His Ile Ala His Thr Gln Arg Cys Leu Ser Arg Leu
        50                  55                  60
Thr Ser Leu Val Ala Leu Leu Ile Val Leu Pro Met Val Phe Ser
65                  70                  75                  80
Pro Ala His Ser Cys Gly Pro Gly Arg Gly Leu Gly Arg His Arg Ala
                85                  90                  95
Arg Asn Leu Tyr Pro Leu Val Leu Lys Gln Thr Ile Pro Asn Leu Ser
            100                 105                 110
Glu Tyr Thr Asn Ser Ala Ser Gly Pro Leu Glu Gly Val Ile Arg Arg
        115                 120                 125
Asp Ser Pro Lys Phe Lys Asp Leu Val Pro Asn Tyr Asn Arg Asp Ile
130                 135                 140
Leu Phe Arg Asp Glu Glu Gly Thr Gly Ala Asp Arg Leu Met Ser Lys
145                 150                 155                 160
Arg Cys Lys Glu Lys Leu Asn Val Leu Ala Tyr Ser Val Met Asn Glu
                165                 170                 175
Trp Pro Gly Ile Arg Leu Leu Val Thr Glu Ser Trp Asp Glu Asp Tyr
            180                 185                 190
His His Gly Gln Glu Ser Leu His Tyr Glu Gly Arg Ala Val Thr Ile
        195                 200                 205
Ala Thr Ser Asp Arg Asp Gln Ser Lys Tyr Gly Met Leu Ala Arg Leu
        210                 215                 220
Ala Val Glu Ala Gly Phe Asp Trp Val Ser Tyr Val Ser Arg Arg His
225                 230                 235                 240
Ile Tyr Cys Ser Val Lys Ser Asp Ser Ser Ile Ser Ser His Val His
                245                 250                 255
Gly Cys Phe Thr Pro Glu Ser Thr Ala Leu Leu Glu Ser Gly Val Arg
            260                 265                 270
Lys Pro Leu Gly Glu Leu Ser Ile Gly Asp Arg Val Leu Ser Met Thr
        275                 280                 285
Ala Asn Gly Gln Ala Val Tyr Ser Glu Val Ile Leu Phe Met Asp Arg
```

-continued

```
                290                 295                 300
Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala Asp Arg Ile Glu Glu Lys
                340                 345                 350

Asn Gln Val Leu Val Arg Asp Val Glu Thr Gly Glu Leu Arg Pro Gln
                355                 360                 365

Arg Val Val Lys Val Gly Ser Val Arg Ser Lys Gly Val Val Ala Pro
370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
                420                 425                 430

Leu His Ser Ser Pro Lys Val Val Ser Ala Gln Gln Gln Asn Gly
                435                 440                 445

Ile His Trp Tyr Ala Asn Ala Leu Tyr Lys Val Lys Asp Tyr Val Leu
                450                 455                 460

Pro Gln Ser Trp Arg His Asp
465                 470

<210> SEQ ID NO 9
<211> LENGTH: 437
<212> TYPE: PRT
<213> ORGANISM: Rat

<400> SEQUENCE: 9

Met Leu Leu Leu Leu Ala Arg Cys Phe Leu Val Ala Leu Ala Ser Ser
1               5                   10                  15

Leu Leu Val Cys Pro Gly Leu Ala Cys Gly Pro Gly Arg Gly Phe Gly
                20                  25                  30

Lys Arg Gln His Pro Lys Lys Leu Thr Pro Leu Ala Tyr Lys Gln Phe
                35                  40                  45

Ile Pro Asn Val Ala Glu Lys Thr Leu Gly Ala Ser Gly Arg Tyr Glu
50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
                100                 105                 110

Ser Val Met Asn Gln Trp Pro Gly Val Lys Leu Arg Val Thr Glu Gly
                115                 120                 125

Trp Asp Glu Asp Gly His His Ser Glu Glu Ser Leu His Tyr Glu Gly
                130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala Arg Ile His Cys Ser Val Lys Ala Glu Asn Ser Val
                180                 185                 190
```

-continued

```
Ala Ala Lys Ser Asp Gly Cys Phe Pro Gly Ser Ala Thr Val His Leu
        195                 200                 205
Glu Gln Gly Gly Thr Lys Leu Val Lys Asp Leu Ser Pro Gly Asp Arg
        210                 215                 220
Val Leu Ala Ala Asp Asp Gln Gly Arg Leu Leu Tyr Ser Asp Phe Leu
225                 230                 235                 240
Thr Phe Leu Asp Arg Asp Glu Gly Ala Lys Lys Val Phe Tyr Val Ile
                245                 250                 255
Glu Thr Arg Glu Pro Arg Glu Arg Leu Leu Leu Thr Ala Ala His Leu
            260                 265                 270
Leu Phe Val Ala Pro His Asn Asp Ser Gly Pro Thr Pro Gly Pro Ser
        275                 280                 285
Pro Leu Phe Ala Ser Arg Val Arg Pro Gly Gln Arg Val Tyr Val Val
        290                 295                 300
Ala Glu Arg Gly Gly Asp Arg Arg Leu Leu Pro Ala Ala Val His Ser
305                 310                 315                 320
Val Thr Leu Arg Glu Glu Ala Ala Gly Ala Tyr Ala Pro Leu Thr Ala
                325                 330                 335
Asp Gly Thr Ile Leu Ile Asn Arg Val Leu Ala Ser Cys Tyr Ala Val
            340                 345                 350
Ile Glu Glu His Ser Trp Ala His Arg Ala Phe Ala Pro Phe Arg Leu
            355                 360                 365
Ala His Ala Leu Leu Ala Ala Leu Ala Pro Ala Arg Thr Asp Gly Gly
        370                 375                 380
Gly Gly Gly Ser Ile Pro Ala Pro Gln Ser Val Ala Glu Ala Arg Gly
385                 390                 395                 400
Ala Gly Pro Pro Ala Gly Ile His Trp Tyr Ser Gln Leu Leu Tyr His
                405                 410                 415
Ile Gly Thr Trp Leu Leu Asp Ser Glu Thr Leu His Pro Leu Gly Met
            420                 425                 430
Ala Val Lys Ser Ser
            435
```